(12) United States Patent
Yamada

(10) Patent No.: US 10,463,546 B2
(45) Date of Patent: Nov. 5, 2019

(54) DISPOSABLE CLOTHING ARTICLE

(71) Applicant: Kikuo Yamada, Shinagawa-ku (JP)

(72) Inventor: Kikuo Yamada, Shinagawa-ku (JP)

(*) Notice: Subject to any disclaimer, the term of this patent is extended or adjusted under 35 U.S.C. 154(b) by 90 days.

(21) Appl. No.: 15/533,886

(22) PCT Filed: Dec. 14, 2015

(86) PCT No.: PCT/JP2015/085432
§ 371 (c)(1),
(2) Date: Jun. 7, 2017

(87) PCT Pub. No.: WO2016/093371
PCT Pub. Date: Jun. 16, 2016

(65) Prior Publication Data
US 2017/0340489 A1   Nov. 30, 2017

Related U.S. Application Data

(60) Provisional application No. 62/204,070, filed on Aug. 12, 2015.

(30) Foreign Application Priority Data

Dec. 12, 2014   (WO) .................. PCT/JP2014/083062

(51) Int. Cl.
*A61F 13/496* (2006.01)
*A61F 13/49* (2006.01)

(52) U.S. Cl.
CPC ...... *A61F 13/496* (2013.01); *A61F 13/49009* (2013.01)

(58) Field of Classification Search
CPC .......... A61F 13/49009; A61F 13/49011; A61F 13/49012; A61F 13/49017;
(Continued)

(56) References Cited

U.S. PATENT DOCUMENTS 5,745,922 A * 5/1998 Rajala ............... A61F 13/15593
2/243.1
6,264,643 B1 7/2001 Toyoda
(Continued)

FOREIGN PATENT DOCUMENTS

CN    1103775 A    6/1995
CN    102614051 A   8/2012
(Continued)

OTHER PUBLICATIONS

International Search Report dated Mar. 22, 2016, in PCT/JP2015/085432 filed Dec. 14, 2015.
(Continued)

*Primary Examiner* — Adam Marcetich
*Assistant Examiner* — Jessica R Arble
(74) *Attorney, Agent, or Firm* — Oblon, McClelland, Maier & Neustadt, L.L.P.

(57) ABSTRACT

A disposable garment that prevents urine leakage, has superior appearance, and reduces reluctance of the wearer to wear the garment.

The disposable garment (1) comprises a torso band (21) comprising a torso band opening (21*a*); and a chassis (20) disposed on a lower side of the torso band (21); wherein the chassis (20) comprises a stretchable composite sheet, the stretchable composite sheet being a multi-layer structure comprising a first air permeable sheet (203), a second air permeable sheet (205), and a liquid diffusion fiber sheet (201) and a linear elastic body (202) disposed between the first air permeable sheet (203) and the second air permeable sheet (205), and the chassis (20) has stretchability that imparts a pressing force against a wearer.

29 Claims, 64 Drawing Sheets

(58) Field of Classification Search
CPC .. A61F 2013/49022; A61F 2013/49023; A61F 2013/49025; A61F 2013/49026; A61F 2013/49028; A61F 2013/4903
See application file for complete search history.

(56) References Cited

U.S. PATENT DOCUMENTS

| | | | | |
|---|---|---|---|---|
| 2003/0114825 | A1* | 6/2003 | Morman | A61F 13/15593 604/385.27 |
| 2003/0125697 | A1 | 7/2003 | Bushman et al. | |
| 2004/0230171 | A1* | 11/2004 | Ando | A61F 13/15593 604/355 |
| 2006/0070701 | A1 | 4/2006 | Kobayashi et al. | |
| 2007/0244455 | A1* | 10/2007 | Hansson | A61F 13/4704 604/385.201 |
| 2008/0103469 | A1 | 5/2008 | Bushman et al. | |
| 2009/0177176 | A1 | 7/2009 | Saito | |
| 2009/0306616 | A1 | 12/2009 | Wennerbäck | |
| 2013/0110075 | A1 | 5/2013 | Mukai et al. | |
| 2013/0331807 | A1 | 12/2013 | Ichihara et al. | |
| 2014/0171895 | A1* | 6/2014 | Thomas | A61F 13/49012 604/385.3 |
| 2016/0106601 | A1* | 4/2016 | Kobayashi | A61F 13/49058 604/385.16 |

FOREIGN PATENT DOCUMENTS

| | | |
|---|---|---|
| CN | 102858297 A | 1/2013 |
| EP | 1 642 557 A1 | 4/2006 |
| EP | 2 011 464 A1 | 1/2009 |
| EP | 2 682 081 A1 | 1/2014 |
| JP | 2002-153509 A | 5/2002 |
| JP | 2005-46227 A | 2/2005 |
| JP | 2005-137587 A | 6/2005 |
| JP | 2006-103068 A | 4/2006 |
| JP | 2007-105115 A | 4/2007 |
| JP | 2007-167166 A | 7/2007 |
| JP | 2012-70838 A | 4/2012 |
| JP | 2012-210234 A | 11/2012 |
| JP | 2013-27600 A | 2/2013 |
| JP | 2013-544110 A | 12/2013 |
| WO | WO 2016/093371 A1 | 6/2016 |

OTHER PUBLICATIONS

Extended European Search Report dated Jun. 20, 2018 in Patent Application No. 15868352.4.
Combined Office Action and Search Report dated Jul. 13, 2018 in Chinese Patent Application No. 201580068038.5 (with English translation of categories of cited documents), 10 pages.
Office Action dated Mar. 12, 2019 in Japanese Patent Application No. 2018-098286.
Combined Office Action and Search Report dated Apr. 1, 2019 in Chinese Patent Application No. 201580068038.5, (with English translation of category of cited documents) 10 pages.

* cited by examiner

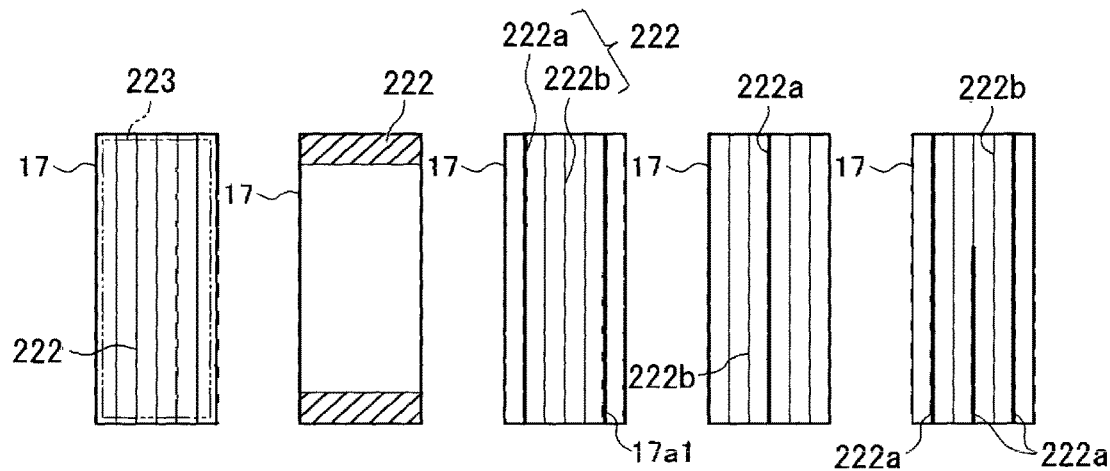
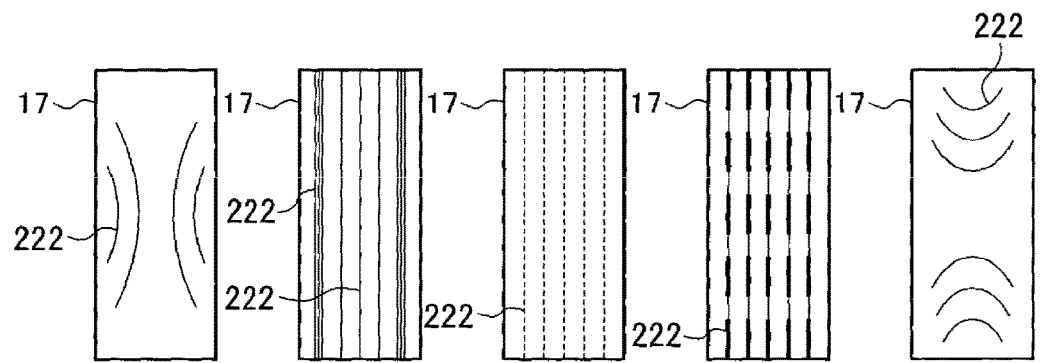

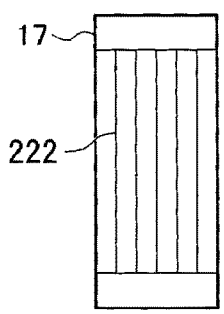 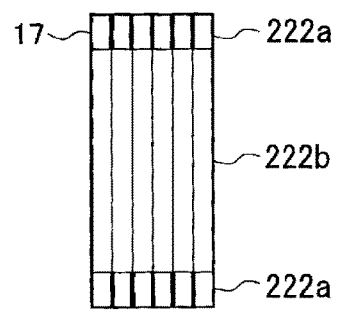 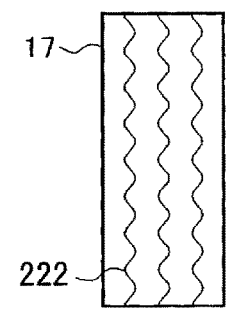 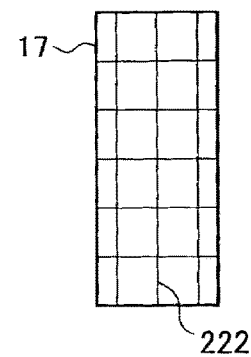
FIG. 16A    FIG. 16B    FIG. 16C    FIG. 16D
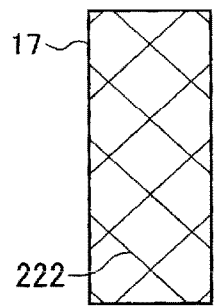 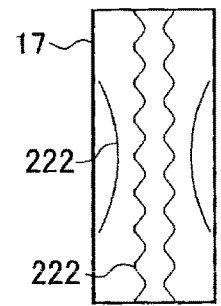 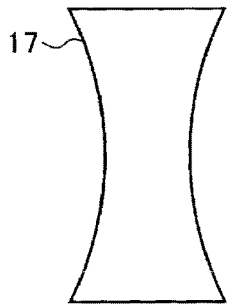 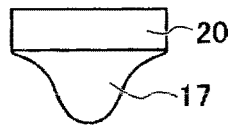
FIG. 16E    FIG. 16F    FIG. 16G    FIG. 16H

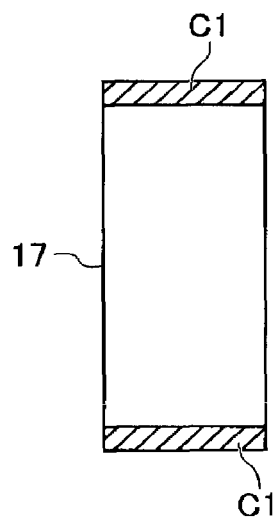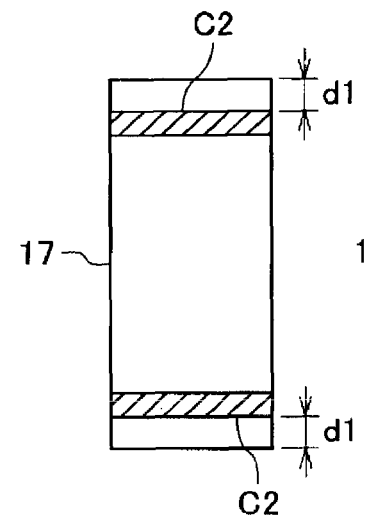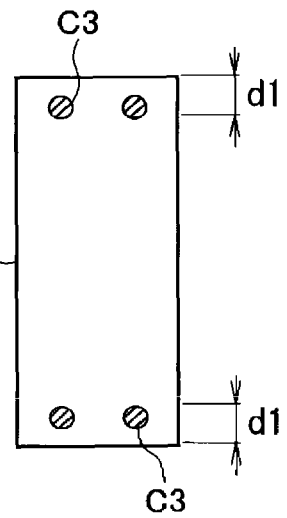
FIG. 23A  FIG. 23B  FIG. 23C
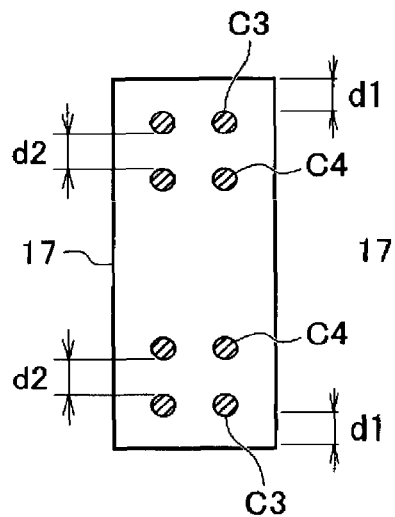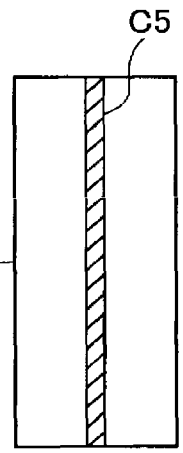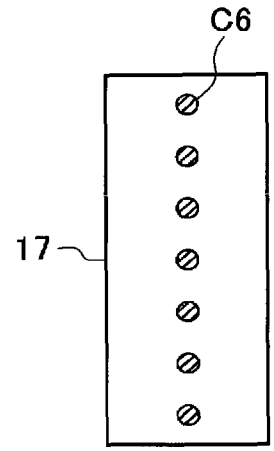
FIG. 23D  FIG. 23E  FIG. 23F

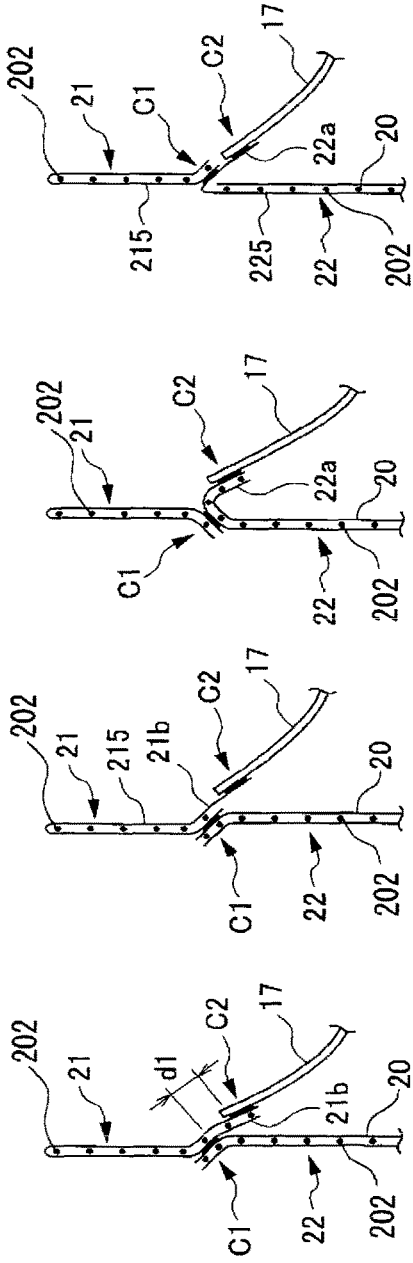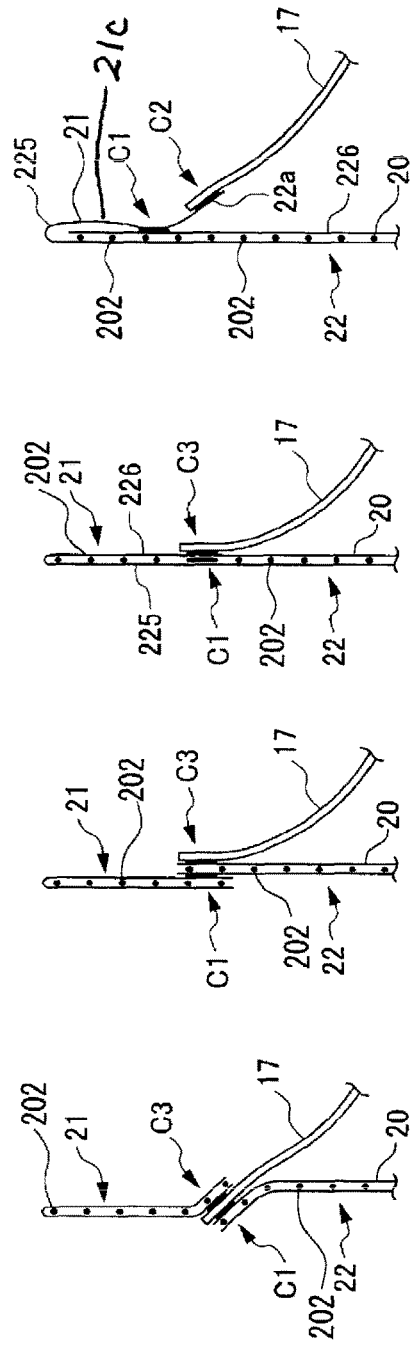

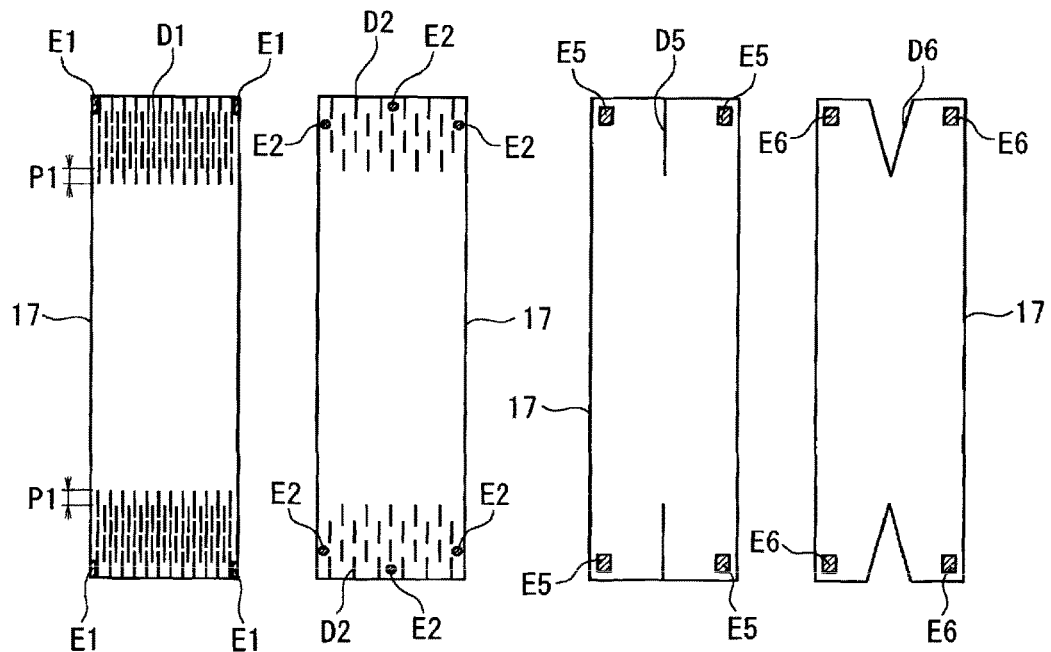
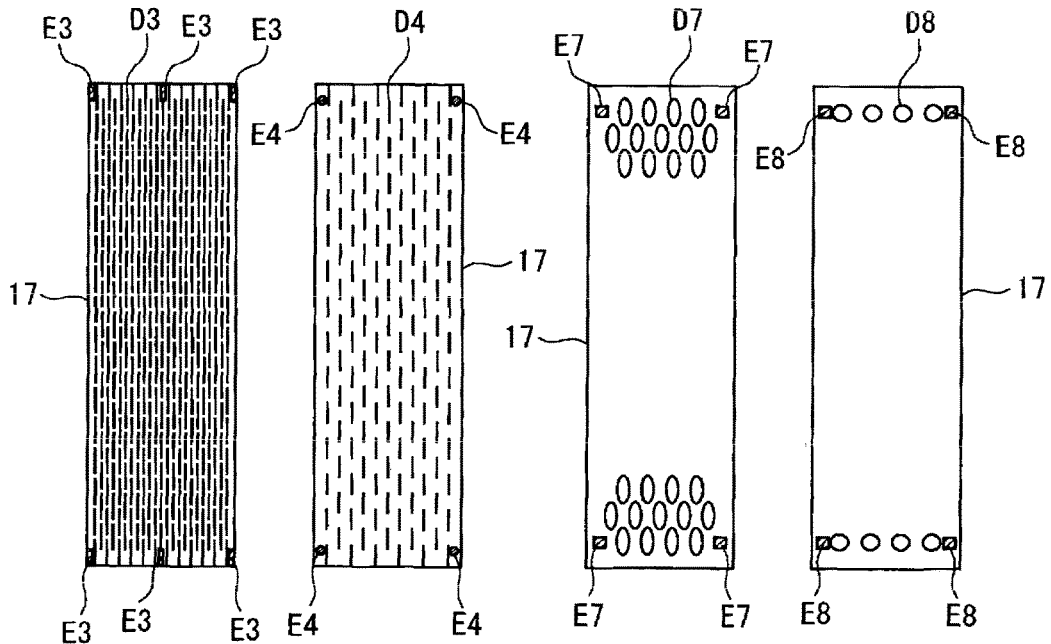
FIG. 35A  FIG. 35B  FIG. 35E  FIG. 35F
FIG. 35C  FIG. 35D  FIG. 35G  FIG. 35H

DISPOSABLE CLOTHING ARTICLE

TECHNICAL FIELD

The present invention relates to a disposable garment.

BACKGROUND ART

Examples of disposable garments include diapers and pull up pants. PTL 1 describes a pants-type diaper provided with gathers on leg cuff portions. The pants-type diaper includes a nonwoven fabric with stretchability to provide a good fit to the body of the wearer. PTL 2 describes a pants-type diaper provided with gathers on leg cuff portions. The leg cuff portions include a sheet made from two fibrous sheets, which include nonwoven fabric and/or synthetic paper, and an elastic member disposed between the two fibrous sheets in a tensioned state, the two fibrous sheets and the elastic member being joined together.

CITATION LIST

Patent Literature

PTL 1: Japanese Unexamined Patent Application Publication No. 2005-137587A
PTL 2: Japanese Unexamined Patent Application Publication No. 2006-103068A

SUMMARY OF INVENTION

Technical Problem

Conventional pants-type diapers are provided with leg cuff gathers to prevent leakage. However, the contact between the absorbent member (absorbent core) and the body of the wearer can be insufficient and a gap may be formed therebetween. Thus, when the amount of urine discharged exceeds the absorbance capacity of the absorbent member, or when the urine does not reach the absorbent member, urine may leak from such a gap to the abdomen. Urine that is not absorbed by the absorbent member runs along the body of the wearer and reaches the side gathers such as the leg cuff gathers of the disposable diaper. Side gathers are made of a nonwoven fabric and are not intrinsically absorbent. Thus, disposable diapers provided with side gathers such as leg cuff gathers have difficulty reliably preventing urine leakage. Additionally, conventional disposable diapers are designed so that when urine is absorbed, only the area where the urine is absorbed expands and swells. This makes it visually obvious that urine was discharged, and thus such a state is undesirable for the wearer. Such concerns also apply to women during their menstrual cycle. Furthermore, conventional diapers are made from a material with air permeability such as a nonwoven fabric, but do not always have sufficient air permeability and moisture permeability. Also, problems exist with insufficient skin comfort and insufficient absorbency and quick drying ability leading to a lack of wear-ability.

In light of such problems with conventional disposable garments, an embodiment of the present invention provides a disposable garment with excellent air permeability, moisture permeability, absorbency and quick drying ability, and fit for the wearer. The disposable garment minimizes or prevents urine leakage and reduces reluctance of the wearer in terms of wear-ability, even when the disposable garment is a diaper.

Solution to Problem

Embodiments of the present invention include:
(1) A disposable garment, comprising:
a torso band comprising a torso band opening; and
a chassis disposed on a lower side of the torso band; wherein
the chassis comprises a stretchable composite sheet, the stretchable composite sheet being a multi-layer structure comprising a first air permeable sheet, a second air permeable sheet, and a liquid diffusion fiber sheet and a linear elastic body disposed between the first air permeable sheet and the second air permeable sheet, and
the chassis has stretchability that imparts a pressing force against a wearer.
(2) The disposable garment according to (1), wherein the chassis comprises a front portion, a back portion, and an inside leg portion disposed between the front portion and the back portion, and the chassis has stretchability that imparts a pressing force against a crotch and around a leg of the wearer.
(3) The disposable garment according to (2), wherein the inside leg portion is provided with a plurality of the linear elastic bodies extending from a leg cuff opening on one side toward a leg cuff opening on the other side.
(4) The disposable garment according to (2), wherein the inside leg portion is provided with a plurality of the linear elastic bodies orientated in a direction that joins the front portion and the back portion.
(5) The disposable garment according to any one of (1) to (4), wherein the linear elastic bodies are disposed at an interval of 3.00 to 62.5 mm.
(6) The disposable garment according to any one of (1) to (5), wherein the linear elastic bodies are disposed in contact with the liquid diffusion fiber sheet.
(7) The disposable garment according to any one of (1) to (6), wherein an embossing process is performed on the liquid diffusion fiber sheet.
(8) The disposable garment according to any one of (1) to (7), wherein the liquid diffusion fiber sheet is a sheet made by paper making comprising pulp fiber.
(9) The disposable garment according to (8), wherein the sheet made by paper making is a paper sheet.
(10) The disposable garment according to any one of (1) to (11), wherein the air permeable sheets are a nonwoven fabric and/or a porous sheet.
(11) The disposable garment according to any one of (1) to (10), wherein a joined portion and a non-joined portion are disposed between the first air permeable sheet and the liquid diffusion fiber sheet and/or between the liquid diffusion fiber sheet and the second air permeable sheet.
(12) The disposable garment according to any one of (1) to (11), wherein the stretchable composite sheet is an integral multi-layer structure joined by an adhesive.
(13) The disposable garment according to (12), wherein the adhesive is a hot-melt adhesive, and a portion of the hot-melt adhesive penetrates into the liquid diffusion fiber sheet to form an anchor portion for adhesion.
(14) The disposable garment according to any one of (1) to (13), wherein a portion of the stretchable composite sheet where the linear elastic bodies are disposed has an extensibility of 120 to 500% in a stretching direction of the linear elastic bodies.
(15) The disposable garment according to any one of (1) to (14), wherein a plurality of concaves and convexes are formed in a surface of the stretchable composite sheet along a stretching direction of the elastic bodies.

(16) The disposable garment according to any one of (1) to (15), wherein the torso band comprises a fold on a side proximal to the torso band opening.

(17) The disposable garment according to any one of (1) to (16), wherein a non-gather portion is formed on edges of the leg cuff openings.

(18) The disposable garment according to any one of (1) to (17), wherein a printed layer is formed on a surface of the liquid diffusion fiber sheet.

(19) The disposable garment according to any one of (1) to (18), further comprising an inner sheet disposed between the front portion and the back portion of the chassis.

(20) The disposable garment according to any one of (1) to (19), further comprising an absorbent member comprising an absorbent core, the absorbent member being disposed between the front portion and the back portion of the chassis.

(21) The disposable garment according to (20), wherein the absorbent member is continuously or intermittently joined to the chassis along a line that joins the front portion and the back portion of the chassis.

(22) The disposable garment according to any one of (1) to (21), wherein the front portion and the back portion of the chassis have the same size.

Advantageous Effect of Invention

The disposable garment according to an embodiment of the present invention includes a chassis that is made of a stretchable composite sheet that includes two air permeable sheets such as nonwoven fabrics and a liquid diffusion fiber sheet made of paper and a linear elastic body disposed therebetween. The disposable garment has superior moisture absorbency and quick drying ability, air permeability, moisture permeability, as well as a superior cool contact feeling (cool feeling in a dry state), a superior wet contact cold feeling (minimal stickiness when sweaty), superior fit against the body, and provides a greatly superior feel to the wearer. Diaper embodiments provided with a urine absorbent member have excellent fit against the body. This makes the contact against the body reliable and prevents urine leakage. Additionally, any urine that leaks from the absorbent member is absorbed by the liquid diffusion fiber sheet of the chassis. As a result, leakage can be prevented. The disposable garment according to an embodiment of the present invention can have an appearance that is not inferior to that of typical undergarments, and in diaper embodiments, that they are being worn can be concealed, thus reducing the reluctance of the wearer to wear them.

BRIEF DESCRIPTION OF DRAWINGS

FIGS. 15A to 15J are diagrams for explaining variations of the elastic sheet 17.

FIGS. 16A to 16H are diagrams for explaining variations of the elastic sheet 17.

FIGS. 23A to 23F illustrate variations of how the elastic sheet 17 is attached.

FIGS. 26A to 26H illustrate other variations of how the elastic sheet 17 is attached.

FIGS. 35A to 35H illustrates other variations of the elastic sheet 17.

DESCRIPTION OF EMBODIMENTS

Below, disposable garments according embodiments of the present invention are described in details with reference to the drawings.

In the present invention, "disposable garment" refers to a single-use product as well as products that can withstand a short period of usage and several washing cycles.

There are no age restrictions on who can wear the disposable garment of the present specification, and the disposable garment may be worn by both adults and children. The wearer is also not limited to any one gender, and the disposable garment may be worn by both males and females. Furthermore, the wearer is not limited to humans, and the disposable garment may be for pets such as dogs and cats.

The disposable garment of the present specification is not limited to having the object of absorbing urine, and the object may include absorbing any other body wastes or menstrual blood of women.

In the present specification, "absorb" refers to absorbing urine as well as menstrual blood of women, absorbing bodily fluids such as sweat, and absorbing other body wastes.

Figure 1:
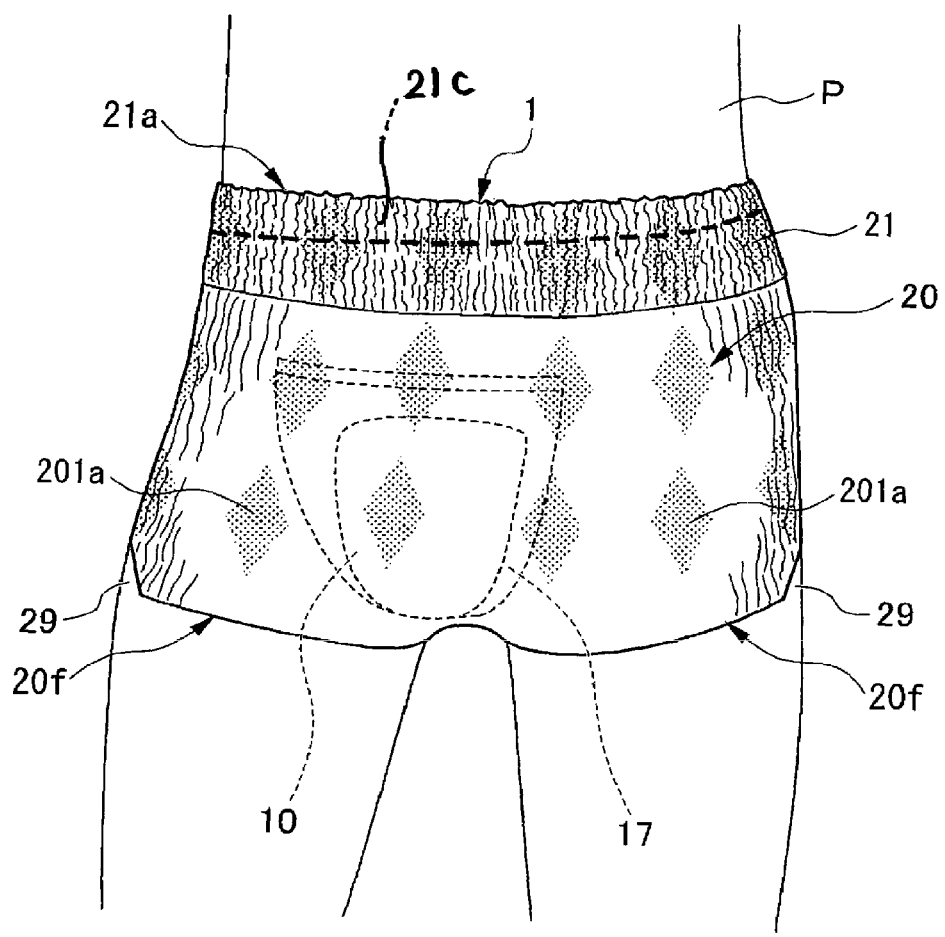
FIG. 1 is a diagram illustrating a disposable garment 1 worn by a wearer P.
Figure 2:
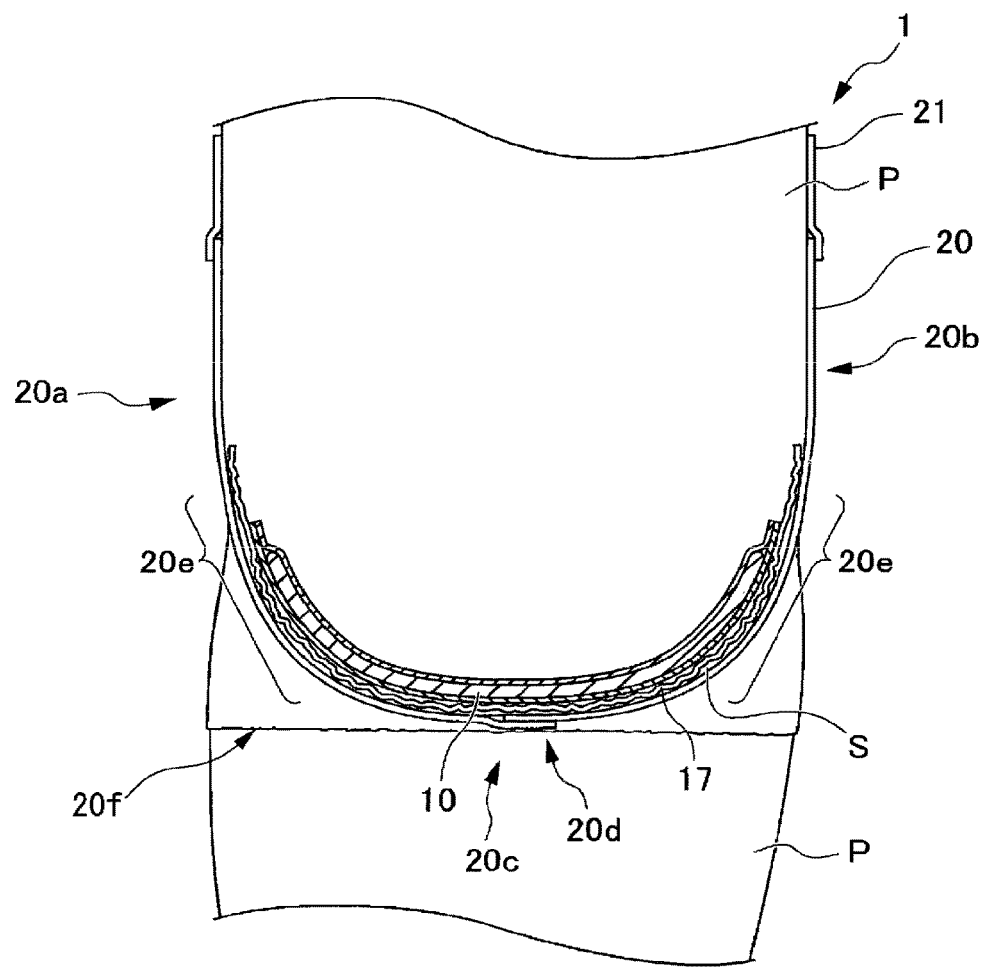
FIG. 2 is a cross-sectional view of the disposable garment 1.

FIG. 1 is a diagram illustrating a disposable garment 1 according to a first embodiment of the present invention being worn by a wearer P. FIG. 2 is a vertical cross-sectional view of the disposable garment 1.

In the present specification, when describing the disposable garment 1, the up/down direction of the disposable garment 1 when the wearer P wears the disposable garment 1 is defined as the vertical direction, the left/right direction is defined as the lateral direction of the disposable garment 1, and the front/back direction of the wearer is defined as the front/back direction.

As illustrated in FIGS. 1 and 2, the disposable garment 1 includes a torso band 21 that is worn around the waist of the wearer P and a chassis 20. The chassis 20 includes a front portion 20a, a back portion 20b, an inside leg portion 20c disposed between the front portion 20a and the back portion 20b, and left and right leg cuff openings 20f. An elastic sheet 17 is disposed on the inner side of the inside leg portion 20c of the chassis 20 extending from the front portion 20a to the back portion 20b. An absorbent member 10 is disposed on the inner side of the elastic sheet 17 (on the side proximal to the wearer). No gathers like those of conventional diapers are disposed on the leg cuff openings 20f of the chassis 20, making these portions non-gather portions.

Inside Leg Portion

As illustrated in FIG. 2, the inside leg portion 20c may include a detachable join portion 20d. The join portion 20d may be made of a surface fastener, a hook, a button, an adhesive sheet, an adhesive, or the like. For example, in embodiments in which the join portion 20d is a surface fastener, the wearer can bring together the joining surfaces of the surface fastener to join the inside leg portion 20c as illustrated in FIG. 2 and detach the joining surfaces of the surface fastener to free the inside leg portion 20c. The join portion 20d may have a configuration in which the join portion 20d can only be freed. For example, the inside leg portion 20c may be sewn together or joined by hot melt adhesive, thermal sealing, or ultrasonic bonding, and the joint can be broken if necessary to free the inside leg portion 20c. In an alternative configuration, a portion of the inside leg portion 20c is lined with a tear line (perforated line), and the tear line can be broken if necessary to free the inside leg portion 20c. By freeing the inside leg portion 20c, the chassis 20 can be made into the shape of a tube top (see FIG. 46). In some embodiments, the inside leg portion 20c may not include a detachable or freeable join portion 20d. Additionally, the inside leg portion 20c may have a configuration in which the front portion 20a and the back portion 20b are attached in a freely detachable manner.

Chassis

As illustrated in FIG. 1, the chassis 20 has substantially the same shape as typical pants-type undergarments or garments such as trunks as well as having a similar length. The chassis 20 is provided with slits 29 on both sides. Providing the slits 29 facilitates movement of the legs of the wearer P. The chassis 20 is not limited to the configuration of the present embodiment, and the chassis 20 may have a shape that covers the wearer P above the waist. The chassis 20 may also cover only below the hip bone. Additionally, for women, the sides may be cut further up than that illustrated in FIG. 1 (in other words, form a substantially V-shape in a front view) to further facilitate movement of the legs.

The front portion 20a and the back portion 20b of the chassis 20 may have the same or different sizes. By making the back portion 20b of the chassis 20 larger than the front portion 20a, a disposable garment 1 can be provided that wearers with large buttocks can easily wear. Additionally, in embodiments in which the front portion 20a and the back portion 20b have different sizes, the disposable garment 1 can be draped so that the disposable garment 1 provided can be tailored to fit wearers of various body shapes.

Stretchable Composite Sheet

Figure 4:
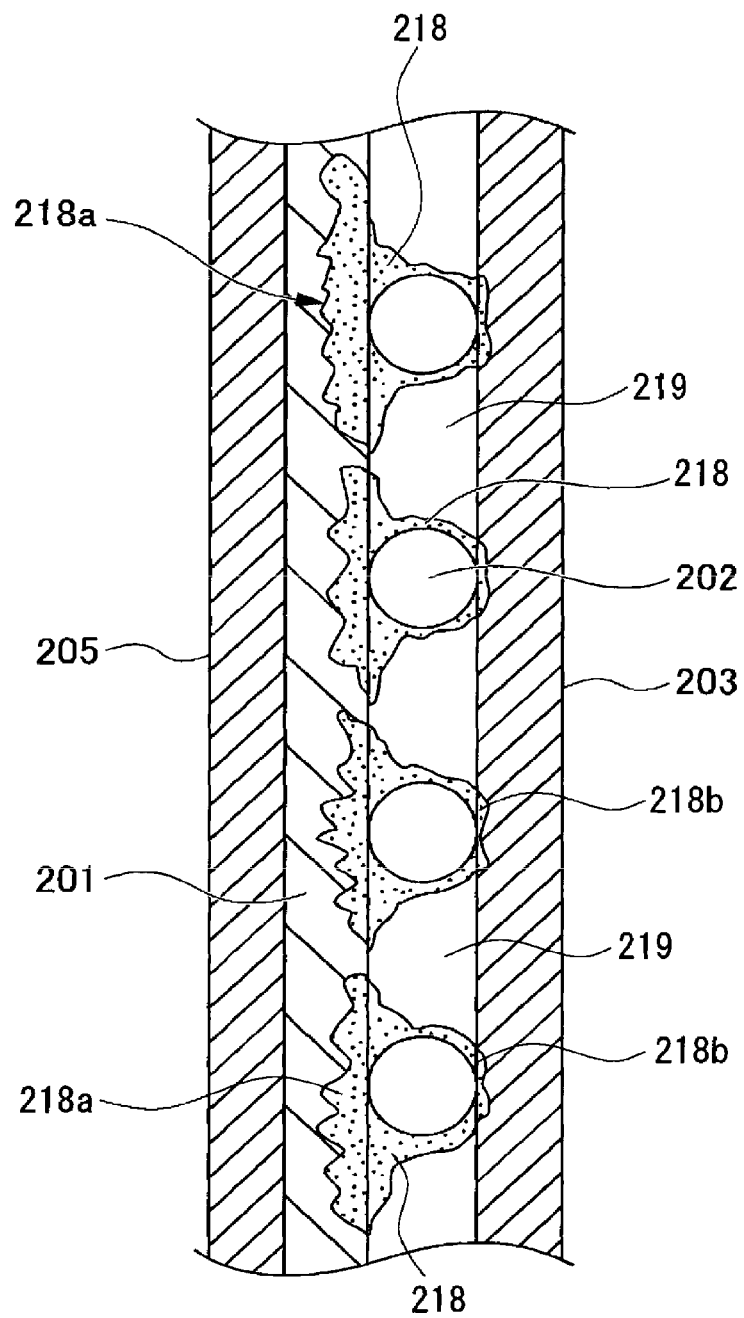
FIG. 4 is a diagram for explaining an anchor portion formed on a liquid diffusion fiber sheet 201.

As illustrated in FIG. 4, at least the chassis 20 of the disposable garment 1 is made of a stretchable composite sheet that includes a liquid diffusion fiber sheet 201 and a linear elastic body 202 layered together and disposed between a first air permeable sheet 203 and a second air permeable sheet 205. The stretchable composite sheet provides stretchability that imparts a pressing force against the crotch, in particular, an upper crotch region 20e disposed in the region above the inside leg portion 20c and around the legs. The portion of the stretchable composite sheet where the linear elastic body 202 is disposed preferably has an extensibility of 120 to 500% in the stretching direction of the linear elastic body 202.

Torso Band

The torso band 21 is the portion that is worn around the waist of the wearer P and is disposed on the upper portion of the chassis 20. A torso band opening 21a is formed on the upper end side of the torso band 21. The torso band 21 is preferably made from a material with stretchability. The torso band 21 can be an integral member with the chassis 20 and be made from the stretchable composite sheet, or the torso band 21 can be formed as a separate member from different material than that of the chassis 20. The torso band 21 preferably has stretchability in the direction around the torso so that the fit of the disposable garment 1 for the wearer is improved. The torso band 21 may have folds 21c on the torso band opening 21a side where the torso band 21 is folded inward (see FIG. 1 and FIG. 26H).

Air Permeable Sheet

Examples of the air permeable sheets 203, 205 that compose the stretchable composite sheet include nonwoven fabrics, porous sheets, and multi-layered structures thereof. Examples of a suitable nonwoven fabric include spunbonded nonwoven fabric, thermally bonded nonwoven fabric, spunlaced nonwoven fabric, dry nonwoven fabric, wet nonwoven fabric, melt-blown nonwoven fabric, chemically bonded nonwoven fabric, needle punched nonwoven fabric, stitch bonded nonwoven fabric, and steam jet nonwoven fabric. Among these, spunbonded nonwoven fabric, thermally bonded nonwoven fabric, and spunlaced nonwoven fabric are more preferable. Examples of the fiber that composes the nonwoven fabric include natural fibers such as animal fiber, synthetic fibers such as nylon fiber, acrylic fiber, polyolefin fiber, polyethylene terephthalate fiber, and regenerated fibers such as rayon. Synthetic fibers and regenerated fibers are preferable. Examples of a porous sheet include a sheet including a plurality of micropores provided on a film made of synthetic resin such as polyethylene. The air permeable sheets 203, 205 preferably have a weight (basis weight) per unit area of 5 to 40 g/m$^2$. The air permeable sheets 203, 205 may have the same or different material and basis weight. A suitable material for the air permeable sheets 203, 205 can be selected as appropriate according to the position where they are disposed. For example, in configurations in which the air permeable sheet is provided on the outer side of the garment 1, a material with high impermeability to water is preferable, and a nonwoven fabric or a porous sheet treated for water repellency is preferable. In configurations in which the air permeable sheet is provided on the side proximal to the skin of the wearer, a material similar to that used for the air permeable sheet provided on the outer side with high impermeability to water may be used, or a sheet with good moisture permeability and water permeability may be used. A nonwoven fabric is particularly preferably used as the material for the air permeable sheet because an air permeable sheet with good air permeability, moisture permeability, and high impermeability to water due to water repellency treatment can be produced.

Liquid Diffusion Fiber Sheet

Examples of the liquid diffusion fiber sheet 201 include a sheet made by paper making that contains a natural fiber such as pulp. The amount of pulp in the liquid diffusion fiber sheet 201 is preferably 30% or more, and more preferably 50% or more. The amount of pulp is even more preferably 80% or more. By the amount of pulp being as described above, the flexibility of the stretchable composite sheet as a whole can be increased and production efficiency during manufacture can be increased. Furthermore, the more the amount of pulp is increased, the easier the disposed product can decompose in the earth. Thus, the environmental burden can be further reduced and the environmental friendliness can be improved. The liquid diffusion fiber sheet 201 is preferably a sheet made by paper making using a slurry containing a fiber such as pulp, and more preferably a paper sheet. In configurations in which the liquid diffusion fiber sheet 201 is a paper sheet, the liquid diffusion fiber sheet 201 may be treated by at least one of hydrophobic processing, water repellency processing, waterproofing processing, water resistant processing. The liquid diffusion fiber sheet 201 is preferably made of a single layer but may have a multi-layer configuration. In configurations in which the liquid diffusion fiber sheet 201 is made of a plurality of fibrous sheets, the fibrous sheets may have the same thickness and be of the same material, or two or more types of fibrous sheets of different materials may be used. The liquid diffusion fiber sheet 201 preferably has a weight per unit area of 5 to 40 g/m$^2$.

The hardness of the liquid diffusion fiber sheet 201 can be set as desired according to the thickness and material of the liquid diffusion fiber sheet 201. Thus, by using a technique to vary the thickness across the liquid diffusion fiber sheet 201, a disposable garment 1 with a three-dimensional design can be produced. By using such a technique, for example, a disposable garment 1 with a design like that of shaping undergarments can be produced. This allows a disposable garment 1 to be provided which can hide the body line or shape the body line to appear beautiful. Additionally, by making the liquid diffusion fiber sheet 201 harder in some regions such as at the end portion of the chassis 20, a disposable garment 1 with a feel like that of typical garments can be produced. By making the liquid diffusion fiber sheet 201 thicker and thus harder in some regions, the liquid diffusion fiber sheet 201 can be made resistant to sagging. At such hardened regions of the liquid diffusion fiber sheet 201, more gaps are formed between it and the body of the wearer. This allows air permeability to be improved. On the other hand, by lessening the thickness of the liquid diffusion fiber sheet 201, the liquid diffusion fiber sheet 201 becomes susceptible to sagging and the disposable garment 1 can be made softer as a whole or in some regions.

Pulp

Examples of the pulp used in the liquid diffusion fiber sheet 201 include wood pulp, synthetic pulp, and waste paper pulp. Additionally, the pulp is not limited to containing only a natural fiber, and can contain a regenerated fiber such as rayon. Furthermore, the raw material pulp can be toilet paper material. In such configurations, for example, the raw material pulp can contain a bleached softwood kraft pulp obtained from softwood, such as red pine, Yezo spruce, Sakhalin fir, Douglas fir, hemlock, and spruce, and a bleached hardwood kraft pulp obtained from hardwood, such as beech, Japanese oak, birch, eucalyptus, oak, poplar, and alder, blended at a predetermined ratio. The liquid diffusion fiber sheet 201 is preferably made of only a natural fiber. Examples of a natural fiber that can be used other than pulp include kenaf, bamboo fiber, straw, cotton, cocoon filament, and sugarcane. In configurations in which the liquid diffusion fiber sheet 201 is a paper sheet, the paper sheet may be water dispersible or not, but a water dispersible paper sheet is preferable. The fiber used in the liquid diffusion fiber sheet 201 may be a staple fiber or a filament fiber or a combination thereof.

Softener

By the liquid diffusion fiber sheet 201 containing a softener, the stretchability can be improved. For example, a multi-layered structure that includes an elastic body but not a liquid diffusion fiber sheet between air permeable sheets made of a nonwoven fabric has stretchability but lacks in air permeability, moisture permeability, flexibility, and absorbency and quick drying ability performance. However, a stretchable composite sheet with a liquid diffusion fiber sheet and an elastic body disposed in a layered manner between air permeable sheets has improved hygroscopicity, air permeability, moisture permeability, flexibility, and absorbency and quick drying ability. Furthermore, the liquid diffusion fiber sheet 201 containing a softener has further improved flexibility as well as improved absorbency, moisture permeability, and even stretchability.

Linear Elastic Body

Figure 62A:
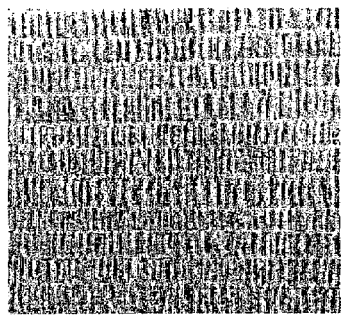
FIGS. 62A and 62B illustrate lines on the surface of the stretchable composite sheet.
Figure 62B:

The linear elastic body 202 is preferably provided throughout the entire stretchable composite sheet to provide the chassis 20 with stretchability that imparts a pressing force against the wearer P. With the linear elastic body 202 being disposed in the inside leg portion 20c, when the wearer P wears the garment, the leg cuff opening 20f stretches in the width direction and the inside leg portion stretches in the width direction. This has the result of raising the inside leg portion and imparting a pressing force on the crotch region and around the legs of the wearer. The linear elastic body 202 is a thread-like member made of an elastic material such as an elastomer or a rubber. Examples of an elastomer include styrene based elastomers, olefin based elastomers, urethane based elastomers, polyester based elastomers, butadiene based elastomers, vinyl chloride based elastomers, and silicone based elastomers. Examples of a rubber include natural rubber, styrene-butadiene rubber, butadiene rubber, chloroprene rubber, isoprene rubber, silicone rubber, fluororubber, acrylic rubber, and urethane rubber. In the inside leg portion 20c, a plurality of the linear elastic bodies 202 are preferably disposed extending from one leg cuff opening 20f toward the other leg cuff opening 20f of the inside leg portion 20c or disposed in a direction that joins the front portion 20a and the back portion 20b of the chassis 20. The linear elastic bodies 202 are preferably disposed at intervals of 2.00 to 7.00 mm, and more preferably at intervals of 3.00 to 6.25 mm. By the linear elastic bodies 202 being disposed at intervals of 3.00 to 6.25 mm, as illustrated in FIG. 62A, orderly arranged fine lines are formed and the thickness is fixed. This enhances the appearance of the garment and improves the skin comfort. Additionally, because the surface area is further increased, the absorbency and quick drying ability with respect to sweat is improved. If the intervals of the linear elastic bodies 202 are greater than 6.25 mm, as illustrated in FIG. 62B, meandering lines are formed and the thickness is not fixed. As illustrated in FIG. 4, the linear elastic bodies 202 are preferably disposed at positions in contact with the liquid diffusion fiber sheet 201. A suitable strength and material of the linear elastic bodies 202 can be selected as appropriate according to the position where the linear elastic bodies 202 are disposed. For example, the linear elastic bodies 202 in the front portion 20a and the back portion 20b of the chassis 20 may have different strength and materials. When the strength and materials of the linear elastic bodies 202 in the front portion 20a and the back portion 20b of the chassis 20 are the same, the shape of the chassis 20 is susceptible to restrictions. When the strength and the materials of the linear elastic bodies 202 in the front portion 20a and the back portion 20b of the chassis 20 are different, the degree of freedom the shape can have is increased. Accordingly, for example, the chassis 20 can be given a three-dimensional shape.

Stretchable Composite Sheet Joining Method

The air permeable sheets 203, 205, the liquid diffusion fiber sheet 201, and the linear elastic bodies 202 of the stretchable composite sheet are formed as an integral multi-layered structure via adhesive bonding, heat sealing, or ultrasonic bonding, with adhesive bonding being preferable. Examples of an adhesive include emulsion adhesives, pressure sensitive adhesives, and hot-melt adhesives, with hot-melt adhesives being preferable. In forming the integral multi-layered structure of the air permeable sheets 203, 205, the liquid diffusion fiber sheet 201, and the linear elastic bodies 202, the adhesive may be applied covering the entire surface of the air permeable sheets 203, 205 and the liquid diffusion fiber sheet 201, or the adhesive may be applied partially, forming non-join portions. As illustrated in FIG. 4, an adhesive 218 is applied on the surface of the linear elastic bodies 202 to adhere together the air permeable sheet 203 and the liquid diffusion fiber sheet 201 via the linear elastic bodies 202, the adhesive 218 forming a stripe-like pattern, a grid-like pattern, or a dotted pattern. This forms joined portions where the air permeable sheet 203 and the liquid diffusion fiber sheet 201 are adhered together via the adhesive 218 and non-joined portions 219 where they are not. Additionally, in adhering together the air permeable sheet 205 and the liquid diffusion fiber sheet 201, the adhesive is applied and formed in a stripe-like pattern, grid-like pattern, or a dotted pattern. This forms joined portions where the air permeable sheet 205 and the liquid diffusion fiber sheet 201 are adhered together and non-joined portions. By forming non-joined portions between the air permeable sheet 205 and the liquid diffusion fiber sheet 201 and between the air permeable sheet 203 and the liquid diffusion fiber sheet 201, the air permeability and the moisture permeability of the stretchable composite sheet can be further improved and the flexibility and skin comfort are improved. Hot-melt adhesive has high water repellency. Thus, when the hot-melt adhesive is used to adhere together the air permeable sheets 203, 205 and the liquid diffusion fiber sheet 201 by being applied covering the entire surfaces thereof, air permeability, moisture permeability, and flexibility may decrease. However, by applying the hot-melt adhesive intermittently to form non-joined portions, a superior air permeability, moisture permeability, and flexibility can be maintained. Additionally, by decreasing the amount of adhesive used, cost reduction can be achieved and the disposal of a used disposable garment 1 can have reduced impact on the environment.

Adhesive

The adhesive used in adhering is not particularly limited. Examples of an adhesive that can be suitably used in adhering include known adhesives such as adhesives based on EVA (ethylene-vinyl acetate copolymer), PO (polyolefins), PA (polyamides), SR (synthetic rubber), ACR (acryl), and PUR (moisture curable polyurethane). These adhesives can be used individually or in combination of two or more. Furthermore, adhesives other than these may also be used in combination. The liquid diffusion fiber sheet 201 is highly permeable to a hot-melt adhesive. Thus, the adhesive easily penetrates into the liquid diffusion fiber sheet 201. As illustrated in FIG. 4, a portion of the adhesive 218 penetrates into the gaps between the fibers of the liquid diffusion fiber sheet 201, and the adhesive and the fibers combine to form anchor portions 218a. FIG. 4 illustrates a configuration in which the air permeable sheet 203 and the liquid diffusion fiber sheet 201 are adhered together with the linear elastic bodies 202 disposed therebetween. The adhesive 218 is applied on the surface of the linear elastic bodies 202. The air permeable sheet 203 is a nonwoven fabric or a porous sheet and has less liquid diffusibility than the liquid diffusion fiber sheet 201 which is a paper sheet for example. Thus, an anchor portion 218b that penetrates the air permeable sheet 203 is smaller than an anchor portion 218a formed by the adhesive that penetrates the liquid diffusion fiber sheet 201. The formed anchor portions 218a, 218b improve the adhesive strength and the overall strength of the stretchable composite sheet. The anchor portion 218b may also not be formed in the air permeable sheet 203. In configurations in which the air permeable sheet 203, the linear elastic bodies 202, and the liquid diffusion fiber sheet 201 are joined integrally together by the adhesive 218 applied to the surface of the linear elastic bodies 202, the anchor portion 218a is preferably formed in the liquid diffusion fiber sheet 201. By the adhesive 218 applied on the surface of the linear elastic bodies 202 penetrating into the liquid diffusion fiber sheet 201 to form the anchor portion 218a, the linear elastic bodies 202 are supported and adhered reliably and firmly between the air permeable sheet 203 and the liquid diffusion fiber sheet 201. Additionally, the strength of the liquid diffusion fiber sheet 201 can be improved. In configurations in which the liquid diffusion fiber sheet 201 is not disposed and the linear elastic bodies 202 are disposed between the air permeable sheets 203, 205, a large amount of the adhesive 218 is needed to obtain an appropriate adhesive strength. However, applying a large amount of an adhesive causes the linear elastic bodies 202 to lose elastic force as well as reduces the flexibility of the chassis 20. This reduces the skin comfort. Additionally, the adhesive may ooze out from the air permeable sheet disposed on the side proximal to the body causing the appearance to be blemished. In configurations in which the liquid diffusion fiber sheet 201 is further disposed between the air permeable sheets 203, 205 and the linear elastic bodies 202 are disposed in contact with the liquid diffusion fiber sheet 201, the adhesive 218 has a higher affinity with the liquid diffusion fiber sheet 201 than the air permeable sheets 203, 205 and the holding power of the liquid diffusion fiber sheet 201 of the linear elastic bodies 202 is greater than the holding power of the air permeable sheets 203, 205 of the linear elastic bodies 202. Thus, the linear elastic bodies 202 can be reliably held within the composite sheet. In particular, the adhesive 218 applied to the surfaces of the linear elastic bodies 202 penetrates into the liquid diffusion fiber sheet 201 and joins integrally with the fibers therein to form the anchor portion 218a. This allows a strong adhesive strength to be obtained using only a small amount of hot-melt adhesive. Accordingly, by not using a large amount of hot-melt adhesive, the linear elastic bodies 202 do not lose elastic force and the holding power of the linear elastic bodies 202 in the stretchable composite sheet is further improved. Additionally, the flexibility of the chassis 20 is increased and the hot-melt adhesive is prevented from oozing out from the air permeable sheet 203 disposed on the side proximal to the body. This allows the skin comfort to be improved and the appearance to be further improved. Furthermore, when the stretchable composite sheet is cut, the linear elastic bodies 202 are reliably supported even at the cut end portion. This prevents the linear elastic bodies 202 coming loose at the cut end portion and the end portions of the linear elastic bodies 202 receding into the sheet to form a portion where the linear elastic bodies 202 are not present. Additionally, the anchor portion 218a formed in the liquid diffusion fiber sheet 201 makes the liquid diffusion fiber sheet 201 resilient to breakage even when the liquid diffusion fiber sheet 201 made of a paper sheet is exposed to water. Furthermore, by reducing the amount of hot-melt adhesive used, cost reduction can be achieved. Additionally, decreasing the amount of adhesive used decreases the impact on the environment when the disposable garment 1 is disposed of after use. Decreasing the amount of hot-melt adhesive used can also improve the air permeability and the absorbency and quick drying ability for sweat of the chassis 20.

Embossing Process

Figure 5:
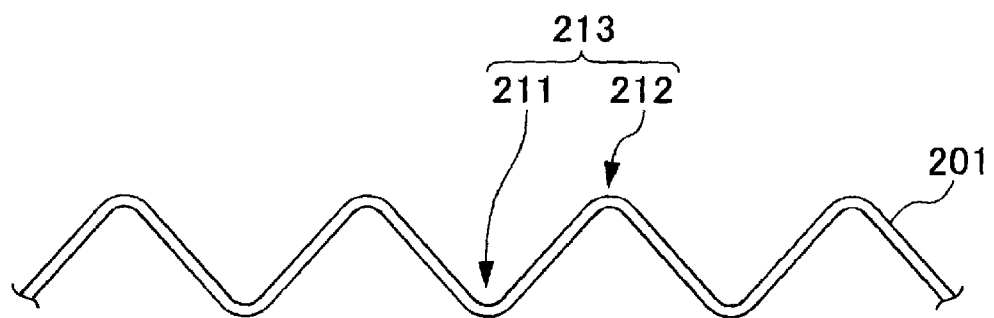
FIG. 5 is a cross-sectional view of a portion of an example of the liquid diffusion fiber sheet 201 formed with concave and convex portions 213.

The liquid diffusion fiber sheet 201 preferably undergoes an embossing process. FIG. 5 illustrates an example of the liquid diffusion fiber sheet 201 in which concave and convex portions 213 are formed. The concave and convex portions 213 include concave portions 211 and convex portions 212 embossed together. The concave portions 211 and the convex portions 212 are formed on the entire surface of the liquid diffusion fiber sheet 201 by an embossing process using embossing rolls, for example. The embossing can include pressing the liquid diffusion fiber sheet via a pair of embossing rolls provided with projections on the surface thereof. Additionally, the cross-sectional shape of the concave and convex portion 213 formed by the embossing is not limited to the wave-like shape illustrated in FIG. 5, and may be triangular, quadrilateral, or semi-circular. By forming the concave and convex portions 213 on the surface of the liquid diffusion fiber sheet 201, a bulky liquid diffusion fiber sheet 201 can be achieved. The method of forming the concave and convex portions 213 on the surface of the liquid diffusion fiber sheet 201 is not limited to embossing using an embossing roll, and other methods may be used.

The concave and convex portions 213 formed using an embossing process are not limited to having the concave and convex shape illustrated in FIG. 5 and may have only concaves or only convexes. In other words, a non-flat portion is not limited to the given example of the concave and convex portion 213, and shapes that provide an equivalent function may also be used. Additionally, other configurations may include at least one flat portion or be flat overall. Compared to a non-embossed liquid diffusion fiber sheet 201, an embossed liquid diffusion fiber sheet 201 has less strength and includes a weakened portion. The embossing process is not limited to one in which the concave and convex portion 213 is formed on the surface of the liquid diffusion fiber sheet 201. In other embodiments, the embossing process may include pressing of the liquid diffusion fiber sheet 201 by a flat roll without any projections on the surface thereof, or using a combination of a pair of embossing rolls provided with projections on the surface thereof and a flat roll without projections on the surface thereof. Embossing is not limited to being performed only once and may be performed multiple times.

Figure 6:
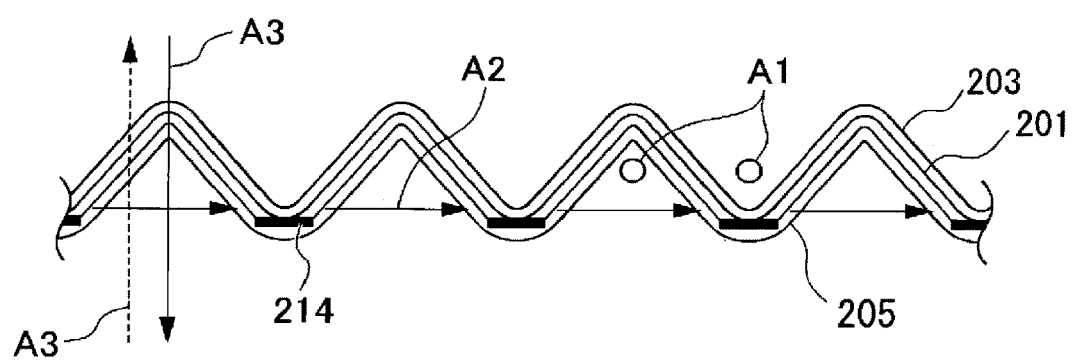
FIG. 6 is a diagram for explaining the flow of air in the embossed liquid diffusion fiber sheet 201.

FIG. 6 illustrates an example of a multi-layered structure including the embossed liquid diffusion fiber sheet 201 and the air permeable sheets 203, 205, the sheets being adhered together. As illustrated in FIG. 6, the flow of air A1 passes through the inner side of the air permeable sheet 205. In a second pattern, air A2 passes alternately through the air permeable sheet 203, the liquid diffusion fiber sheet 201, and the air permeable sheet 205. An adhesive material 214 that adheres together the liquid diffusion fiber sheet 201 and the air permeable sheet 205 may be partially applied between the liquid diffusion fiber sheet 201 and the air permeable sheet 205. This allows the air A2 to pass through the spaces between the liquid diffusion fiber sheet 201 and the air permeable sheet 205 where the adhesive material 214 is not applied. In a third pattern, air A3 passes through the air permeable sheet 203, the liquid diffusion fiber sheet 201, and the air permeable sheet 205 in that order.

In the third pattern, the air A3 can passes through the air permeable sheet 205, the liquid diffusion fiber sheet 201, and the air permeable sheet 203 in this order as illustrated by the dashed line in the same drawing. Also, how the air flows is not limited to the three patterns described above and it can be appreciated that a variety of configurations are possible. For example, the air can flow in a manner so as to cross the concave and convex portion 213.

Figure 7:
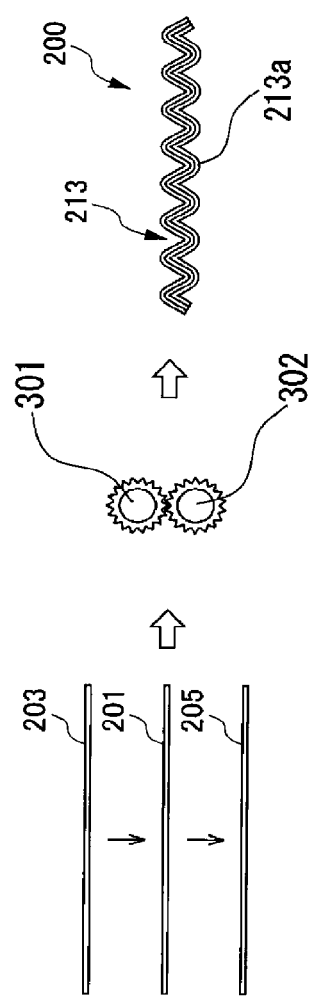
FIG. 7 illustrates a variation of the embossing process on the liquid diffusion fiber sheet 201.
Figure 8:
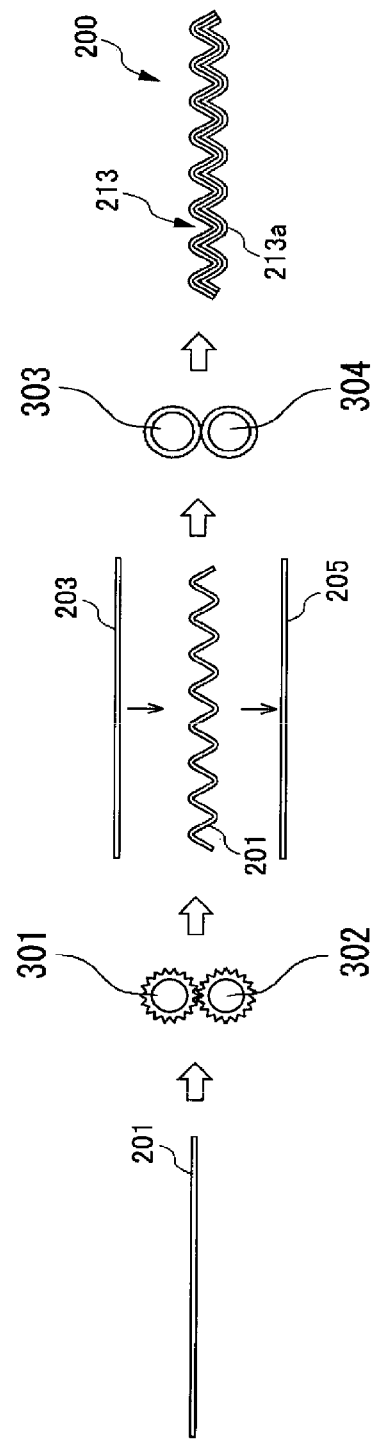
FIG. 8 illustrates a variation of the embossing process on the liquid diffusion fiber sheet 201.

The embossing process is not limited to being performed on only the liquid diffusion fiber sheet 201, and embossing can be performed after the liquid diffusion fiber sheet 201 is joined together with one or more of the air permeable sheets 203, 205, and the linear elastic bodies 202 or joined together with all thereof. FIGS. 7 and 8 illustrate examples of a method of producing a stretchable composite sheet. In the method illustrated in FIG. 7, the air permeable sheet 203, the liquid diffusion fiber sheet 201, the air permeable sheet 205, and the linear elastic bodies 202 (not illustrated) are formed as an integral multi-layered structure in a stretched state. Thereafter, the multi-layer structure is embossed by being passed through a pair of embossing rolls 301, 302 and the embossed composite sheet is obtained. After the multi-layered structure is passed through the embossing rolls 301, 302, the linear elastic bodies 202 are released from tension and a stretchable composite sheet 200 is obtained in which lines 213a including the concave and convex portions 213 are formed. FIG. 8 illustrates another method of producing a composite sheet. The method includes passing the liquid diffusion fiber sheet 201 through the pair of embossing rolls 301, 302 with projections provided on the surface thereof. Thereafter, the air permeable sheets 203, 205 and the linear elastic bodies 202 with the adhesive applied (not illustrated) are layered on top of each other in a stretched state. This multi-layer structure is then passed through a pair of flat rolls 303, 304 to form an integrated multi-layered composite sheet. After the multi-layered structure is passed through the flat rolls 303, 304, the linear elastic bodies 202 are released from tension and the stretchable composite sheet 200 is obtained in which the lines 213a including the concave and convex portions 213 are formed. It can be appreciated that the lines 213a in the composite sheet 200 can be easily formed by embossing the liquid diffusion fiber sheet 201 to form a weakened portion therein, and can be formed by removing the tension of the linear elastic bodies 202 to produce a restoring force that urges the linear elastic bodies 202 to return to their original state. Additionally, forming a weakened portion in the liquid diffusion fiber sheet 201 makes the elastic force of the linear elastic bodies 202 more resilient to being reduced, and the lines 213a originating at the weakened portions easier to form. The lines 213a are formed aligned with the stretching direction of the linear elastic bodies 202. The composite sheet may be partially provided with the lines 213a, but the lines 213a are preferably formed on the entire composite sheet. The chassis 20 including the stretchable composite sheet 200 with such fine lines 213a has a smaller contact surface area and thus skin comfort is enhanced. Additionally, by forming the fine lines 213a, light absorbency is increased and transparency is reduced, making it easier to hide the lines of the body of the wearer. By forming such lines 213a, multiple gaps are formed inside the stretchable composite sheet. The chassis 20 including the stretchable composite sheet 200 with such lines 213a has further improved air permeability. The number of concave and convex portions 213 formed continuously in the liquid diffusion fiber sheet 201 is preferably 15 to 50 per 1 cm, for example.

The stretchable composite sheet 200 includes the liquid diffusion fiber sheet 201 disposed between the air permeable sheets 203, 205 and thus has superior intrinsic air permeability. By forming the non-joined portion 219 by partially applying the adhesive when the sheets and the linear elastic bodies 202 are formed as an integral multi-layered structure, the flow of air can be increased. This further increases air permeability. Furthermore, the concave and convex portions 213 of the liquid diffusion fiber sheet 201 and the fine lines 213a on the surface of the stretchable composite sheet 200 facilitate the flow of air by allowing air to flow through the spaces in the concave and convex portions 213 and the lines 213a. This further improves air permeability. By forming the fine lines 213a on the surface of the stretchable composite sheet 200, the area in contact with the skin is decreased. This increases the skin comfort. Also, by increasing the surface area of the stretchable composite sheet 200, the absorbency for urine and the like is improved and absorbency and quick drying ability is improved. The fine lines 213a formed on the surface of the stretchable composite sheet 200 result in reduced transparency.

Holes, slits, and notches of a suitable size can be formed in the surface of the liquid diffusion fiber sheet 201 by performing a hole forming process such as stamping and punching using an embossing roll on the liquid diffusion fiber sheet 201. Such a process may be performed on the liquid diffusion fiber sheet 201 only or on all of the stretchable composite sheet. By performing a hole forming process or the embossing process described above on the liquid diffusion fiber sheet 201, the chassis 20 can be provided with further flexibility and a superior feeling of volume and softness.

The disposable garment 1 may have printing on the torso band 21 and the chassis 20 as illustrated in the example in FIG. 1. Printing on the liquid diffusion fiber sheet 201 made of a paper sheet results in a more vibrant picture than when on the air permeable sheets 203, 205 made of a nonwoven fabric, thus in configurations in which printing is performed, a printed layer 201a is preferably formed on the surface of the liquid diffusion fiber sheet 201 as illustrated in FIGS. 3A to 3D. By printing the surface of the disposable garment 1 with beautiful colors, patterns, or pictures (hereafter, referred to as pictures), reluctance of the wearer P to wear the disposable garment 1 can be further reduced.

The printed layer 201a can be, for example, formed by inkjet printing. The surface of the printed layer 201a is preferably subjected to a discoloration prevention process, such as varnishing or application of a binder. Examples of a binder include known materials such as PVA, CMC, EVA, acryl, and lacquer. An ink subjected to a discoloration preventing process can be also used.

In configurations in which the liquid diffusion fiber sheet 201 is thin, the printed layer 201a is preferably formed by flexographic printing. In flexographic printing, the contact surface between the plate and the liquid diffusion fiber sheet 201 is small, and the printing pressure applied on the contact surface is low because the flexographic printing utilizes a relief plate. Because of this, the liquid diffusion fiber sheet 201 is easily released from the plate. Thus, flexographic printing is suitable for forming the printed layer 201a on a thin liquid diffusion fiber sheet 201.

Furthermore, a large number of various types of ink can be used in the flexographic printing. This means that it is less restricted in terms of the ink viscosity than ink-jet printing, for example, in which the ink is discharged through a nozzle. Accordingly, in configurations in which the printed layer 201a is formed by flexographic printing, the degree of freedom of the picture able to be printed is increased. In configurations in which a picture is printed on the printed layer 201a, the picture printed by the plate may be stretched in the stretching direction of the linear elastic bodies 202 so that when the disposable garment 1 is worn by the wearer, the picture has the desired shape on the surface. Specifically, if the size of the complete picture is 100% when the linear elastic bodies 202 are not stretched, the picture of the printing plate is preferably formed at a proportion 110 to 350% in the stretching direction of the linear elastic bodies 202. This ensures the picture is not unnaturally enlarged when the disposable garment 1 is worn by the wearer, thus making the disposable garment 1a more visually appealing product.

In configurations in which the printed layer 201a is formed on the liquid diffusion fiber sheet 201, the printed layer 201a may be formed on the liquid diffusion fiber sheet 201 prior to the embossing process or may be formed after the embossing process. Embossing can form the shape of a plurality of concave portions and convex portions on the surface of the liquid diffusion fiber sheet 201. This makes possible three-dimensional designs, designs that differ depending on the angle of view, and other designs that are unable to be displayed with normal printing.

FIGS. 3A to 3D illustrate variations of the chassis 20.

Figure 3:
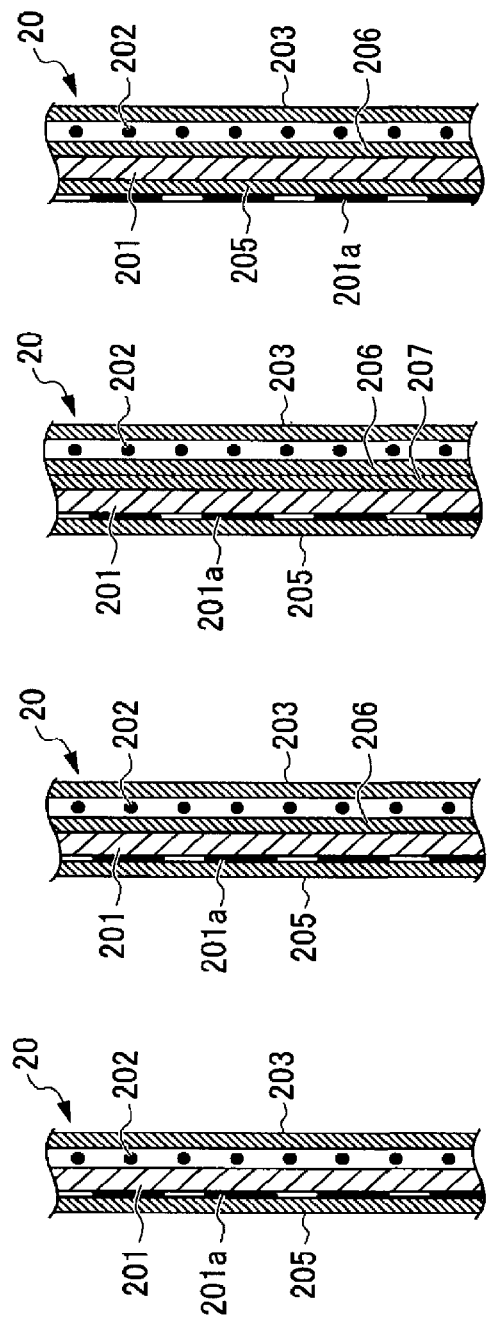
FIGS. 3A to 3D illustrate variations of a chassis 20.

In FIG. 3A, the air permeable sheet 205 is disposed on the outer side of the liquid diffusion fiber sheet 201, and the printed layer 201a is disposed between the liquid diffusion fiber sheet 201 and the air permeable sheet 205.

In FIG. 3B, an air permeable sheet 206 is further disposed between the liquid diffusion fiber sheet 201 and the linear elastic bodies 202.

In FIG. 3C, an air permeable sheet 207 is further disposed between the liquid diffusion fiber sheet 201 and the air permeable sheet 206.

In the configurations of FIGS. 3A to 3C described above, in reference to the liquid diffusion fiber sheet 201, the air permeable sheet 205 is disposed on the outer side of the printed layer 201a. This prevents the picture of the printed layer 201a from being removed by friction or fading.

In FIG. 3D, the printed layer 201a is formed on the surface of the air permeable sheet 205. In this configuration, the picture of the printed layer 201a appears to stand out. Thus, in comparison to a configuration without the liquid diffusion fiber sheet 201, the wearer can see a more vibrant picture.

By applying a hot-melt adhesive, which is optically transparent, on the surface of the printed layer 201a, the picture of the printed layer 201a does not suffer from blurriness or bleeding even when wet. This allows various types of ink to be used for the printed layer 201a, such as water based inks and oil based inks. Additionally, the picture of the printed layer 201a can be prevented from being removed by friction or fading.

An absorbent polymer layer (not illustrated) can be disposed in the stretchable composite sheet. Additionally, the surface of the air permeable sheet 205 disposed on the outermost side may be coated with a water repellant. Examples of a water repellant include oil based, silicone based, and Teflon based water repellants. By coating the surface of the air permeable sheet 205 on the outermost side with a water repellant, water infiltration from the outside can be further effectively prevented.

Examples of an absorbent polymer include superabsorbent polymers such as sodium polyacrylate. The absorbent polymer in a granular or powdered state can be disposed as an absorbent polymer layer between the liquid diffusion fiber sheet 201 and the air permeable sheet 203. In such a configuration, the absorbent polymer layer further increase the rate of absorption of urine. Additionally, by disposing the liquid diffusion fiber sheet 201 and the air permeable sheet 205 on the outer side of the absorbent polymer layer, urine escaping outside can be further effectively prevented. By the air permeable sheet 203 being disposed on the side most proximal to the body, skin comfort and air permeability are made excellent. In configurations in which the absorbent polymer layer is disposed on the side of the liquid diffusion fiber sheet 201 proximal to the air permeable sheet 205, the liquid diffusion fiber sheet 201 can absorb large amounts of urine, allowing the amount of absorbent polymer used to be reduced.

A plurality of fine holes may be formed on the surface of the air permeable sheet 205 disposed on the outermost side. By forming such holes, air permeability can be further improved. Such holes, for example, may be formed in an organized dot pattern or may be formed in a random pattern. Additionally, the holes may be formed in the entire surface of the air permeable sheet 205 or may be formed in only some regions.

Hydrophobic Sheet

Figure 9A:
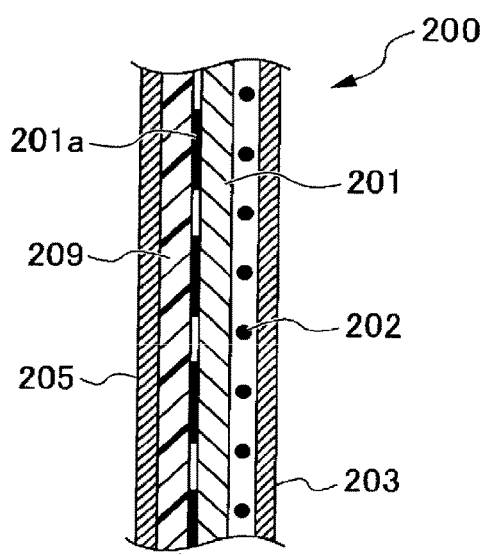
FIGS. 9A and 9B illustrate variations in which a hydrophobic sheet 209 is disposed on the chassis 20.
Figure 9B:
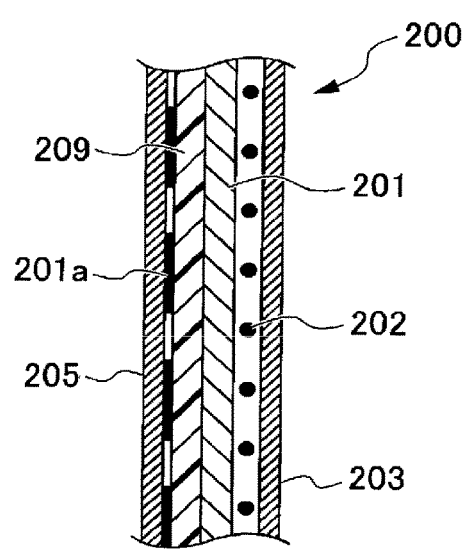

As illustrated in FIGS. 9A and 9B, the stretchable composite sheet 200 may be further provided with a hydrophobic sheet 209. The stretchable composite sheet 200 illustrated in FIG. 9A includes the hydrophobic sheet 209 disposed between the second air permeable sheet 205 and the liquid diffusion fiber sheet 201 as a non-hydrophilic sheet. The hydrophobic sheet 209 is preferably a moisture permeable film that lets air pass but not water. In configurations in which the printed layer 201a is formed on the surface of the liquid diffusion fiber sheet 201 on the side proximal to the second air permeable sheet 205, the hydrophobic sheet 209 is required to improve the visibility of the printed layer 201a. Thus, a moisture permeable film with high transparency is preferably used. In such configurations, a detailed picture formed on the printed layer 201a can be further clearly displayed. The hydrophobic sheet 209 is not limited to having high transparency and may be semitransparent.

The stretchable composite sheet 200 illustrated in FIG. 9B includes the hydrophobic sheet 209 disposed between the second air permeable sheet 205 and the liquid diffusion fiber sheet 201, and the printed layer 201a is formed on the surface of the hydrophobic sheet 209 on the side proximal to the air permeable sheet 205. In the example illustrated in FIG. 9B, the linear elastic bodies 202 are disposed between the liquid diffusion fiber sheet 201 and the first air permeable sheet 203. However, the linear elastic bodies 202 may be disposed between the liquid diffusion fiber sheet 201 and the hydrophobic sheet 209.

In configurations in which the printed layer 201a is formed on the liquid diffusion fiber sheet 201 or the hydrophobic sheet 209, to improve the visibility of the printed layer 201a, the linear elastic bodies 202 are preferably not disposed on the side of the printed layer 201a proximal to the air permeable sheet 205. Additionally, the hydrophobic sheet 209 is not limited to having hydrophobicity and may have a waterproofing ability.

In the example described above, a configuration in which the hydrophobic sheet 209 is disposed is described. However, a hydrophilic sheet may be disposed instead of the hydrophobic sheet 209, and disposing a hydrophilic sheet is preferable.

Figure 10A:
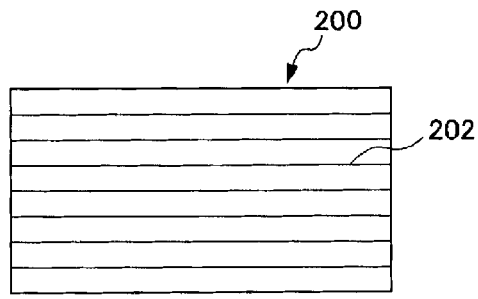
FIGS. 10A to 10H illustrate variations of how linear elastic bodies 202 are disposed.
Figure 10E:
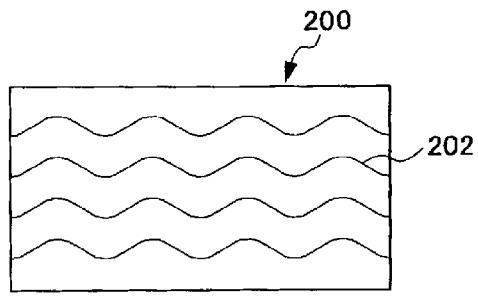
Figure 10B:
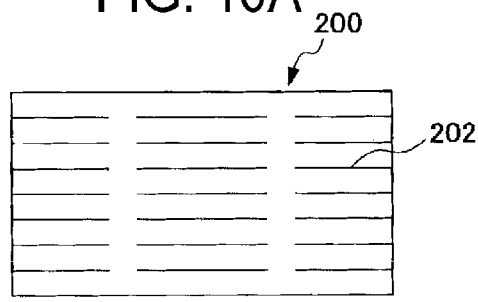
Figure 10F:
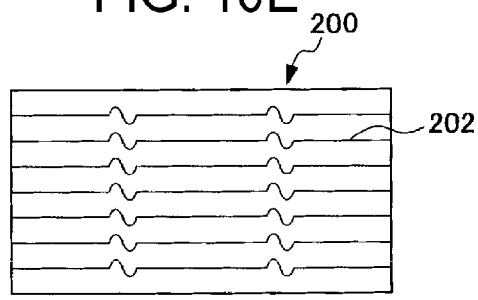
Figure 10C:
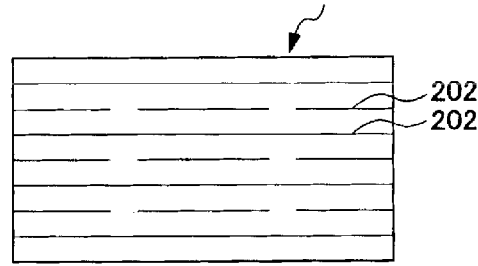
Figure 10G:
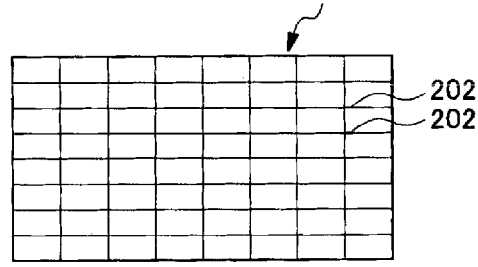
Figure 10D:
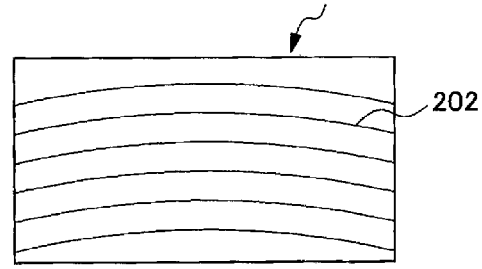
Figure 10H:
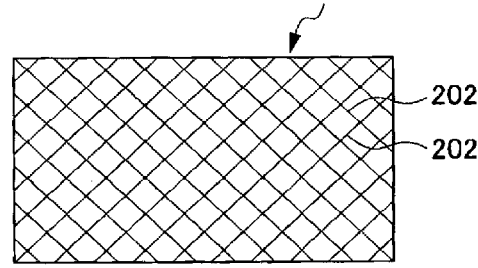

FIGS. 10A to 10H illustrate how the linear elastic bodies are disposed according to different variations. The linear elastic bodies 202 illustrated in FIGS. 10A to 10C may be disposed in a straight linear manner. The linear elastic bodies 202 illustrated in FIG. 10D may be disposed in a curved linear manner. Additionally, the curve may have a wave-like shape as illustrated in FIG. 10E. Furthermore, the linear elastic bodies 202 illustrated in FIG. 10F include a straight linear portion and a curved linear portion. As illustrated in FIG. 10G, the linear elastic bodies 202 may include not only linear elastic bodies 202 disposed in a width direction and parallel with each other, but also linear elastic bodies 202 disposed in the direction perpendicular thereto, forming a grid-like pattern. Additionally, as illustrated in FIG. 10H, the linear elastic bodies 202 may have an inclined grid-like pattern. The linear elastic bodies 202 may continue across the entire stretchable composite sheet 200 (see for example FIG. 10A) or be non-continuous (see for example FIG. 10B).

Figure 11A:
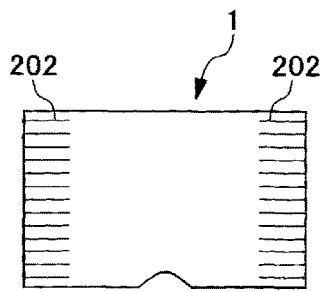
FIGS. 11A to 11I illustrate different variations of how the linear elastic bodies 202 are disposed.
Figure 11B:
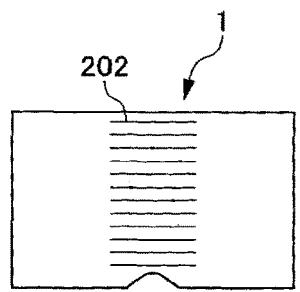
Figure 11C:
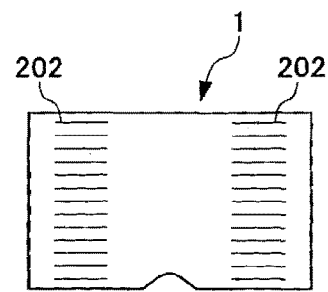
Figure 11D:
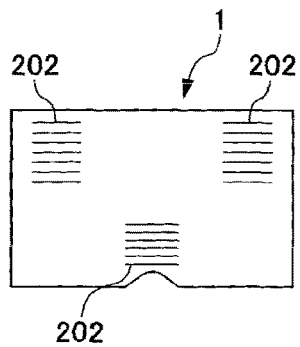
Figure 11E:
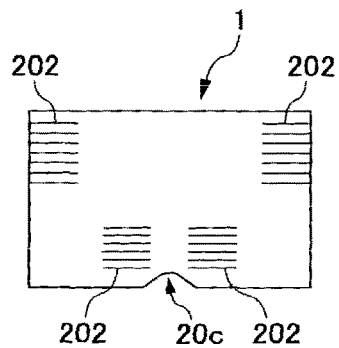
Figure 11F:
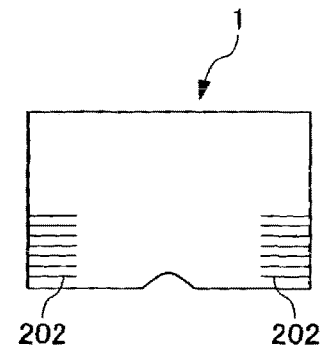
Figure 11G:
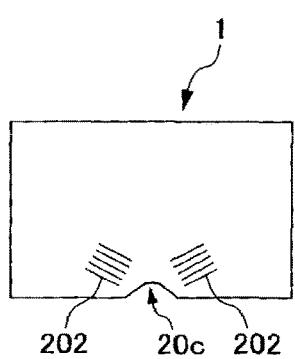
Figure 11H:
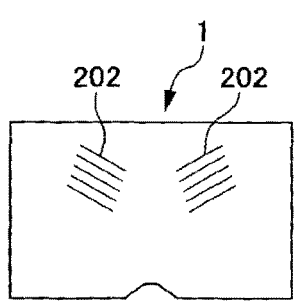
Figure 11I:
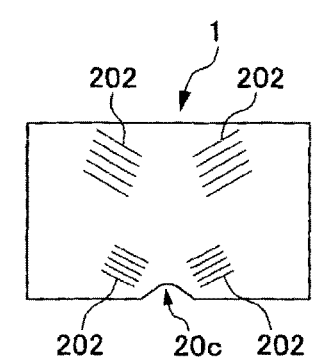

The disposable garment 1 according to an embodiment of the present invention includes a stretchable composite sheet 200 partially provided with the linear elastic bodies 202. This allows the region where a pressing force is applied and the strength of the pressing force on the body of wearer to be varied. FIG. 11A illustrates an example in which the linear elastic bodies 202 are located in the side portions of the front portion and/or the back portion of the disposable garment 1. FIG. 11B illustrates an example in which the linear elastic bodies 202 are located in the central portion of the front portion and/or back portion. FIG. 11C illustrates an example in which the linear elastic bodies 202 are located in a region between the side portions and the central portion of the front portion and/or the back portion. FIG. 11D illustrates an example in which the linear elastic bodies 202 are located in a region between the side portions and the central portion of the front portion and/or the back portion on the upper side and the linear elastic bodies 202 are located in the inside leg portion of the front portion and/or the back portion. FIG. 11E illustrates an example in which the linear elastic bodies 202 are located in the side portions of the front portion and/or the back portion on the upper side and located on both sides of the inside leg portion 20c of the front portion and/or the back portion. FIG. 11F illustrates an example in which the linear elastic bodies 202 are located in the side portions of the front portion and/or the back portion on the lower side. FIG. 11G illustrates an example in which the linear elastic bodies 202 are disposed at an incline to the left and the right of the inside leg portion of the front portion and/or the back portion. FIG. 11H illustrates an example in which the linear elastic bodies 202 are disposed at an incline on the left and right side in the upper central portion of the front portion and/or the back portion. FIG. 11I illustrates an example in which the linear elastic bodies 202 are disposed at an incline to the left and the right of the inside leg portion and on the left and right side in the upper central portion of the front portion and/or the back portion. In configurations in which the linear elastic bodies 202 are disposed at a left/right incline, the orientations at each portions may be the same or different. The patterns illustrated in FIGS. 11A to 11I, for example, may have different patterns on the front side and the back side of the disposable garment 1.

In the disposable garment 1 according to an embodiment of the present invention, the linear elastic bodies 202 are preferably disposed throughout the entire chassis 20. The configuration illustrated in FIG. 10A in which the stretchable composite sheet 200 including continuous linear elastic bodies 202 disposed at predetermined intervals is used and the stretching direction of the linear elastic bodies 202 is aligned with the direction around the waist is preferable because the fit of the disposable garment 1 on the body is good and the production of the stretchable composite sheet is simple. In diapers that include an absorbent member for urine, to prevent the diaper from falling down when a weight thereof is increased by the absorbent member absorbing urine, the width of the torso band 21 is typically enlarged to ensure a tight fit around the waist of the wearer. However, the disposable garment 1 according to an embodiment of the present invention, the fit on the body is supported not only by the elastic force of the torso band 21, but also by the linear elastic bodies 202 disposed throughout the chassis 20. This increases the good fit of the disposable garment 1 on the body, thus allowing for designs including making the length to be that similar to typical undergarments so that the disposable garment 1 can be worn on hip bone of the wearer or below. The disposable garment 1 includes the chassis 20 with stretchability. This means that the torso band 21 does not need to have an excessive width. Thus, the top end portion of the torso band 21 does not stick out from the pants or skirt when the disposable garment 1 is worn by the wearer, the appearance when the garment is worn by the wearer is good, and the disposable garment 1 can be worn by the wearer without reluctance or discomfort.

Figures 12A, 12B:
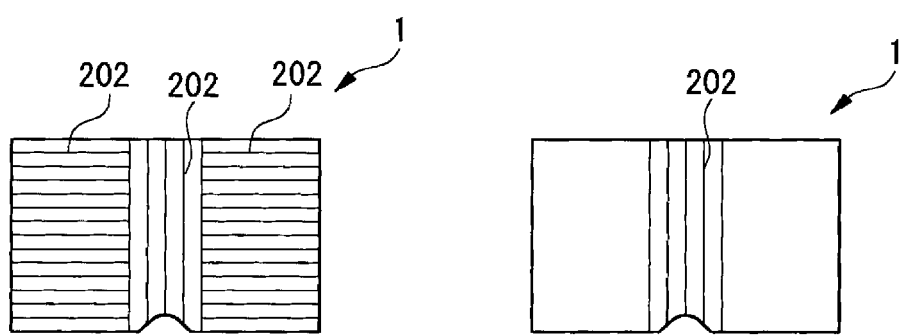
FIGS. 12A and 12B illustrate other different variations of how the linear elastic bodies 202 are disposed.

FIG. 12A illustrates an example in which the linear elastic bodies 202 are disposed in the vertical direction in the central portion of the front portion and/or the back portion of the disposable garment 1 and the linear elastic bodies 202 are disposed in the lateral direction on either side of the central portion.

FIG. 12B illustrates an example in which the linear elastic bodies 202 are disposed in the vertical direction in only the central portion of the front portion and/or the back portion of the disposable garment 1. The disposable garment 1 may have a combination of the patterns illustrated in FIGS. 12A and 12B on the front side and the back side. Additionally, the disposable garment 1 may have the pattern illustrated in FIG. 12A or FIG. 12B on the front or back side, and the disposable garment 1 may have, on the other side, no linear elastic bodies or the pattern illustrated in FIGS. 11A to 11I. This allows the linear elastic bodies 202 to push the absorbent member against the body via the body or elastic sheet 17.

Figure 13A:
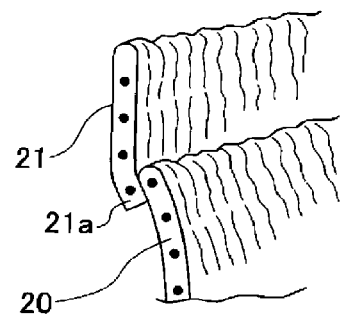
FIGS. 13A to 13C are diagrams for illustrating the joined structure of a torso band 21 and the chassis 20.
Figure 13B:
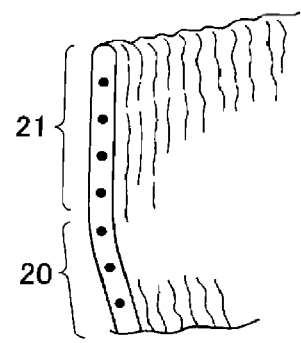
Figure 13C:
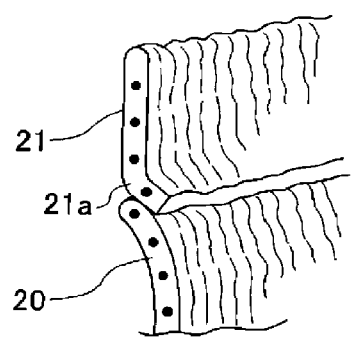

As illustrated in FIG. 13B, the torso band 21 and the chassis 20 of the disposable garment 1 according to an embodiment of the present invention may be integrally formed via the stretchable composite sheet or, as illustrated in FIGS. 13A, 13C, may be separate members. In configurations in which the torso band 21 and the chassis 20 are separate members, as illustrated in FIG. 13A, a joined portion 21a can be formed between the inner side (side proximal to the body) of the lower end of the torso band 21 and the outer side of the upper end of the chassis 20 to join together the ends. This allows for more push against the body.

Additionally, as illustrated in FIG. 13C, the joined portion 21a can be formed on the outer side of the lower end of the torso band 21 and the inner side (side proximal to the body) of the upper end of the chassis 20 to join together the ends. This allows excessive pressure against the body to be prevented. Examples of methods of joining the torso band 21 and the chassis 20 include adhesion by a hot-melt adhesive, sewing, thermal sealing, and ultrasonic bonding. Joining together the torso band 21 and the chassis 20 with a stretchable composite sheet results in a disposable garment 1 that is simple to produce. In a configuration in which the torso band 21 and the chassis 20 are separate members, the torso band 21 and the chassis 20 can have different elasticity, thickness, and material, which enables the thermal retention properties, the air permeability, and the skin comfort to be easily varied. Additionally, the torso band 21 and the chassis 20 can be produced at different places and then be combined. Also, if a portion of the torso band 21 or the chassis 20 is fouled, the torso band 21 and the chassis 20 can be separated and only the fouled portion can be replaced.

Embodiments in which the disposable garment includes, as described above, the stretchable composite sheet, which includes the liquid diffusion fiber sheet made of a paper sheet and linear elastic bodies, disposed between air permeable sheets made of a nonwoven fabric are simple to produce and have reduced production costs as well as are easier to dispose of after use compared to conventional configurations in which the elastic bodies are disposed between nonwoven fabrics. In other words, the affinity between a nonwoven fabric and an adhesive such as a hot-melt adhesive is low. As a result, to provide the strength needed for a garment, a large amount of a hot-melt adhesive is needed to join the nonwoven fabric and the elastic bodies together and joining takes a long time. Additionally, the affinity of a hot-melt adhesive with the liquid diffusion fiber sheet made of a paper sheet is greater than that with a nonwoven fabric. This allows a sufficient joining strength to be obtained using a small amount of hot-melt adhesive. As a result, the amount of hot-melt adhesive used can be reduced, the time needs for joining can be reduced, various joining equipment becomes unnecessary, and production is made simple. To provide sufficient strength to the stretchable composite sheet, conventionally a large amount of hot-melt adhesive has been used or a method of joining two or more layers of a nonwoven fabric has been used. Such sheets have increased strength but are difficult to break down at the time of disposal. In configurations in which the stretchable composite sheet including the liquid diffusion fiber sheet made of a paper sheet is disposed between the air permeable sheets made of a nonwoven fabric, the affinity between the liquid diffusion fiber sheet and the hot-melt adhesive is good, allowing the amount of hot-melt adhesive used to be reduced. Also, providing the liquid diffusion fiber sheet improves the overall strength of the sheet. This ensures sufficient strength without requiring the use of multiple layers of the air permeable sheets made of a nonwoven fabric. As a result, a disposable garment with sufficient strength can be easily obtained and the garment can be broken down easily after use and disposed of.

Elastic Sheet

In an embodiment of the present invention in which the disposable garment 1 is a diaper, the elastic sheet 17 may be provided stretching from the front portion 20a of the inner side of the chassis 20 to the back portion 20b passing through the crotch region of the wearer. The elastic sheet 17, for example, may be a sheet member made of a nonwoven fabric, a moisture permeable film, or a sheet member such as paper with strings of rubber joined thereto, or may be a material with intrinsic elasticity such as a rubber, a urethane, a silicone sheet, a stocking or knit. By providing the elastic sheet 17, the pressing force of the absorbent member against the body is further increased, and when the garment is worn by the wearer, the shape of the genital organs and urinary organs can be concealed and the garment can function as a supporter. The elastic sheet 17 preferably has stretchability in the longitudinal direction (the direction from the front portion 20a of the chassis 20 toward the back portion 20b). The absorbent member 10 can be disposed on the inner side of the elastic sheet 17. In configurations in which the elastic sheet 17 is provided with the absorbent member 10, the contractive force of the elastic sheet 17 stretched when the garment is worn by the wearer and the contractive force of the chassis 20 with stretchability make the absorbent member 10 push against the side of the body, prevent the absorbent member 10 from swelling outward when the garment is worn by the wearer, and reduce the gap between the body and the absorbent member 10. Thus, the contact with the body is improved. As a result, such a configuration can prevent swelling at the inside leg portion 20c and has improved appearance and feel over conventional configurations in which an elastic sheet with stretchability is provided and the absorbent member is provided on the elastic sheet. With the stretching direction of the elastic sheet 17 and the stretching direction of the chassis 20 intersecting one another, when the disposable garment is worn by the wearer and the chassis 20 stretches, the joined portions of the elastic sheet 17 and the chassis 20 on the front portion side and the back portion side are pulled in the direction widening the interval between the two. This stretches the elastic sheet 17, and the elastic sheet as a whole is raised upwards. As a result, the absorbent member 10 attached to the elastic sheet 17 is pushed in the direction toward the body and the contact of the absorbent member 10 with the body is enhanced. In particular, in the inside leg portion with stretchability where the elastic bodies 202 are disposed, with the stretching direction of the elastic sheet 17 intersecting the stretching direction of the inside leg portion, when the chassis 20 stretches in the width direction when the garment is worn by the wearer and in particular the leg cuff openings 20f stretch in the width direction, this raises the inside leg portion upward, and the combined pressing force of the inside leg portion and the elastic sheet enable reliable contact between the absorbent member 10 and the body. Additionally, movement of the chassis 20 caused by the wearer moving has little effect on the movement of the elastic sheet 17 because the chassis 20 and the elastic sheet 17 are separate members. As a result, in configurations in which the absorbent member 10 described below is joined to the elastic sheet 17, the absorbent member 10 can be continuously pressed against the body and sweat and urine leakage can be prevented by the absorbent member 10.

Figure 14:
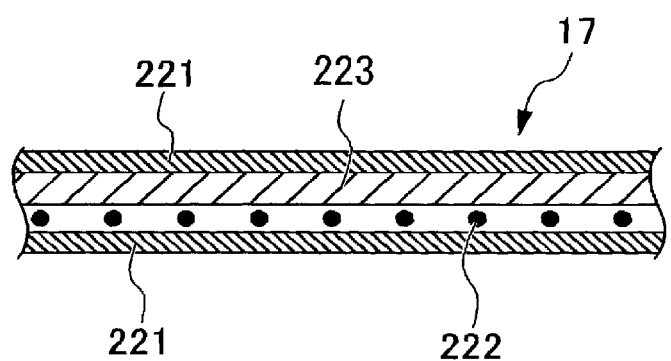
FIG. 14 is a cross-sectional view of a portion of an elastic sheet 17 provided with the liquid diffusion fiber sheet 223.

The elastic sheet 17 can include a stretchable composite sheet similar to that used in the chassis 20. Examples of the stretchable composite sheet include, for example, the configuration illustrated in FIG. 14 in which a liquid diffusion fiber sheet 223 and elastic members 222 such a rubber threads are supported between two nonwoven fabrics 221, 221. The liquid diffusion fiber sheet 223 may or may not be disposed closer to the body than the elastic members 222. The liquid diffusion fiber sheet 223 provided on the elastic sheet 17 can absorb any urine leaked from the absorbent member when the wearer turns over in his/her sleep, and any urine is leaked from the absorbent member. As the elastic members 222, members similar to the linear elastic bodies of the stretchable composite sheet can be used.

Elastic Sheet Variations

FIGS. 15A to 15J and 16A to 16H illustrate various configurations of the elastic sheet 17. As illustrated in FIGS. 15A to 15J and 16A to 16H, the elastic sheet 17 is not limited to including the elastic members 222 throughout the sheet and the elastic sheet 17 may be partially provided with elastic members. Additionally, elastic members having different elastic forces may be used in combination.

The elastic sheet 17 illustrated in FIG. 15A includes elastic members 222 disposed uniformly in the longitudinal direction of the elastic sheet 17.

The elastic sheet 17 illustrated in FIG. 15B includes no elastic members in the central portion and includes elastic members 222 in both end portions in the longitudinal direction.

The elastic sheet 17 illustrated in FIG. 15C includes elastically strong elastic members 222*a* and elastically weak elastic members 222*b* as the elastic members 222. The elastic members 222*a* are disposed in the side portions and the elastic members 222*b* are disposed in other portions. In such a configuration, the elastically strong elastic members 222*a* in the side portions increase the contact with the body, thus enhancing the ability to prevent side leakage of urine. Additionally, less contact with the body is provided in the portions other than the side portions, thus no oppressive feeling is felt.

The elastic sheet 17 illustrated in FIG. 15D includes the elastically strong elastic member 222*a* disposed in the central portion and the elastically weak elastic members 222*b* in the other portions. In such a configuration, the elastic members 222*a* in the central portion are highly elastic, allowing for a good fit over the recess of the buttocks and good wear-ability.

The elastic sheet 17 illustrated in FIG. 15E includes elastically strong elastic members 222*a* disposed in the side portions and elastically weak elastic members 222*b* in the portions other excluding the central portion. In the central portion, the elastically strong elastic member 222*a* is disposed in one region and the elastically weak elastic member 222*b* is disposed in other region. In such a configuration, the elastically strong elastic members 222*a* disposed in the side portions increase the contact with the body side and enhance the ability to prevent side leakage of urine. Additionally, less contact with the body is provided in the portions other than the side portions, thus less oppressive feeling is felt. Furthermore, by providing the elastically strong elastic members 222*a* in the central portion on the side corresponding to the buttocks side, a good fit over the recess of the buttocks and good wear-ability is achieved.

The elastic sheet 17 illustrated in FIG. 15F includes the elastic members 222 disposed in the side portions in a curved manner.

In the elastic sheet 17 illustrated in FIG. 15G adjacent elastic members 222 in the side portions are disposed tightly together with small intervals, and adjacent elastic members 222 on the inner side have wider intervals. In such a configuration, the contact with the body side is enhanced and the ability to prevent side leakage of urine is enhanced. Additionally, less contact with the body is provided in the portions other than the side portions, thus no oppressive feeling is felt.

The elastic sheet 17 illustrated in FIG. 15H includes elastic members 222 that are provided in a non-continuous intermittent manner in the length direction.

The elastic sheet 17 illustrated in FIG. 15I includes the elastically strong elastic members 222*a* and the elastically weak elastic members 222*b* as the elastic members 222 connected in an alternating arrangement.

The elastic sheet 17 illustrated in FIG. 15J includes the elastic members 222 disposed at the front and back in a curved manner.

The elastic sheet 17 illustrated in FIG. 16A has no elasticity in the front and back end portions of the elastic sheet 17 and the elastic members 222 are disposed in the central portion of the elastic sheet 17.

The elastic sheet 17 illustrated in FIG. 16B includes the elastically strong elastic members 222*a* disposed in the front and back end portions of the elastic sheet 17 and the elastically weak elastic members 222*b* in the central portion of the elastic sheet 17. In such a configuration, the front and back portion of the elastic sheet 17 provided with the elastically strong elastic members 222*a* have enhanced contact with the body side. Thus, the ability to prevent side leakage of urine is enhanced and a good fit over the recess of the buttocks and good wear-ability are achieved. Additionally, less contact with the body is provided in the central portion than the side portions, thus less oppressive feeling is felt in the central portion.

The elastic sheet 17 illustrated in FIG. 16C includes elastic members 222 that are disposed in a wave-like manner rather than in a straight linear manner.

The elastic sheet 17 illustrated in FIG. 16D includes the elastic members 222 disposed in the longitudinal direction and the transverse direction with the elastic members 222 intersecting each other.

The elastic sheet 17 illustrated in FIG. 16E includes the elastic members 222 disposed in an inclined grid-like pattern with the elastic members 222 intersecting each other.

The elastic sheet 17 illustrated in FIG. 16F has a configuration that is a combination of that of FIG. 15F and FIG. 16C. The elastic members 222 in the central portion of the elastic sheet 17 are disposed in a wave-like manner in the longitudinal direction. The elastic members 222 in the side portions are disposed in a curved manner.

The elastic sheet 17 is not limited to theses configuration and may also have a configuration that is a combination of that of FIGS. 15A to 15J and FIG. 16A to 16F. Additionally, the strength/weakness of the elastic members 222 can be adjusted depending on the thickness, the strength/weakness of the tension, the size of the pitch of the elastic members 222, and whether the members are joined continuously or intermittently.

The elastic sheets 17 illustrated in FIGS. 15A to 15J and FIGS. 16A to 16F are rectangular, but are not limited thereto. For example, the elastic sheet 17 may have a wider shape at both ends as illustrated in FIG. 16G. Such a shape allows for the side portions of the elastic sheet 17 to not come into contact with the legs of the wearer, thus improving the feeling. When the chassis 20 includes the elastic sheet 17 with such a shape, a diaper such as that illustrated in FIG. 16H is formed.

As described above, the elastic sheet 17 may be provided with the elastic members 222 that extend from the front portion of the chassis 20 to the back portion in a variety of manners. Accordingly, the contractive force of the elastic members 222 can form lines on the surface of the elastic sheet 17 to form multiple gaps between the elastic sheet 17 and the body. This improves the air permeability of the elastic sheet 17.

Figure 17:
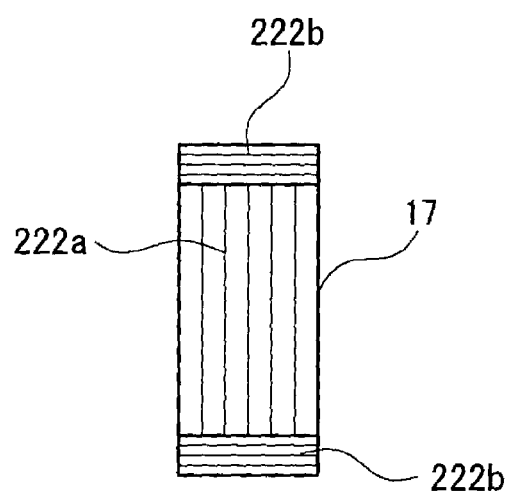
FIG. 17 illustrates another configuration of the elastic sheet 17.

As illustrated in FIG. 17, the elastic sheet 17 may have a configuration in which the end portions of the elastic sheet are provided with the elastic members 222b in the width direction to provide stretchability in the width direction and the central portion is provided with the elastic members 222a in the longitudinal direction to provide stretchability in the longitudinal direction. In such a configuration, with the elastic sheet 17 joined to the chassis 20 at the end portions of the elastic sheet 17, the stretchability of the chassis 20 in the direction around the waist is not hindered.

Additionally, as illustrated in the example in FIG. 15A, the liquid diffusion fiber sheet 223 made of a paper sheet may be disposed inside the elastic sheet 17. The variations of how the liquid diffusion fiber sheet 223 is disposed inside the elastic sheet 17 are shared with the elastic sheets 17 described above illustrated in FIGS. 15A to 15J and 16A to 16G By disposing the liquid diffusion fiber sheet 223 inside the elastic sheet 17, even if urine leaks from the absorbent member 10, the urine can be absorbed by the liquid diffusion fiber sheet 223. Thus, the ability to prevent side leakage of urine can be further enhanced. Additionally, lines are easily formed on the surface of the liquid diffusion fiber sheet 223, allowing for multiple gaps to be formed inside the elastic sheet 17. As a result, the air permeability of the elastic sheet 17 can be improved. The elastic sheet 17 may be embossed. In the embossing process, the liquid diffusion fiber sheet 223 may be embossed prior to being placed inside the elastic sheet 17, or the elastic sheet 17 may be embossed after the liquid diffusion fiber sheet 223 is placed inside the elastic sheet 17. By an embossing process being performed on the elastic sheet 17 or the liquid diffusion fiber sheet 223, the flexibility of the elastic sheet 17 can be improved, and the skin comfort is further improved. This allows the contact between the absorbent member 10 and the body of the wearer to be further enhanced.

Joining the Elastic Sheet and the Absorbent Member

Figure 18A:
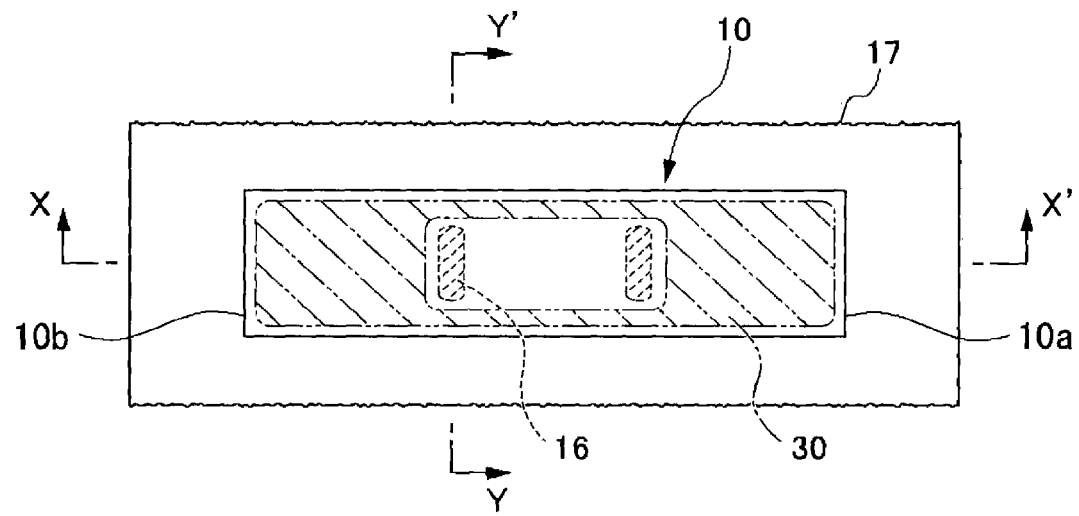
FIGS. 18A to 18C are diagrams for explaining how the elastic sheet 17 and the absorbent member 10 are joined.
Figure 18B:
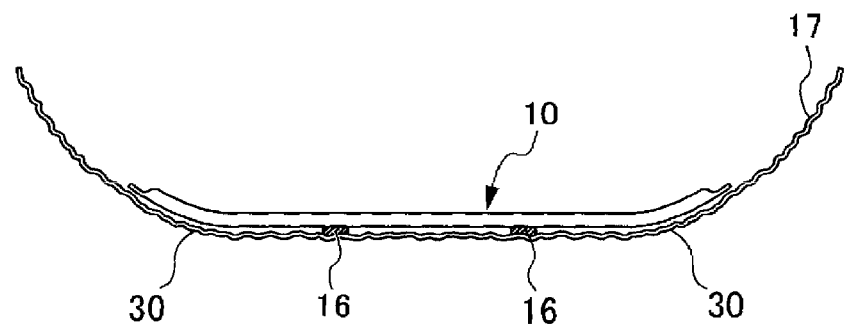
Figure 18C:
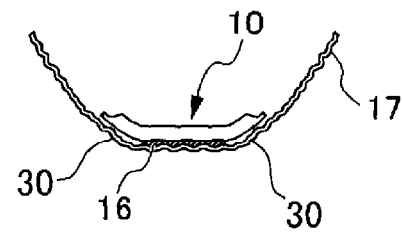

FIGS. 18A to 18C and 19A to 19B are diagrams for explaining how the elastic sheet 17 and the absorbent member 10 may be joined. FIG. 18A is a plan view of the elastic sheet 17 on which the absorbent member 10 is joined. FIG. 18B is a vertical cross-sectional view taken along the longitudinal direction of the elastic sheet 17 on which the absorbent member 10 is joined. The vertical cross-sectional view is taken along the line X-X' of FIG. 18A. FIG. 18C is a vertical cross-sectional view taken along the width direction of the elastic sheet 17. The vertical cross-sectional view is taken along the line Y-Y' of FIG. 18A.

As illustrated in FIGS. 18A to 18C and 19A to 19B, the elastic sheet 17 and the absorbent member 10 are joined by an adhesive 16. In the example illustrated in FIG. 18A, the adhesive 16 is applied at two sections along the longitudinal direction of the elastic sheet 17. As illustrated in FIG. 18A, by applying the adhesive 16 at two sections which are inward from end portions 10a, 10b of the absorbent member 10 in the longitudinal direction, a non-joined portion 30 is formed outside of the region containing the adhesive 16. In the non-joined portion 30, the absorbent member 10 is not restrained by the elastic sheet 17 and can move in the up and down direction more freely than in a configuration in which the absorbent member 10 is joined near the end portions 10a, 10b thereof to the elastic sheet 17. Additionally, in a configuration in which the absorbent member 10 is joined near the end portions 10a, 10b to the elastic sheet 17, by joining the absorbent member 10 to the elastic sheet 17 with the adhesive 16 applied at a portion inward from the end portions 10a, 10b of the absorbent member 10, in the portion outward from the portion between the adhesive 16 and the adhesive 16, the elastic sheet 17 enables the absorbent member 10 to reliably push against the body.

As a result, when the wearer wears such a disposable garment 1, as illustrated in FIG. 18B, in the longitudinal direction of the elastic sheet 17, the stretchability of the elastic sheet 17 is not hindered and the end portions of the elastic sheet 17 and the absorbent member 10 rise upward. In a similar manner, as illustrated in FIG. 18C, in the width direction of the elastic sheet 17, the end portions of the elastic sheet 17 and the absorbent member 10 rise upward. Accordingly, the contact of the elastic sheet 17 and the absorbent member 10 with the wearer can be enhanced and the contact of the absorbent member 10 with the body of the wearer can be enhanced. This allows leakage of urine to be prevented. Additionally, by the end portions of the elastic sheet 17 and the absorbent member 10 rising upward, fold portions formed on the periphery of the absorbent member 10 (the side edges in the width direction) becomes erect forming three-dimensional side gathers. These gathers prevent urine leakage. By the side gathers being formed, gaps are formed between the absorbent member 10 and the body in the width direction of the absorbent member 10, enabling air permeability to be ensured.

Figure 19A:
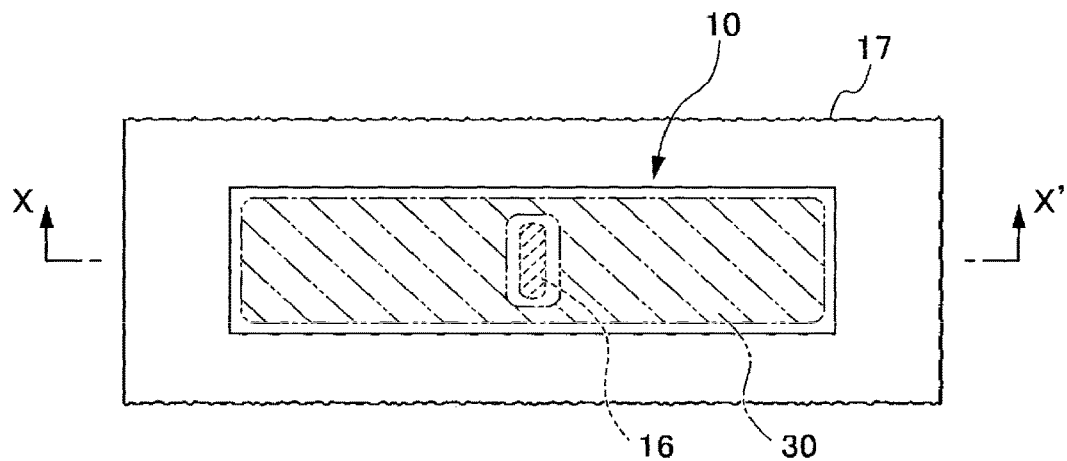
FIGS. 19A and 19B are diagrams for explaining how the elastic sheet 17 and the absorbent member 10 are joined.
Figure 19B:
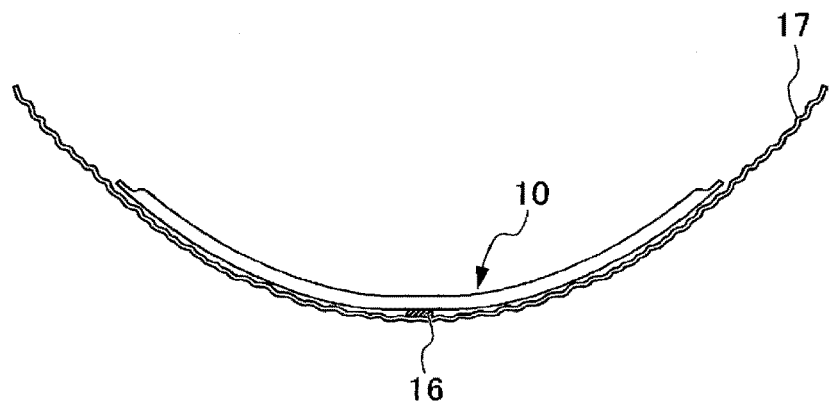

FIGS. 19A and 19B illustrate another example of how the elastic sheet 17 and the absorbent member 10 may be joined.

As illustrated in FIG. 19A, the elastic sheet 17 and the absorbent member 10 are joined by the adhesive 16 being applied therebetween at one central section in the longitudinal direction of the elastic sheet 17. By applying the adhesive 16 in one section in the central portion as illustrated in FIG. 19A, the area of the non-joined portion 30 can be made larger than the area of the non-joined portion 30 illustrated in FIG. 18A. This makes the region where the stretchability of the elastic sheet 17 is not hindered even larger.

As a result, when the wearer wears the disposable garment 1, as illustrated in FIG. 19B, in the longitudinal direction of the elastic sheet 17, the end portions in the longitudinal direction of the elastic sheet 17 and the absorbent member 10 are raised up higher than in the configuration illustrated in FIG. 18B, and the inside leg of the wearer can be push from directly below. This allows the contact between the elastic sheet 17 and the absorbent member 10 and the wearer to be further enhanced over a conventional disposable diaper that includes an absorbent member 10 with hanging end portions in the longitudinal direction. Thus, urine leakage can be more effectively prevented.

Additionally, in conventional disposable diapers that include an absorbent member 10 attached with end portions being hung in the longitudinal direction, the flexibility of the absorbent member 10 is low (has little slack) and the contact between the absorbent member 10 and the wearer is bad. However, in the disposable garment 1 of the present embodiment, the elastic sheet 17 can force upward the end portions in the longitudinal direction of the absorbent member 10 with poor flexibility. This allows the contact between the absorbent member 10 and the wearer to be further enhanced. Joining the absorbent member 10 to the elastic sheet 17 with the elastic sheet 17 being in a stretched state results in problems maintaining the stretched state of the elastic sheet 17 and time lost in positioning. This makes joining a laborious and time-consuming process. Thus, the absorbent member 10 is preferably joined to the elastic sheet 17 with the elastic sheet 17 being in a non-stretched state.

Figure 20:
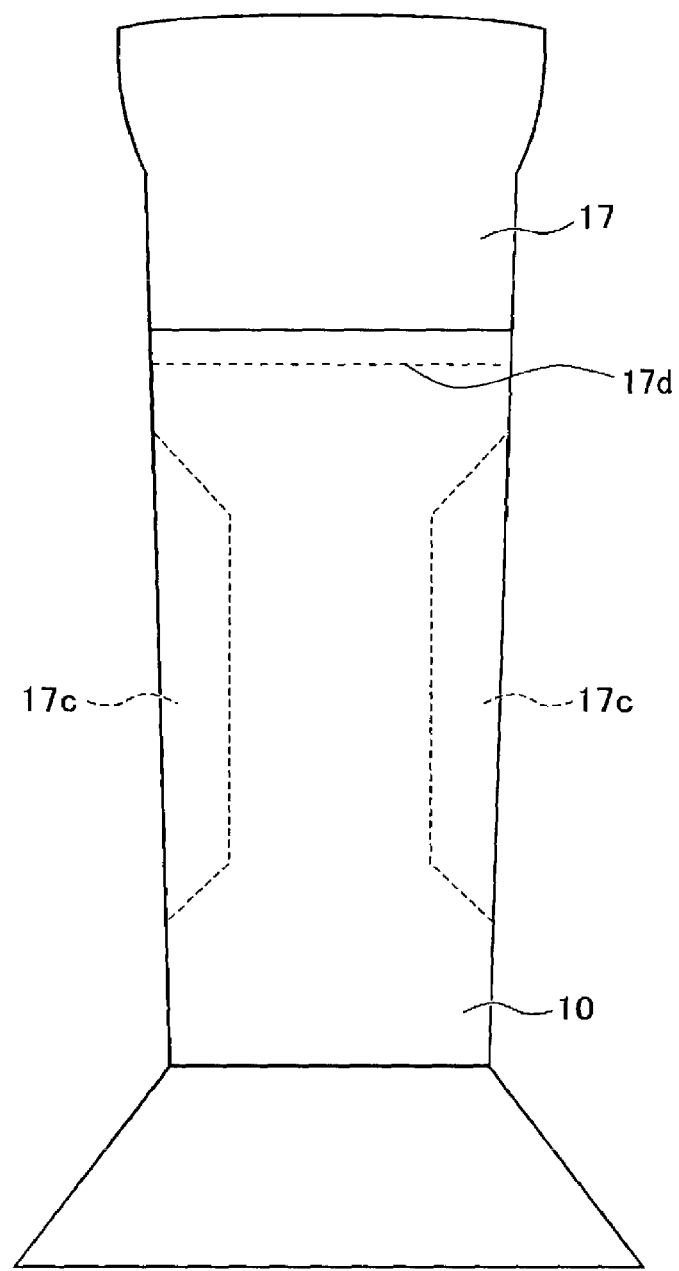
FIG. 20 is a diagram for explaining the elastic sheet 17 provided with cut-out portions 17c.

FIG. 20 illustrates the elastic sheet 17 according to another embodiment. As illustrated in FIG. 20, the width of the elastic sheet 17 is approximately equal to the width of the absorbent member 10, and cut-out portions 17c are provided on the sides in the width direction of the elastic sheet 17. The cut-out portions 17c come into contact with the thigh portions of the wearer when the disposable garment 1 is worn by the wearer. Additionally, in the elastic sheet 17, a severable portion such as a perforated line 17d may be provided in the width direction. The elastic sheet 17 can be severed at the perforated line 17d as necessary to remove the pressing force of the elastic sheet 17. The perforated line 17d can be provided on the elastic sheet 17 irrespective of the shape of the elastic sheet 17. In a configuration in which the widths of the elastic sheet 17 and the width of the absorbent member 10 are approximately equal, when the disposable garment 1 is worn by the wearer, the sides in the width direction of the elastic sheet 17 and the absorbent member 10 poke into the thigh portions of the wearer. This reduces the comfort of the garment, especially when the elastic sheet 17 and the absorbent member 10 use a nonwoven fabric. However, in the present embodiment in which the cut-out portions 17c are provided that comes into contact with the thigh portions of the wearer of the elastic sheet 17, the elastic sheet 17 is less likely to come into contact with the thigh portions of the wearer. This improves the comfort of the garment.

The method of joining together the elastic sheet 17 and the absorbent member 10 is not limited to using the hot-melt adhesive 16. Examples of other methods include sewing, thermal sealing, adhesion via ultrasonic bonding or double sided tape, other known methods, and a combination of thereof. Additionally, a surface fastener, a hook, or a button can be used in joining together the elastic sheet 17 and the absorbent member 10.

Joining the Elastic Sheet to the Chassis

As illustrated in FIG. 2, the region to one end in the longitudinal direction of the elastic sheet 17 is joined to the front portion 20a of the chassis 20 and the region to the other end in the longitudinal direction is joined to the back portion 20b of the chassis 20. The elastic sheet 17 extends over the upper surface side of the inside leg portion 20c from the front portion 20a to the back portion 20b of the chassis 20. Here, the region to one end and the region to the other end of the elastic sheet 17 are not required to include the end portions and may be regions spaced apart from the end portions. The elastic sheet 17 may be detachably attached to the chassis 20 via a surface fastener or a pressure-sensitive adhesive tape.

In configurations in which the end portion in the longitudinal direction of the elastic sheet 17 only is joined to the chassis 20, the stretchability of the elastic sheet 17 and the chassis 20 where it overlaps the elastic sheet 17 is not hindered as in configurations in which the elastic sheet 17 is joined all its entire surface to the chassis 20. Also the stretchability of the regions of the chassis 20 other than where it is joined to the elastic sheet 17 is maintained. Accordingly, the disposable garment 1 can be made easy to wear for the wearer. Because the stretchability of the elastic sheet 17 and the chassis where it overlaps the elastic sheet 17 is not hindered, in a configuration in which the absorbent member 10 is attached to the elastic sheet 17, the pressing force of the chassis 20 and the pressing force of the elastic sheet 17 both acts against the absorbent member 10 to press the absorbent member 10 reliably against the wearer.

Figure 21:
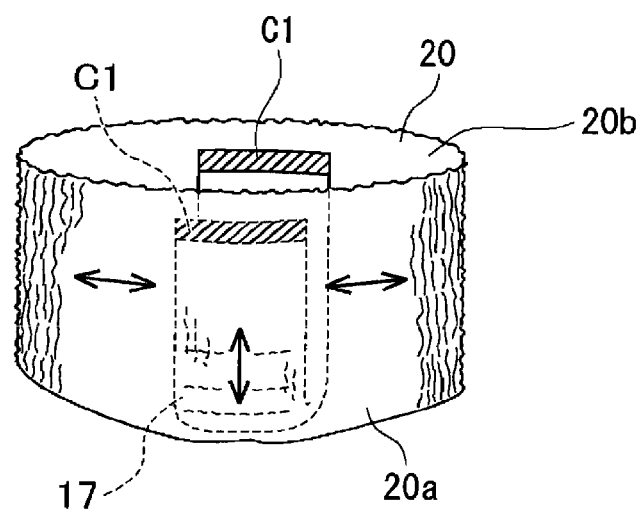
FIG. 21 illustrates a variation of how the elastic sheet 17 is attached.

FIG. 21 illustrates an example in which the end portions of the elastic sheet 17 are joined to the chassis 20 at a position, joined portions C1, that is higher than in the configuration illustrated in FIG. 2. When the wearer P wears the disposable garment 1 with a configuration in which the absorbent member 10 is attached, the elastic force of the elastic sheet 17 and the elastic force of the chassis 20 both act against the wearer P to reliably press the absorbent member 10 against the wearer side. The elastic sheet 17 may be joined to the chassis 20 at a position higher than the central portion or lower than the central portion. As illustrated in FIG. 2, by joining the elastic sheet 17 to the front portion and the back portion of the chassis 20 so that the elastic sheet 17 extends between portions thereof located lower than the central portions, the pressing force of the elastic sheet 17 can be made weaker than in a configuration in which the elastic sheet 17 is joined at portions located centrally or higher than the central portions. This results in a product suitable for wearers indisposed to having the absorbent member 10 strongly pressing against the body side. In configurations in which the elastic sheet 17 is joined to the chassis 20 at a portion lower than the central portion, the absorbent member 10 can be pushed strongly against the body side and the length of the elastic sheet 17 can be made shorter. Thus, the production cost of the elastic sheet 17 can be reduced.

Figure 22A:
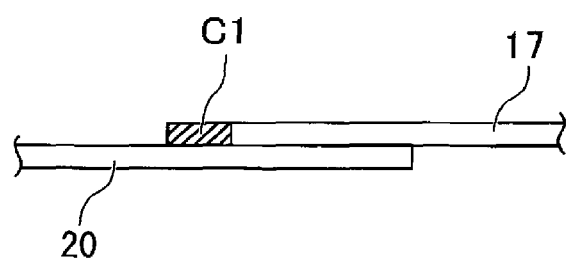
FIGS. 22A and 22B are cross-sectional views illustrating a joined portion of the elastic sheet 17 with the members overlapping.
Figure 22B:
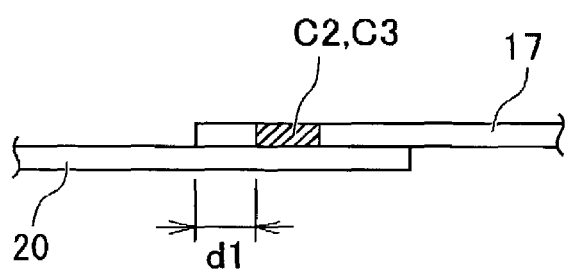

FIGS. 22A and 22B illustrate the elastic sheet 17 and the chassis 20 in joined states. In FIG. 22A, the portion where the end edge portion of the elastic sheet 17 and the chassis 20 joins is defined as the joined portion C1. In FIG. 22B, the position spaced an interval d1 away from the end edge portion of the elastic sheet 17 where the elastic sheet 17 and the chassis 20 joins is defined as joined portion C2 (or C3). In such a manner, the configuration can be changed to achieve the suitable elastic force.

FIGS. 23A to 23F illustrate variations of how the elastic sheet 17 is attached to the chassis 20. FIG. 23A illustrates a configuration in which the end portions of the elastic sheet 17 are joined to the chassis 20 at the joined portions C1.

FIG. 23B illustrates a configuration in which the elastic sheet 17 is joined to the chassis 20 at the joined portions C2, which are positions spaced the interval d1 away in the longitudinal direction from the end portions of the elastic sheet 17. The interval d1 in the longitudinal direction of the elastic sheet 17 is preferably set so that the suitable elastic force can be obtained between the joined portion C2 of the front end and the joined portion C2 on the back end.

FIG. 23C illustrates a configuration in which the elastic sheet 17 is joined at the spot-shaped joined portions C3, which are positions spaced the interval d1 away from the end portions of the elastic sheet 17. The number of spot-shaped joined portions C3 may be one or three or more.

FIG. 23D illustrates a configuration in which the elastic sheet 17 is joined at the spot-shaped joined portions C3, which are positions spaced the interval d1 away from the end portions of the elastic sheet 17, and spot-shaped joined portions C4, which are positions spaced an interval d2 away in the longitudinal direction from the joined portions C3. In such a configuration, the elastic sheet 17 is joined at the joined portions C3, C4 while being stretched in the longitudinal direction. When the elastic sheet 17 is released from this stretched state, in the longitudinal direction of the elastic sheet 17, elastic force is obtained between the front end joined portions C4 and the back end joined portions C4.

As long as the elastic sheet 17 is attached with the amount of elastic force required by the elastic sheet 17 ensured, the elastic sheet 17 can be attached to the chassis 20 at a discretionary position. Of the methods of attaching the elastic sheet 17 to the chassis 20 described above, attaching the elastic sheet 17 at the positions illustrated in FIG. 23A is preferable.

In a configuration in which the elastic sheet 17 is a separate member from the chassis 20 and attached thereto, by attaching an absorbent member to the elastic sheet 17, the absorbent member 10 can be supported in a state independent of the chassis 20. Thus, compared to a configuration in which the absorbent member 10 is integrally joined to the chassis 20, the absorbent member 10 does not shift from a predetermined position thereof in relation to the body and no gaps are formed between the absorbent member 10 and the body even when the chassis 20 moves due to the body movement of the wearer when he/she is walking, for example. Also, the absorbent member 10 is further reliably put in contact with the body and leakage of sweat and urine is effectively prevented.

As illustrated in FIG. 23E, the elastic sheet 17 may be joined to the chassis 20 in the central portion in the width direction at a line-shaped joined portion C5 that extends in the longitudinal direction.

The elastic sheet 17 illustrated in FIG. 23F is joined to the chassis 20 in the central portion in the width direction at a plurality of circular joined portions C6 disposed along the longitudinal direction. In such a configuration, the plurality of joined portions C6 are intermittently provided. This allows the stretchability in the longitudinal direction of the elastic sheet 17 between adjacent joined portions C6 to be maintained.

Figure 24A:
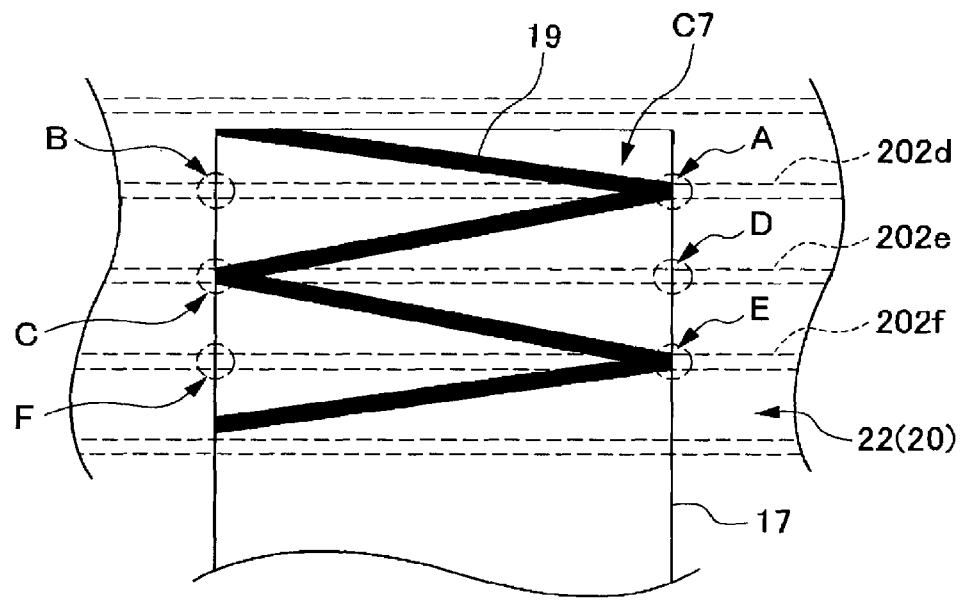
FIGS. 24A and 24B illustrate other variations of how the elastic sheet 17 is attached.
Figure 24B:
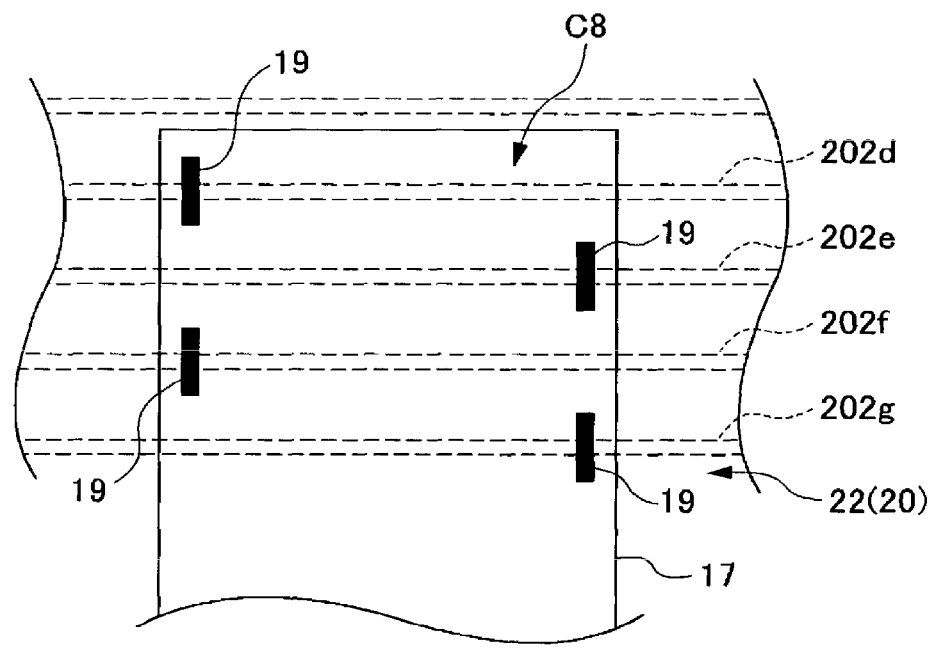

FIGS. 24A and 24B illustrate another variation of a method of attaching the elastic sheet 17 to the chassis 20. Additionally, the elastic sheet 17 is joined to the air permeable sheet 203 disposed on the side of the chassis 20 proximal to the body. Linear elastic bodies 202d to 202f are disposed on the back surface side which is the side opposite to the body side of the air permeable sheet 203.

In the example illustrated in FIG. 24A, the elastic sheet 17 is joined to the chassis 20 by a hot-melt adhesive 19 which is applied in a zigzag-like manner diagonally between adjacent linear elastic bodies of the linear elastic bodies 202d to 202f disposed in the chassis 20. The elastic sheet 17 is joined to the chassis 20 with the hot-melt adhesive 19 at a region A corresponding to the linear elastic body 202d, a region C corresponding to the linear elastic body 202e, and a region E corresponding to the linear elastic body 202f. This allows the stretchability of the linear elastic bodies in the chassis 20 to be maintained.

In the example illustrated in FIG. 24B, the end portion of the elastic sheet 17 is joined at one point at a position that overlaps the linear elastic body disposed in the chassis 20, and for adjacent linear elastic bodies, the joining position with the end portion of the elastic sheet alternates between both end portions of the elastic sheet. The elastic sheet 17 is joined at points positioned on each of the linear elastic bodies in the chassis 20. This allows the stretchability of the chassis 20 to be maintained without any loss to the elastic force of the linear elastic bodies.

In the example illustrated in FIG. 24B, for each linear elastic body, the stretchability is maintained from the region where the elastic sheet 17 is joined with the hot-melt adhesive 19 toward the region where the hot-melt adhesive 19 is not applied. Additionally, by the region between two adjacent linear elastic bodies not being joined with the hot-melt adhesive 19, in the chassis 20, the flexibility in the lateral direction and the vertical direction of the paper sheet or nonwoven fabric disposed between the two adjacent linear elastic bodies is maintained.

Figure 25:
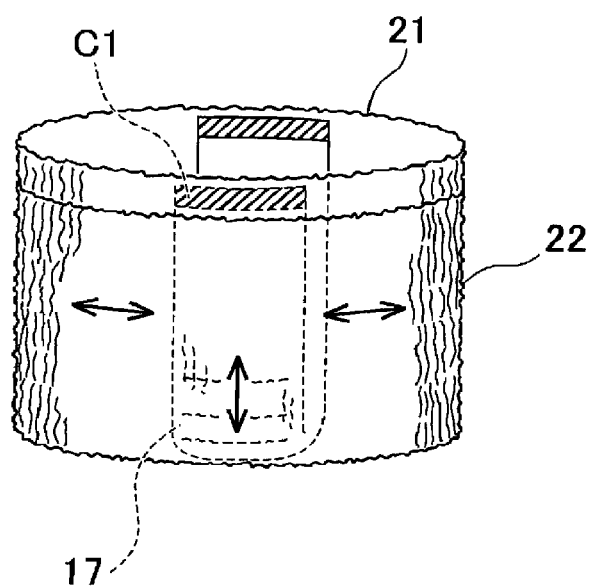
FIG. 25 illustrates a variation of how the elastic sheet 17 is attached.

The elastic sheet 17 is not limited to being attached to the chassis 20 and may be attached to the torso band 21 as illustrated in FIG. 25. In such a configuration, when the wearer P wears the disposable garment 1, the portion where the elastic sheet 17 and the torso band 21 overlap is pushed against the wearer P by the torso band 21. This improves the stability by allowing the elastic sheet 17 to push against the wearer without being twisted.

Other Example of Methods of Joining the Elastic Sheet

Figure 27D:
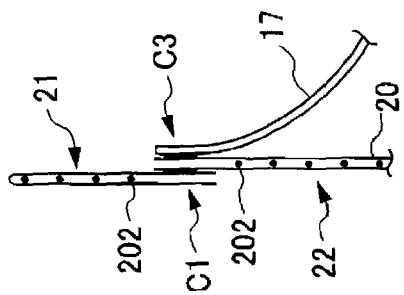
FIGS. 27A to 27D illustrate other variations of how the elastic sheet 17 is attached.
Figure 27C:
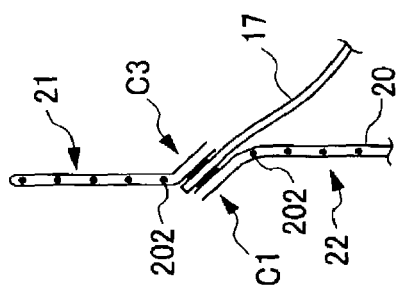
Figure 27B:
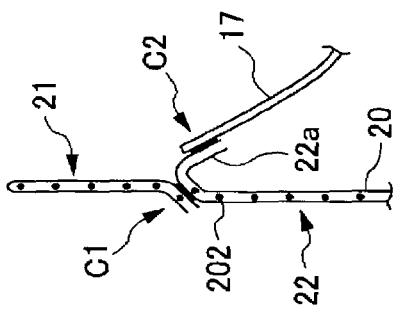
Figure 27A:
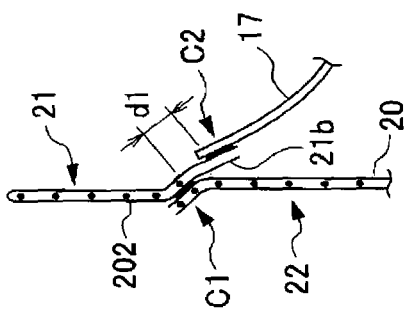
Figure 28A:
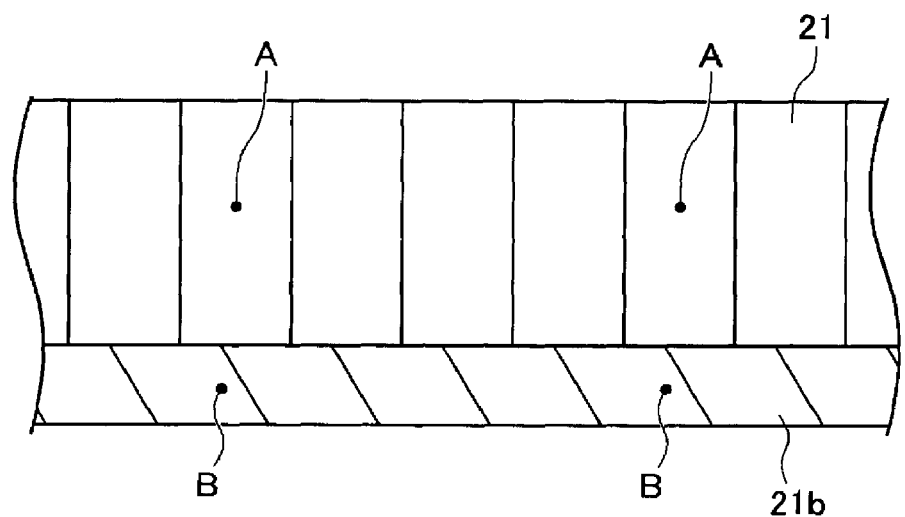
FIGS. 28A and 28B are diagrams for explaining the positions where the elastic sheet 17 of the configuration illustrated in FIG. 18B is attached.
Figure 28B:
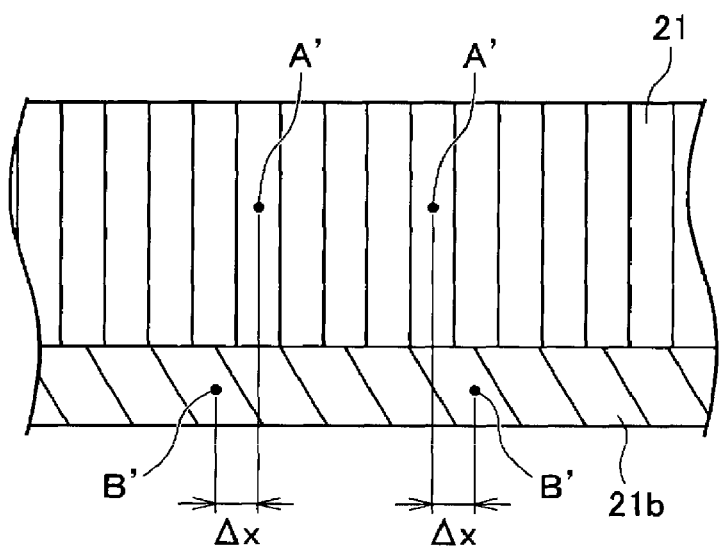

FIGS. 26A to 26H and FIGS. 27A to 27D illustrate other variations of how the elastic sheet 17 is attached. In FIGS. 26A to 26H and FIGS. 27A to 27D, the side on which the elastic sheet 17 is located is the side proximal to the body. Additionally, FIGS. 28A and 28B are diagrams for explaining the positions where the elastic sheets 17 of the configurations illustrated in FIGS. 27A to 27D are attached. An example in which the air permeable sheets are nonwoven fabrics is used in the explanation below.

In the embodiments illustrated in FIG. 26A, the torso band 21 and the chassis 20 are joined at the joined portion C1, and an extended portion 21b of the torso band 21 and one end of the elastic sheet 17 are joined at the joined portion C2. The extended portion 21b to which the end portion of the elastic sheet 17 is joined may be provided with the linear elastic bodies 202 or may not. As illustrated in FIG. 27A, the extended portion 21b not provided with the linear elastic bodies 202 may be joined to the elastic sheet 17.

Below, the attaching position of the elastic sheet 17 will be described in reference to a configuration in which the linear elastic bodies 202 have been removed from the extended portion 21b.

FIGS. 28A and 28B are schematic views of the torso band 21 and the extended portion 21b of the torso band 21 as viewed from the side proximal to the body. In configurations in which the elastic sheet 17 is joined to the torso band 21 (see FIG. 25 for example), the elastic sheet 17 and the torso band 21 are joined with the torso band 21 being stretching to the maximum extent in the lateral direction. This is because if the torso band 21 and the elastic sheet 17 are joined with the torso band 21 in an unstretched state (hereinafter referred to as "returned state"), when the torso band 21 is stretched in the lateral direction, the allowance for elongation of the torso band 21 is decreased in proportion to the width of the elastic sheet 17. Thus, when the torso band 21 and the elastic sheet 17 are joined, by joining the torso band 21 and the elastic sheet 17 with the torso band 21 being stretched to the maximum extent in the lateral direction, the expansion and contraction effect of the torso band 21 can be effectively used.

As illustrated in FIG. 27A, when the extended portion 21b without the linear elastic bodies and the elastic sheet 17 are joined, the torso band 21 and the elastic sheet 17 are preferably not joined with the torso band 21 being stretched in the lateral direction. As illustrated in FIG. 28A, with the torso band 21 being stretched to the maximum extent in the lateral direction, discretionary points A-A on the torso band 21 and points B-B at the same position of the extended portion 21*b* may be set. As illustrated in FIG. 28B, putting the torso band 21 from this state to the returned state results in the interval between the points A'-A' set on the torso band 21 and the interval between points B'-B' set on the extended portion 21*b* deviating by the amount Δx. Because the extended portion 21*b* is not provided with the linear elastic bodies 202, the expansion and contraction effect of the extended portion 21*b* is less than that of the torso band 21. Such a deviation may form lines in the end portions of the elastic sheet 17, with such lines degrading the contact of the elastic sheet 17 with the wearer. By joining the extended portion 21*b* without the linear elastic bodies and the elastic sheet 17 with the torso band 21 in an unstretched state, the end portion of the elastic sheet 17 does not contract even if the torso band 21 contracts and lines are not formed on the elastic sheet 17. As a result, gaps between the elastic sheet 17 and the wearer can be prevented from forming and the elastic sheet can be reliably made to contact the wearer.

When the disposable garment 1 is one size (free-size), the garment may be worn with the torso band 21 at any state between the most stretched state and the least stretched state. Thus, when the wearer has a large waist measurement, the deviation is small, and the smaller the waist of the wearer the greater the deviation becomes. As such, joining the torso band 21 and the elastic sheet 17 with the torso band 21 in a stretched state in the lateral direction results in the feel being different from wearers of different body shapes. In particular, for wearers with small waists, a large deviation causes gaps to easily form in the width direction of the elastic sheet 17 when the legs are moved, which degrades the contact with the wearer. However, as illustrated in FIGS. 27A to 27D, in configurations in which the elastic sheet 17 is joined with the extended portion 21*b* of the torso band 21 where the linear elastic bodies have been removed, the change in the amount of deviation depending on the size of the waist of the wearer is suppressed to a minimal amount. Accordingly, when the garment is worn by a wearer with a small waist, the amount of deviation is kept small. As a result, gaps are unlikely to form in the lateral direction of the elastic sheet 17 due to leg movement and contact is enhanced. This allows a one size disposable garment 1 to be provided that has a superior feel for wearers of various body shapes. FIGS. 27B to 27D are explained in comparison to the corresponding configurations in FIGS. 26A to 26H.

In the embodiments illustrated in FIGS. 26A, 26B, 26D, and 26H, the interval dl from the joined portion C1 of the torso band 21 and the chassis 20 to the joined portion C2 of the elastic sheet 17 and the torso band 21 or the chassis 20 is preferably 3 mm or more. By the interval d1 being 3 mm or more, in configurations in which the joined portion C2 is formed via thermal sealing, any affect due to heat on the linear elastic bodies disposed in the torso band 21 or the chassis 20 located near the joined portion C2 can be suppressed.

In the configuration illustrated in FIG. 26A, the extended portion 21*b* of the torso band 21 is formed on the side proximal to the body of the joined portion C1 of the torso band 21 and the chassis 20, and the end portion of the elastic sheet 17 is joined to the extended portion 21*b* at the joined portion C2.

In the configuration illustrated in FIG. 26B, a nonwoven fabric 215 located on the side of the torso band 21 proximal to the body includes the extended portion 21*b* extending from the joined portion C1 of the torso band 21 and the chassis 20, and the end portion of the elastic sheet 17 is joined to the extended portion 21*b* at the joined portion C2.

In the configuration illustrated in FIG. 26C, the upper end of the chassis 20 extends to the side proximal to the body beyond the joined portion C1 of the torso band 21 and the chassis 20 to form an extended portion 22*a*. The end portion of the elastic sheet 17 is joined to the extended portion 22*a* at the joined portion C2. The extended portion 22*a* may not be provided with linear elastic bodies 202 as illustrated in FIG. 26B.

In the configuration illustrated in FIG. 26D, a nonwoven fabric 225 located on the outer side of the chassis 20 includes the extended portion 22*a* extending toward the side proximal to the body from the joined portion C1 of the torso band 21 and the chassis 20. The end portion of the elastic sheet 17 is joined to the extended portion 22*a* at the joined portion C2.

In the configuration illustrated in FIG. 26E, the end portion of the elastic sheet 17 is disposed sandwiched by a portion where the end portion of the torso band 21 and the end portion of the chassis 20 overlap and is joined at the joined portion C3. The overlap portion of the end portions of the torso band 21 and the end portions of the chassis 20 may have the end portion of the chassis 20 on the side proximal to the body. As illustrated in FIG. 27C, at the overlap portion, the end portions of the torso band 21 and the end portions of the chassis 20 may not be provided with linear elastic bodies 202.

In the configuration illustrated in FIG. 26F, at the joined portion C1 of the torso band 21 and the chassis 20, the end portion of the elastic sheet 17 is joined at the joined portion C3 on the side of the chassis 20 proximal to the body. In such a configuration, as illustrated in FIG. 27D, the end portions of the torso band 21 and the end portions of the chassis 20 at the joined portion C1 may not be provided with linear elastic bodies 202.

In the configuration illustrated in FIG. 26G; the nonwoven fabric 225 on the outer side and a nonwoven fabric 226 on the side proximal to the body are joined at the joined portion C1 and the torso band 21 and the chassis 20 are integrally formed. At the position of the joined portion C1, the end portion of the elastic sheet 17 is joined to the nonwoven fabric 226 on the side proximal to the body at the joined portion C3.

In the configuration illustrated in FIG. 26H, the torso band 21 and the chassis 20 are integrally formed. At the upper end of the torso band 21, the nonwoven fabric 225 on the outer side extends further than the nonwoven fabric 226 on the side proximal to the body and folds over to the side proximal to the body and is joined with the nonwoven fabric 226 on the side proximal to the body at the joined portion C1. The extended portion 22*b* that extends beyond the joined portion C1 and the end portion of the elastic sheet 17 are joined at the joined portion C2. The position of the joined portion C1 where the folded over nonwoven fabric 225 is joined with the nonwoven fabric 226 on the side proximal to the body may be any position whereby the interval d1 between it and the joined portion C2 can be ensured. For example, the position may be directly below the folded over portion of the nonwoven fabric 226 on the side proximal to the body.

As illustrated in FIGS. 26A to 26D and 26H, by joining the elastic sheet 17 to the extended portions 21*b*, 22*a*, even when body movement causes the torso band 21 and the chassis 20 to be pulled, the elastic sheet 17 resists movement in sync with this movement. Thus, any change in the pressing force against the body from the elastic sheet 17 is minimal, and the stretchability of the torso band 21 and the chassis 20 is not hindered in a manner similar to that of the configuration in which the elastic sheet 17 is directly joined to the torso band 21 or the chassis 20. As a result, body movement causes no twisting in the elastic sheet 17, and an excellent join can be made between the elastic sheet 17 and the absorbent member 10. This allows the contact of the absorbent member 10 with the body to be made reliable and provides excellent prevention against the reverse flow of urine. Additionally, by joining the elastic sheet 17 to the extended portion 21*b* or the extended portion 22*a*, in comparison to the configuration in which the elastic sheet 17 is directly joined to the torso band 21 and the chassis 20, the joined portion is not positioned on the outer surface and thus the joined portion does not stand out and has excellent appearance. In configurations in which the elastic sheet 17 is joined to the extended portions 21*b*, 22*a*, as illustrated, the end portion of the elastic sheet 17 may connect to the outer side (surface proximal to the body) of the extended portions 21*b*, 22*a* or, though not particularly illustrated, the end portion may connect to the inner side of the extended portions 21*b*, 22*a*, but the inner side is preferable. In configurations in which the elastic sheet 17 is joined on the inner side of the extended portion, the joined portion may be joined including an open end portion of the extended portion. However, the elastic sheet 17 is preferably joined so that the joined portion of the elastic sheet 17 is disposed on the proximal end portion side of the extended portion (side opposite the open end portion) with a gap formed between the open end portion of the extended portion and the elastic sheet 17. By the elastic sheet 17 being joined on the inner side of the extended portion so that a gap is formed between the extended portion and the elastic sheet 17, the gap between the extended portion and the elastic sheet 17 functions as a so-called urine trap portion for any urine leaked from the absorbent member. As a result, urine can be prevented from leaking out. Whether the elastic sheet 17 is joined to the outer side or the inner side of the extended portion, the extended portion joined to the elastic sheet 17 is preferably not provided with linear elastic bodies. In configurations in which the elastic sheet 17 is joined to the extended portion without linear elastic bodies, the expansion and contraction of the linear elastic bodies causing the lines in the elastic sheet 17 and twisting in the elastic sheet 17 can be minimized. As a result, the absorbent member 10 supported on the elastic sheet 17 is made resistant to the formation of lines and twists, and the absorbent member 10 can be put in reliable contact with the body.

The elastic sheet 17 may be joined in the same manner at both ends or may be joined in a different manner. By joining the elastic sheet 17 using thermal sealing, the linear elastic bodies 202 disposed in that area may be weakened. However, in the configurations illustrated in FIGS. 26A to 26D and FIGS. 27A to 27D, the linear elastic bodies 202 are not disposed in that area or the elastic sheet 17 is joined at a position so that weakened linear elastic bodies 202 have no affect on the overall stretchability. Thus, there is no affect on the pressing force of the disposable garment 1 against the body. As illustrated in FIGS. 26A to 26H and FIGS. 27A to 27D, by joining the elastic sheet 17 to the extended portion 21*b* of the torso band 21, the joined portion of the elastic sheet 17 is concealed. Thus, while a product with superior appearance can be achieved, the stretchability of the stretchable composite sheet at the joined portion of the elastic sheet 17 is not hindered, and even with the absorbent member 10 attached, the product is not perceived as different from typically undergarments.

Though FIGS. 26A to 26H and FIGS. 27A to 27D are diagrams for explaining configurations in which the elastic sheet 17 is attached, in other configurations, instead of the elastic sheet 17, the absorbent member 10 may be directly attached.

FIGS. 29A to 29F illustrate methods of attaching the elastic sheet 17 according to other embodiments. Configurations in which the elastic sheet 17 is attached to the chassis 20 at the end portion at a substantially central portion in the width direction are illustrated.

Figure 29A:
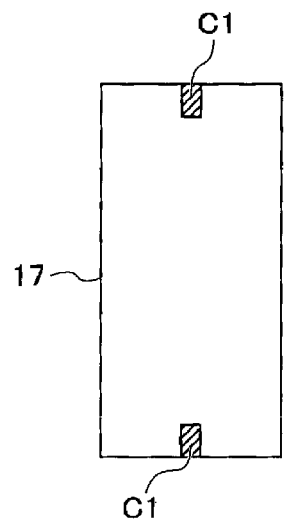
FIGS. 29A to 29F illustrate further variations of how the elastic sheet 17 is attached.

FIG. 29A illustrates a configuration in which the front end portions of the elastic sheet 17 in a substantially central portion are joined to the chassis 20 at a straight linear joined portions C1.

Figure 29B:
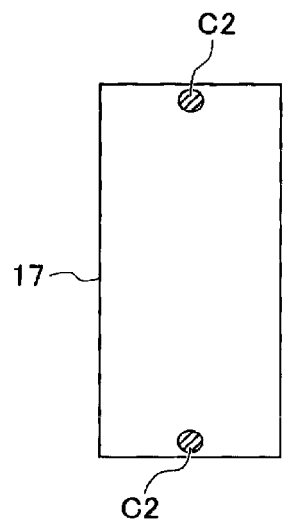

FIG. 29B illustrates a configuration in which the front end portions of the elastic sheet 17 in a substantially central portion are joined to the chassis 20 at a circular joined portions C2.

Figure 29C:
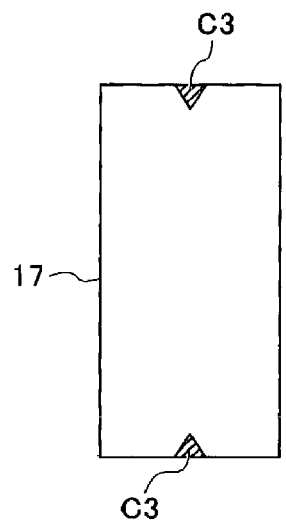

FIG. 29C illustrates a configuration in which the front end portions of the elastic sheet 17 in a substantially central portion are joined to the chassis 20 at a triangular joined portions C3.

Figure 29D:
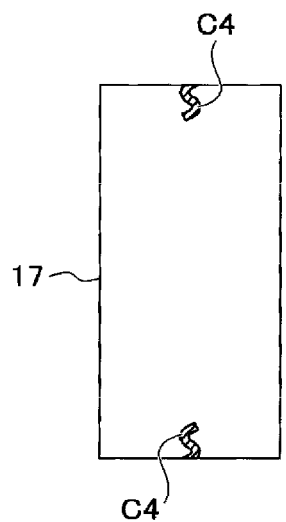

FIG. 29D illustrates a configuration in which the front end portions of the elastic sheet 17 in a substantially central portion are joined to the chassis 20 at a wave-like joined portions C4.

Figure 29E:
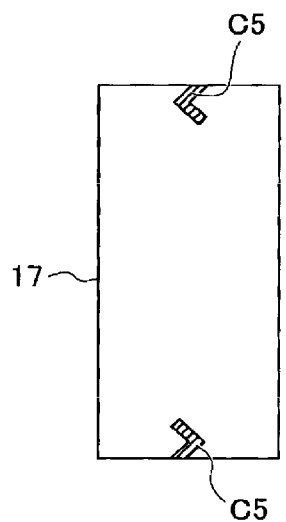

FIG. 29E illustrates a configuration in which the front end portions of the elastic sheet 17 in a substantially central portion are joined to the chassis 20 at a substantially L-shaped joined portions C5.

Figure 29F:
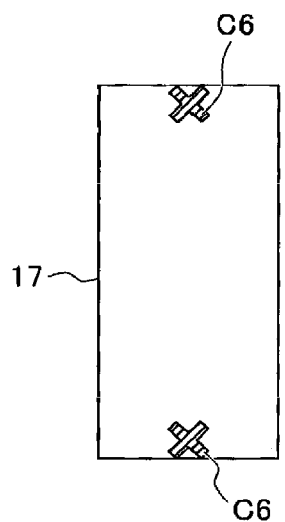

FIG. 29F illustrates a configuration in which the front end portions of the elastic sheet 17 in a substantially central portion are joined to the chassis 20 at a X-shaped joined portions C6.

In the embodiments illustrated in FIGS. 29A to 29F, the elastic sheet 17 is attached at the end portion at the substantially central portion in the width direction. This allows the contact of the disposable garment 1 with the body to be further enhanced without restricting the stretchability.

In the embodiments illustrated in FIGS. 29A to 29F, the substantially central portion of the elastic sheet 17 is joined to the chassis 20, thus irregularly shaped lateral lines are unlikely to form and localized areas of slack are unlikely to form in the chassis 20. As a result, a product superior in appearance can be achieved that is not perceived as different in appearance from typical undergarments.

In FIGS. 29A to 29F, the joined portions C1 to C6 are simply required to be attaching positions of the end portions of the elastic sheet 17 in the substantially central portion in the width direction, and the number of joined portions is not limited to one. Additionally, the shape of the joined portions is not limited to those illustrated in FIGS. 29A to 29F, and other shapes may be used and any number and combination of identical and different shape may be used. Furthermore, the joined portions C1 to C6 illustrated in FIGS. 29A to 29F may be only disposed on the front end or the back end of the elastic sheet 17, and the other joined portions may be joined like the joined portions of other embodiments (for example, the embodiment illustrated in FIG. 23A).

Figure 36:
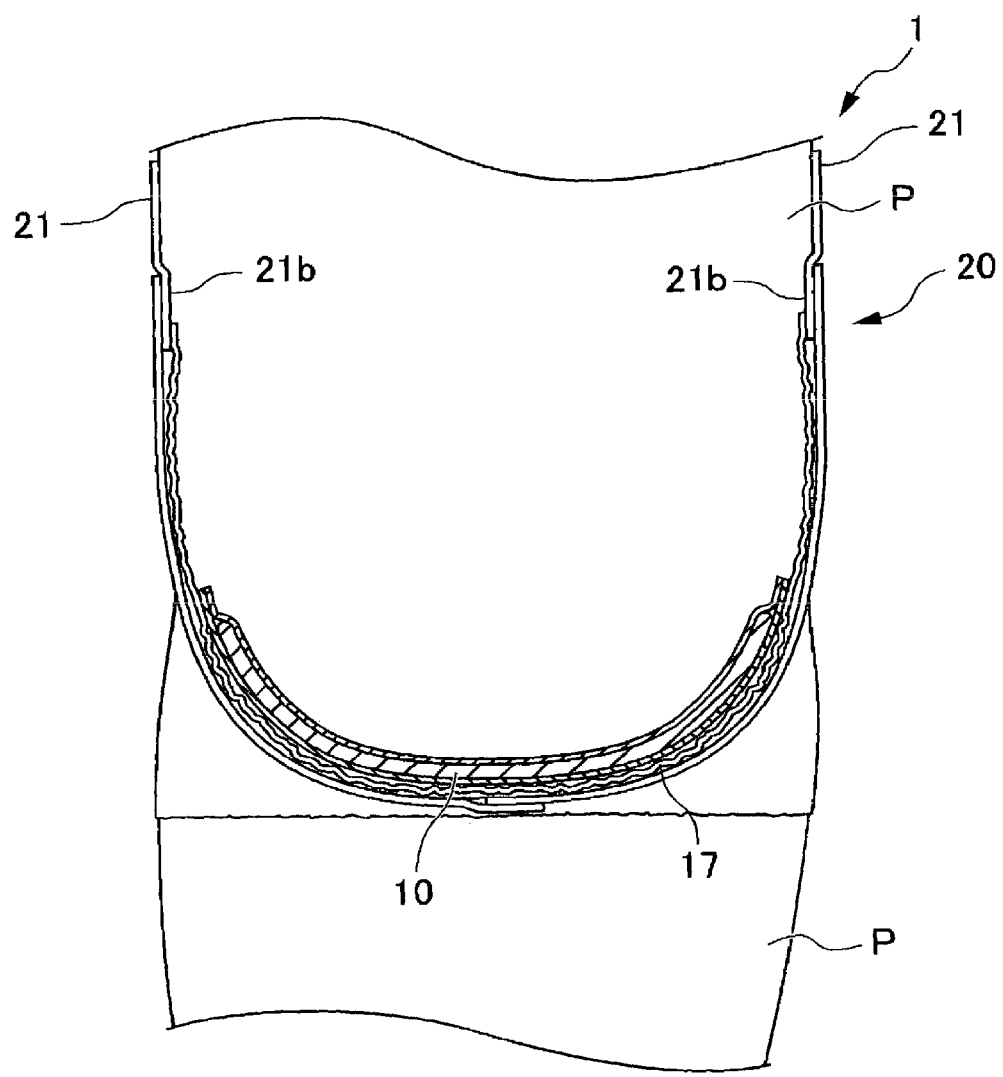
FIG. 36 is a cross-sectional view of the disposable garment 1 in which the elastic sheet 17 is joined to an extended portion 21b of the torso band 21.

FIG. 36 is a cross-sectional view of the disposable garment 1 in which the elastic sheet 17 is joined to the extended portion 21*b* of the torso band 21. As illustrated, the end portions of the front end and back end of the elastic sheet 17 are joined to the extended portion 21*b* of the torso band 21 like the configuration illustrated in FIG. 26A. By the elastic sheet 17 being joined at sections on the extended portion 21*b* and not the chassis 20, the joined section can be concealed and a superior appearance can be achieved.

Figure 30:
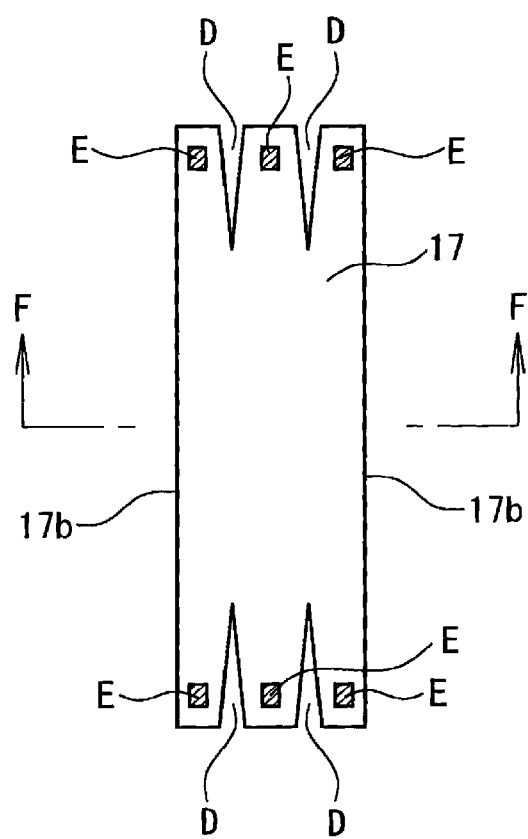
FIG. 30 illustrates another variation of how the elastic sheet 17 is attached.
Figure 31:
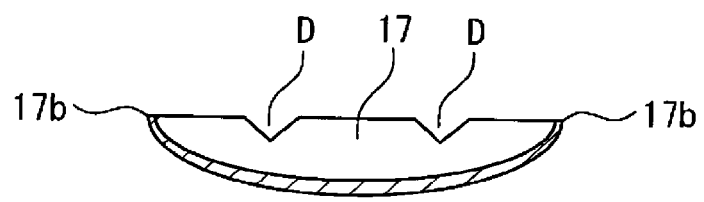
FIG. 31 is a vertical cross-sectional view along the line F-F of FIG. 30 of the elastic sheet 17 of FIG. 18E in a stretched state.

In attaching the elastic sheet 17, as illustrated in FIG. 30, the elastic sheet 17 can be provided with notches D. Joined portions E for joining the elastic sheet 17 can be disposed between the notches D. In particular, in configurations in which the elastic sheet 17 is directly attached to the chassis 20, the torso band 21, or to extended portions 21*b*, 22*a*, by providing the notches D in the elastic sheet and the joined portions E between the notches D, when the chassis 20 or the torso band 21 is stretched, the notches D open to prevent any hindrance to the extension of the chassis 20 or the torso band 21. Additionally, by attaching the elastic sheet 17 in such a manner, when the chassis 20 or the torso band 21 is stretched, the elastic sheet 17 is pulled by the chassis 20, the torso band 21, or the extended portions 21*b*, 22*a* and edge portions 17*b* of the elastic sheet 17 as illustrated in FIG. 31 is pulled upwards (the side proximal to the body) to form so-called three-dimensional gathers. This further improves the ability to prevent urine leakage. The effect of the three-dimensional gathers can be further effectively achieved by making the elastic force of the central portion of the elastic sheet 17 weaker than the elastic force of the edge portions 17*b*. Examples of methods of making the elastic force of the central portion of the elastic sheet 17 weaker than that of the edge portions 17*b* include, for example, decreasing the number of elastic members in the central portion, or changing the strength and material of the elastic members used in the central portion.

Figure 32A:
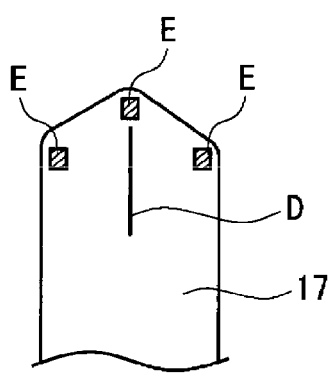
FIGS. 32A and 32B illustrate other variations of how the elastic sheet 17 is attached and illustrate the elastic sheet 17 before and after being stretched.
Figure 32B:
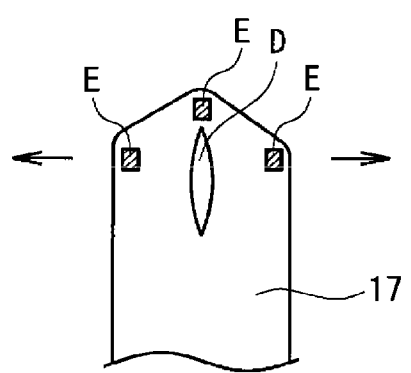

As illustrated in FIG. 32A, the elastic sheet 17 is provided with the notch D on the inner side of the end portion, and the joined portions E is disposed at positions between the substantially central portion of the end portion of the elastic sheet 17 and the notches D. The elastic sheet 17 having such a configuration may be joined. In such a configuration, when the chassis 20 or the torso band 21 is stretched, as illustrated in FIG. 32B, the notch D opens. This allows any hindrance to the elongation of the chassis 20 or the torso band 21 to be reduced.

Figure 33A:
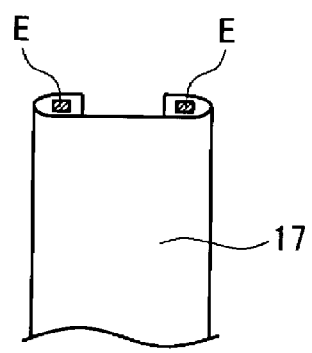
FIGS. 33A and 33B illustrate other variations of how the elastic sheet 17 is attached and illustrate the elastic sheet 17 before and after being stretched.
Figure 33B:
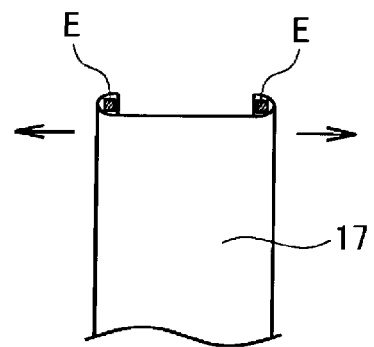

As illustrated in FIG. 33A, folded portions may be disposed on the end edge portions in the longitudinal direction of the elastic sheet 17, and the joined portions E for attaching the elastic sheet 17 may be disposed on the folded portions. In such a configuration, when the chassis 20 or the torso band 21 is stretched, as illustrated in FIG. 33B, the folded portion opens in the width direction. This allows any hindrance to the elongation of the chassis 20 or the torso band 21 to be reduced.

Figure 34A:
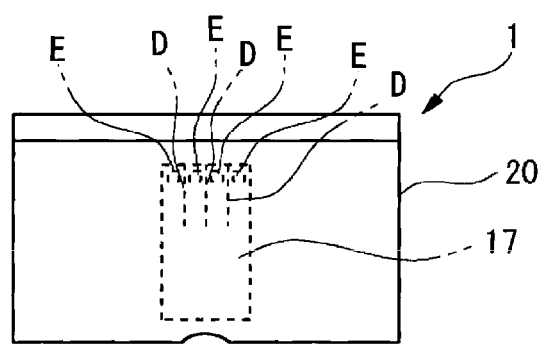
FIGS. 34A and 34B illustrate other variations of how the elastic sheet 17 is attached and illustrate the elastic sheet 17 before and after being stretched.
Figure 34B:
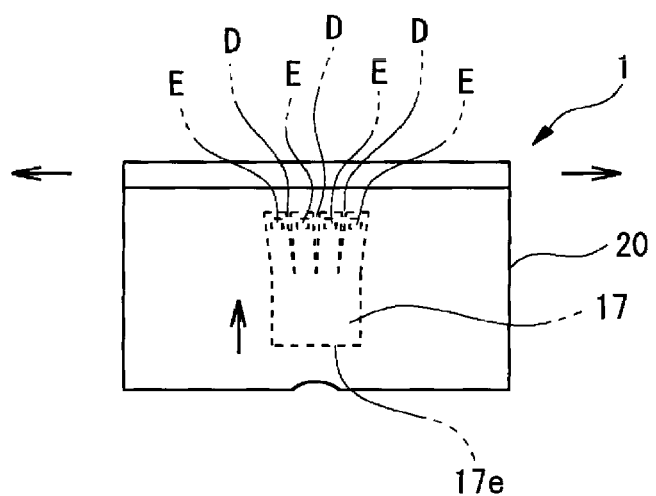

FIG. 34A illustrates the elastic sheet 17 including the notches D in the end portion attached to the chassis 20 at the joined portions E between the notches D. In such a configuration, when the disposable garment 1 is worn by the wearer and the chassis 20 is stretched, as illustrated in FIG. 34B, the notches D of the elastic sheet 17 widen and the elongation of the chassis 20 is not hindered, and a force pulls the elastic sheet 17 upward. As a result, a pressing force from the elastic sheet 17 presses against the wearer from directly below. This enhances the contact with the body.

FIGS. 35A to 35H illustrate more variations of the elastic sheet 17 that is attached to the chassis 20. FIGS. 35A to 35H illustrate variations in which, in reference to the direction in which the elastic sheet 17 is able to stretch passing through the inside leg of the wearer, at least one end portion out of the end portion regions of the elastic sheet 17 is provided with notched portions D1 to D8, the notched portions D1 to D8 making the elastic sheet 17 able to stretch freely in the width direction in response to expansion and contraction of the chassis 20 in the width direction. By providing the notched portions D1 to D8, the elastic sheet 17 is able to expand and contract in the width direction, and allows the chassis 20 to expand and contract without a loss in elasticity when the garment is worn by the wearer. In FIGS. 35A to 35H, the chassis 20 and the absorbent member 10 are not illustrated, and the elastic sheet 17 expanded flat, the notched portions D1 to D8, and joined portions E1 to E8 are illustrated.

The elastic sheet 17 illustrated in FIG. 35A is provided with a plurality of straight linear notched portions D1 in the end portion regions. The elastic sheet 17 can be joined to the chassis 20, the torso band 21, or the extended portions 21*b*, 22*a* at the joined portions E1. The elastic sheet 17 provided with the notched portions D1 in such a manner can expand and contract freely in the width direction in sync with the expansion and contraction of the chassis 20 in the width direction by the notched portions D1 opening in the width direction, despite being joined to the chassis 20 at the joined portion E1. Accordingly, by joining the elastic sheet 17 including such notches to the chassis 20 at the joined portions E1, the stretchability of the chassis 20 is made resilient to restrictions and tensions in the elastic sheet are reduced when the garment is worn by the wearer. Thus, when the garment is worn by the wearer, an aesthetically beautiful disposable garment can be provided without being perceived as different in appearance particularly in the region near the joined portions of the elastic sheet 17 and the chassis 20.

The notched portions D1 may have an elongated shape in the stretching direction of the elastic sheet 17. By the notched portions D1 having an elongated shape in the stretching direction, when the chassis 20 expands and contracts in the width direction, the notched portions D1 open in response to the expansion and contraction, allowing elastic sheet 17 to stretch freely in the width direction. Furthermore, notched portions D1 adjacent to one another are offset a predetermined length (P1) in the stretching direction. By forming the notched portions D1 offset a predetermined length (P1), the elastic sheet 17 can expand and contract better in response to the expansion and contraction in the width direction of the chassis 20.

The elastic sheet 17 illustrated in FIG. 35B has the same configuration as the elastic sheet 17 of FIG. 35A except that a plurality of notched portions D2 are formed that have a wider pitch than the notched portions D1. In a similar manner, the elastic sheet 17 can be joined to the chassis 20, the torso band 21, or the extended portions 21*b*, 22*a* at joined portions E2. The elastic sheet 17 illustrated in FIG. 35B, in a similar manner to that of the elastic sheet 17 illustrated in FIG. 35A, is provided with the notched portions D2. Thus, the elastic sheet 17 can expand and contract freely in the width direction in sync with the expansion and contraction of the chassis 20 in the width direction even if the elastic sheet 17 is joined to the chassis 20 at the joined portions E2. Accordingly, with the elastic sheet 17 including the notched portions D2 joined to the chassis 20 at the joined portions E2, the stretchability of the chassis 20 is made resilient to restrictions and tensions in the elastic sheet are reduced when the garment is worn by the wearer. Thus, due to the stretchability of the chassis not being hindered, when the garment is worn by the wearer, an aesthetically beautiful disposable garment can be provided without being perceived as different in appearance particularly in the region near the joined portions of the elastic sheet 17 and the chassis 20.

The elastic sheet 17 illustrated in FIG. 35C is provided with a plurality of straight linear notched portions D3 in substantially the entire region. Additionally, the elastic sheet 17 can be joined to the chassis 20, the torso band 21, or the extended portions 21b, 22a at joined portions E3. In such a configuration, the elastic sheet 17 is provided with the notched portions D3 substantially throughout the entire region of the elastic sheet 17. This allows the stretchability of the chassis 20 to be resilient to restrictions even when the elastic sheet 17 is joined to the chassis 20 as in the configurations described above. Thus, due to the stretchability of the chassis not being hindered, when the garment is worn by the wearer, an aesthetically beautiful disposable garment can be provided without being perceived as different in appearance particularly in the region near the joined portions of the elastic sheet 17 and the chassis 20. Additionally, by forming the notched portions D3 in substantially the entire region, even when the absorbent member is disposed on the elastic sheet when the garment is worn by the wearer, moisture is let escape and sweatiness is suppressed, providing better air permeability and the moisture permeability.

The elastic sheet 17 illustrated in FIG. 35D has the same configuration as the elastic sheet 17 of FIG. 35C in substantially the entire region, except that a plurality of notched portions D4 are formed that have a wider pitch than the notched portions D3.

Additionally, the elastic sheet 17 can be joined to the chassis 20, the torso band 21, or the extended portions 21b, 22a at joined portions E4. In such a configuration, the elastic sheet 17 is provided with the notched portions D4 substantially throughout the entire region of the elastic sheet 17. This allows the stretchability of the chassis to be resilient to restrictions even when the elastic sheet 17 is joined to the chassis 20 as in the configurations described above. Thus, due to the stretchability of the chassis 20 not being hindered, when the garment is worn by the wearer, an aesthetically beautiful disposable garment can be provided without being perceived as different in appearance particularly in the region near the joined portions of the elastic sheet 17 and the chassis 20. Additionally, by forming the notched portions D4 in substantially the entire region, even when the absorbent member is disposed on the elastic sheet when the garment is worn by the wearer, moisture is let escape and sweatiness is suppressed, providing better air permeability and the moisture permeability.

In the elastic sheet 17 illustrated in FIG. 35E, the straight linear notched portions D5 are provided in the substantially central portion of both ends. Additionally, the elastic sheet 17 can be joined to the chassis 20, the torso band 21, or the extended portions 21b, 22a at joined portions E5. In such a configuration, with the elastic sheet 17 joined to the chassis 20 in a similar manner to the configurations described above, the stretchability of the chassis 20 is made resilient to restrictions and tensions in the attachment portion of elastic sheet are reduced when the garment is worn by the wearer. Thus, due to the stretchability of the chassis not being hindered, when the garment is worn by the wearer, an aesthetically beautiful disposable garment can be provided without being perceived as different in appearance particularly in the region near the joined portions of the elastic sheet 17 and the chassis 20.

In the elastic sheet 17 illustrated in FIG. 35F, the notched portions D6 are provided in the substantially central portion of both ends. Additionally, the elastic sheet 17 can be joined to the chassis 20, the torso band 21, or the extended portions 21b, 22a at joined portions E6. In such a configuration, with the elastic sheet 17 joined to the chassis 20 in a similar manner to the configurations described above, the stretchability of the chassis 20 is made resilient to restrictions and tensions in the attachment portion of elastic sheet are reduced when the garment is worn by the wearer. Thus, due to the stretchability of the chassis not being hindered, when the garment is worn by the wearer, an aesthetically beautiful disposable garment can be provided without being perceived as different in appearance particularly in the region near the joined portions of the elastic sheet 17 and the chassis 20.

The notched portions D6 have a V-shape. A notched portion in an embodiment of the present invention is not limited to having a simple straight linear or curved linear shape and may have a shape with a so-called cutout shape as in the notched portions D6 or a hole shape (described below). By the notched portion having a cutout shape or a hole shape, when the garment is worn by the wearer, sweatiness is suppressed, and the air permeability and moisture permeability can be further improved.

In the elastic sheet 17 illustrated in FIG. 35G; the notched portions D7 are holes with an oval shape. Such a configuration has the same effects as described above with, air permeability and moisture permeability being superior. Additionally, the elastic sheet 17 illustrated in FIG. 35G can be joined to the chassis 20, the torso band 21, or the extended portions 21b, 22a at joined portions E7.

In the elastic sheet 17 illustrated in FIG. 35H, the notched portions D8 are holes with a circular shape. Such a configuration has the same effects as described above with, air permeability and moisture permeability being superior. Additionally, the elastic sheet 17 illustrated in FIG. 35H can be joined to the chassis 20, the torso band 21, or the extended portions 21b, 22a at joined portions E8.

In the above-described variations of the elastic sheet 17 illustrated in FIGS. 35A to 35H, in at least the region where the plurality of notched portions are formed, the elastic sheet 17 expands and contracts well in sync with the expansion and contraction of the chassis 20 joined at the joined portions. In such configurations, as illustrated in FIGS. 35A to 35H, the joined portions are preferably disposed on the elastic sheet 17 at end regions where expansion and contraction in the lateral direction is likely to occur. By disposing the joined portions in such a manner, a disposable garment can be achieved that include the elastic sheet 17 provided with the notched portions that expands and contracts in the width direction freely in sync with the expansion and contraction of the chassis.

According to the variations illustrated in FIGS. 35A to 35H, the stretchability of the chassis 20 is prevented from being restricted, and when the garment is worn by the wearer, localized slack or a reduction in tension caused in the chassis 20 (particularly at the joined portion with the chassis 20) by the elastic sheet is prevented from occurring. Thus, when the garment is worn by the wearer, an aesthetically beautiful disposable garment can be provided without being perceived as different in appearance particularly in the region near the joined portions of the elastic sheet 17 and the chassis 20.

Figure 37:
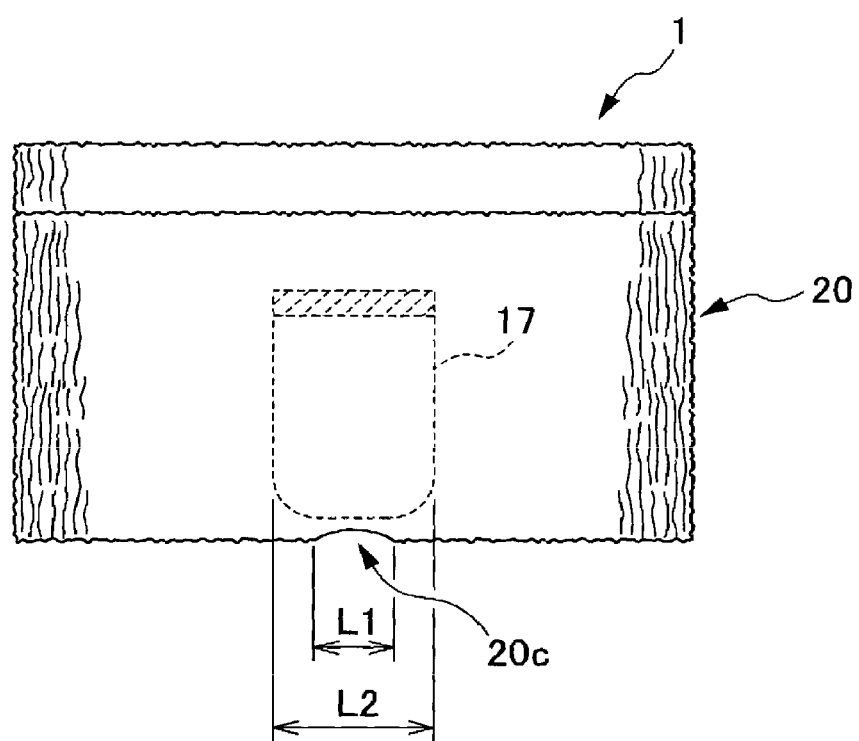
FIG. 37 is a diagram for explaining the relationship in width measurement between the elastic sheet 17 and an inside leg portion 20c.

Width Measurement of the Inside Leg Portion of the Chassis and the Elastic Sheet As illustrated in FIG. 37, in configurations in which the elastic sheet 17 is provided, a width measurement L1 of the inside leg portion 20c of the chassis 20 is preferably less than a width measurement L2 of the elastic sheet 17 joined to the chassis 20. In configurations in which the L1 is less than the L2, when the disposable garment is worn by the wearer, the inside leg portion of the chassis is raised up. This presses the bottom surface of the absorbent member 10 reliably in the direction of the body and makes the bottom surface portion of the absorbent member 10 resist movement when the chassis 20 moves due to body movement. Thus, the point that presses against the body resists being moved. In configurations in which the elastic sheet 17 is not disposed and the absorbent member 10 is directly attached, a width L1 of the inside leg portion 20c is preferably less than the width of the absorbent member 10.

Figure 38:
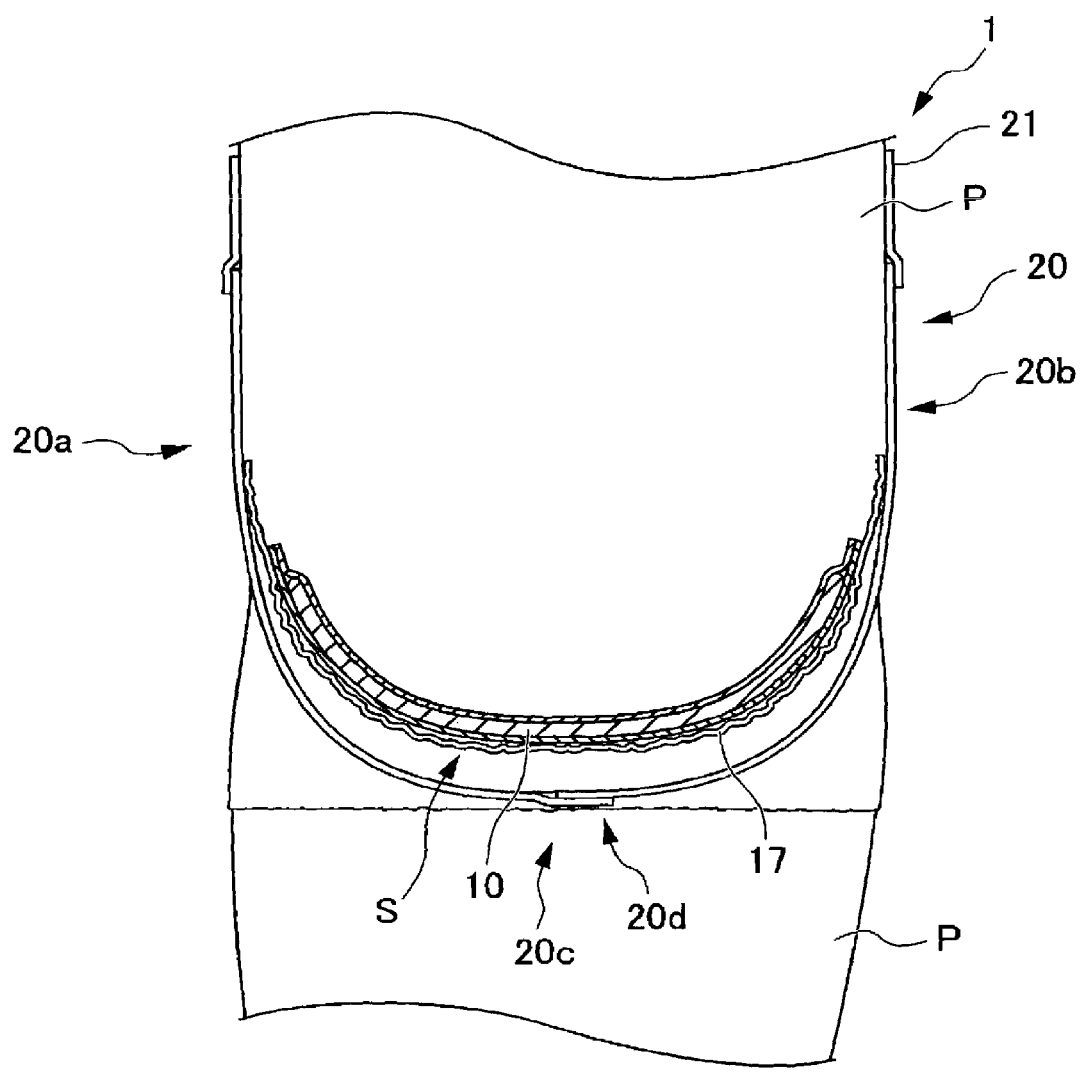
FIG. 38 is a cross-sectional view of the disposable garment 1 with a gap portion S formed in the inside leg portion 20c of the chassis 20.

FIG. 38 is a cross-sectional view of the disposable garment 1 with a gap portion S formed between the inside leg portion 20c of the chassis 20 and the elastic sheet 17. By attaching the elastic sheet 17 with the gap portion S formed between the inside leg portion 20c and the elastic sheet 17, the elastic sheet 17 is in contact further to the side proximal to the body so the pressing force from the elastic sheet 17 is more exhibited.

Method of Producing the Disposable Garment

Next, a method of producing the pants-type disposable garment 1 illustrated in FIG. 38 will be described.

Figure 39A:
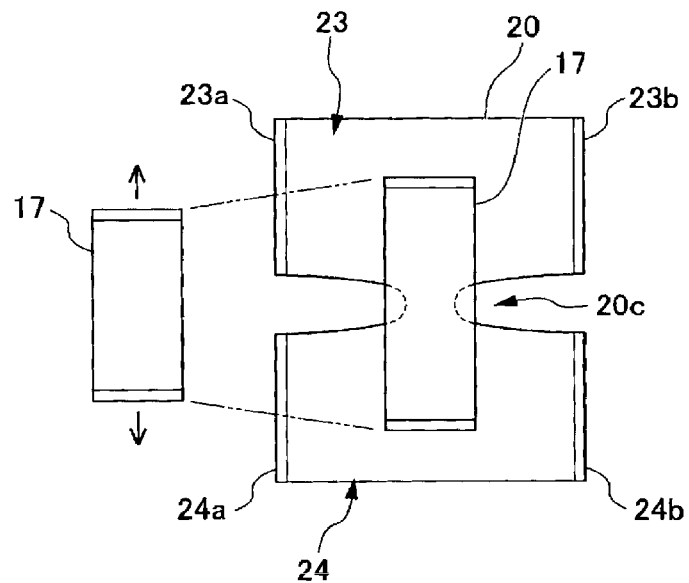
FIGS. 39A to 39C are schematic views of the production process of the disposable garment 1 deflected at the inside leg portion 20c of the chassis 20.

As illustrated in FIG. 39A, the chassis 20 prior to being formed into a pants shape includes side edge portions 23a, 23b, 24a, 24b on opposing sides in the length direction, and the side edge portions 23a, 23b, 24a, 24b are separated to each other. The elastic sheet 17 is joined to the chassis 20 with the elastic sheet 17 while the elastic sheet 17 is stretched in the longitudinal direction. In the present embodiment, the front end of the elastic sheet 17 is joined to a front portion 23 and the back end is joined to a back portion 24. By the elastic sheet 17 being joined to the chassis 20 while the elastic sheet 17 is stretched in the longitudinal direction, the elastic sheet 17 can return to an original length thereof (the length of the elastic sheet 17 illustrated on the left side of the drawing) via the stretching force of the elastic sheet 17. Because the elastic sheet 17 having returned to the original length thereof via stretching force thereof is shorter than the chassis 20 to which the front end and the back end of the elastic sheet 17 are joined while the elastic sheet 17 is stretched in the longitudinal direction, a slack portion is formed in the inside leg portion 20c.

In this state, the chassis 20 is folded in half at the inside leg portion 20c, then the side edge portion 23a of the front portion 23 and the corresponding side edge portion 24a of the back portion 24 are brought together and the side edge portion 23b of the front portion 23 and the corresponding side edge portion 24b of the back portion 24 are brought together.

Figure 39B:
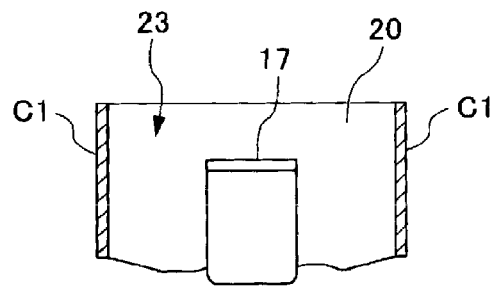

Next, as illustrated in FIG. 39B, the side edge portion 23a of the front portion 23 and the corresponding side edge portion 24a of the back portion 24 that have been brought together are joined, and the side edge portion 23b of the front portion 23 and the corresponding side edge portion 24b of the back portion 24 that have been brought together are joined. Examples of the method of joining the sheet materials to each other include joining via a hot-melt adhesive, sewing, thermal sealing, or ultrasonic bonding, using an adhesive material, or any known method. Additionally, any of these methods may be used in combination.

Figure 39C:
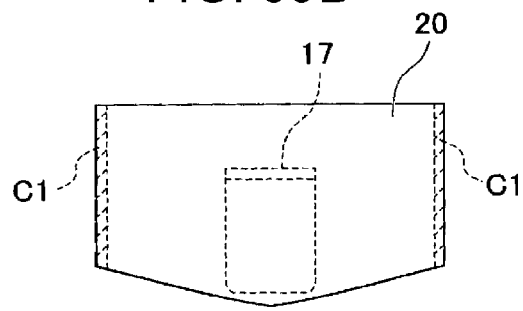

When the side edge portions are joined in such a manner, the chassis 20 is formed into a pants shape as illustrated in FIG. 39C. The formed chassis 20 has the elastic sheet 17 exposed on the outer side of the chassis 20. Additionally, on the side edges in the lateral direction (left/right direction) of the chassis 20, the joined portions C1 are exposed on the outer side.

Next, as illustrated in FIG. 39C, the chassis 20 with the elastic sheet 17 exposed on the outer side is turned inside out. By turning the chassis 20 inside out, the pants-type disposable garment 1 with the elastic sheet 17 on the inner side is completed. Additionally, by turning the chassis 20 inside out, the joined portions C1 are disposed on the inner side. Turning the chassis 20 inside out may be performed automatically or semi-automatically by a specialized device (not illustrated) or by hand.

Figure 40A:
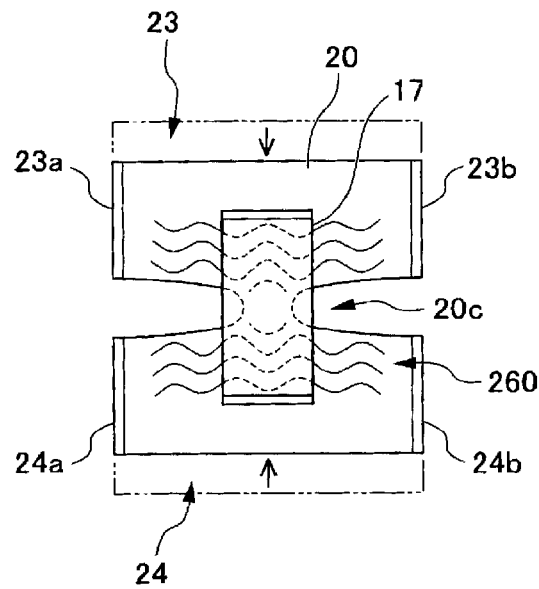
FIGS. 40A to 40C are schematic views of another production process of the disposable garment 1 deflected at the inside leg portion 20c of the chassis 20.
Figure 40B:
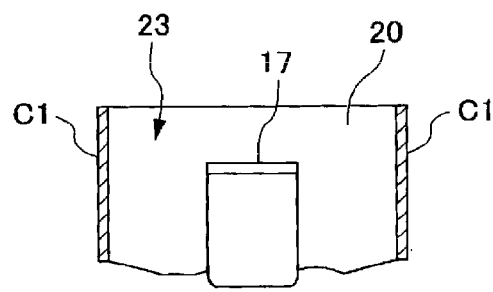
Figure 40C:
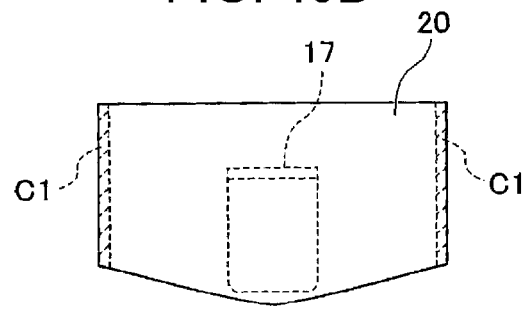

FIGS. 40A to 40C are schematic views illustrating other methods of producing the disposable garment 1 illustrated in FIGS. 39A to 39C.

As illustrated in FIG. 40A, in the present embodiment, by contracting the chassis 20 in the length direction in advance, the gap portion S is formed between the inside leg portion 20c and the elastic sheet 17. In other words, contracting the chassis 20 in the length direction forms a slack portion 260 in the inside leg portion 20c. Then, the elastic sheet 17 is joined to the chassis 20 with the slack portion 260 formed in the inside leg portion 20c while the elastic sheet 17 is not stretched.

In this state, the chassis 20 is folded in half at the inside leg portion 20c, then the side edge portion 23a of the front portion 23 and the corresponding side edge portion 24a of the back portion 24 are brought together and the side edge portion 23b of the front portion 23 and the corresponding side edge portion 24b of the back portion 24 are brought together.

Next, as illustrated in FIG. 40B, the corresponding side edge portions of the front portion 23 and the back portion 24 that have been brought together are joined and the pants shape chassis 20 is formed.

Next, as illustrated in FIG. 40C, by turning the chassis 20 with the elastic sheet 17 exposed on the outer side inside out, the pants-type disposable garment 1 with the elastic sheet 17 on the inner side is completed. Additionally, by turning the chassis 20 inside out, the joined portions C1 are disposed on the inner side.

In the embodiment illustrated in FIGS. 39A to 39C and FIGS. 40A to 40C, the front end of the elastic sheet 17 and the front portion 23 of the chassis 20 are joined and the back end of the elastic sheet 17 and the back portion 24 are joined. However, the present invention is not limited to this configuration. The position on the chassis 20 where the front end and the back end of the elastic sheet 17 are joined can be suitable set according to any of the various embodiments of the present specification.

Modified Configuration of the Chassis

Figure 41A:
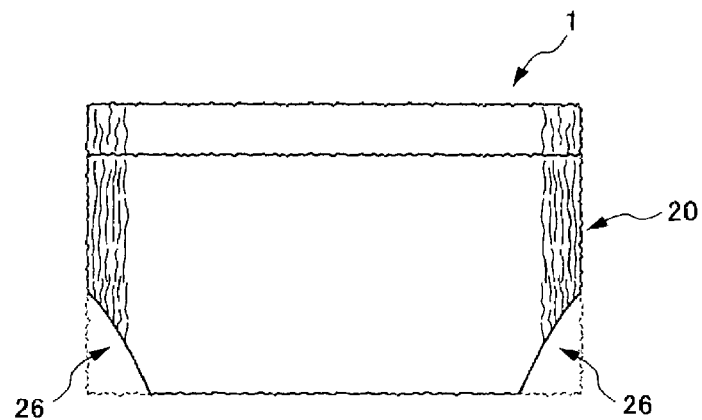
FIGS. 41A to 41C are diagrams for explaining another configuration of the chassis 20.
Figure 41B:
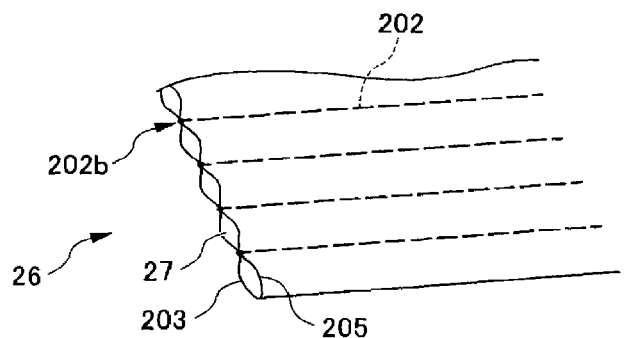

FIG. 41A illustrates the chassis 20 with a configuration in which open end portions 26 are formed on lower ends of the chassis 20 on both sides. The open end portions 26 are formed by severing the lower ends of the chassis 20 at an incline in a straight linear or curved linear manner with a cutting machine on both sides, with the chassis 20 being placed flat. By forming the open end portions 26 in the chassis 20, opening portions 27 are formed between the air permeable sheets 203, 205. This allows the air permeability to be improved. Additionally, the wearer can more easily move his/her legs. By severing the lower ends of the chassis 20 on both sides, as illustrated in FIG. 41B, in the cross section of the open end portion 26, end portions 202b of the linear elastic bodies 202 are exposed. In a configuration in which the linear elastic bodies 202 are in contact with and joined to the liquid diffusion fiber sheet 201 (not illustrated in FIGS. 41A to 41C) via the adhesive applied to the linear elastic bodies 202, and in particular in a configuration in which the anchor portions 218a are formed, because the linear elastic bodies 202 are strongly joined between the air permeable sheet 205 and the liquid diffusion fiber sheet 201, the end portions 202b of the linear elastic bodies 202 at the open end portion 26 are unlikely to withdraw inward. Thus, the stretchability at the open end portion 26 and the contact against the body are maintained.

Figure 41C:
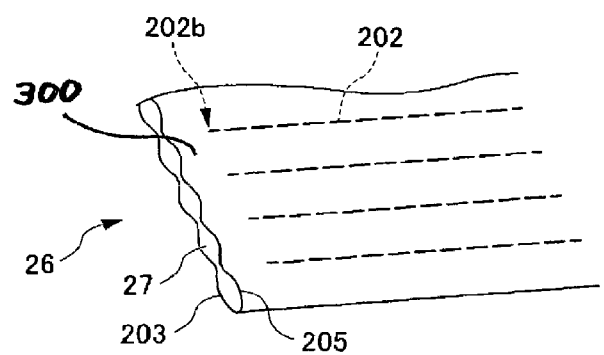

However, when a smaller amount of adhesive is applied to the linear elastic bodies 202, as illustrated in FIG. 41C, in the cross section of the open end portion 26, the end portions 202b of the linear elastic bodies 202 withdraw inward so that the linear elastic bodies 202 are not present in the cross section. The air permeable sheets 203, 205, and the liquid diffusion fiber sheet 201 are formed into a wave-like frill portion 300. The frill portion 300 is formed by the end portions 202b of the linear elastic bodies 202 becoming unadhered and withdrawing inward when the disposable garment 1 is worn by the wearer. The amount that the end portions 202b of the linear elastic bodies 202 withdraw inward at the open end portion 26 varies depending upon the degree the linear elastic bodies 202 are stretched upon the garment being worn by the wearer. The thicker the legs of the wearer, the greater the linear elastic bodies 202 are stretched. A suitable pressing force in the region near the frill portion 300 can be achieved that is commensurate to the size of the legs. When the disposable garment 1 is produced, the frill portion 300 can be formed by adding tension to the chassis 20 in the width direction and making the end portions 202b of the linear elastic bodies 202 withdraw inward.

By applying a smaller amount of adhesive to the linear elastic bodies 202, the frill portion 300 is more easily formed in the open end portion 26. The frill portion 300 allows for easier leg movement of the wearer and the wave-like appearance increases the visual appeal. Additionally, by the opening portion 27 between the air permeable sheets 203, 205 at the frill portion 300, the air permeability can be improved. The frill portion 300 can be formed by adjusting the length of the linear elastic bodies 202 in advance so that the linear elastic bodies 202 are not disposed near the open end portion 26.

Furthermore, in conventional disposable garments, for example, to achieve good contact around the legs, leg cuff gathers have been formed by disposing elastic members at the portions in contact around the legs and in particular the outermost portion of the leg opening portion. This is to prevent a degradation in contact caused by the elastic bodies falling out when the leg cuff portion is cut. Accordingly, a complicated process and multiple machines have been required to produce the leg cuff gathers. However, according to the present embodiment, the elastic bodies are prevented from falling out at the portion cut upon cutting the leg cuff portion of the chassis 20. Thus, there is no need to form leg cuff gathers. This makes complicated processes and multiple machines used for producing leg cuff gathers unnecessary, thus reducing the cost.

Absorbent Member

Figures 42A, 42B:
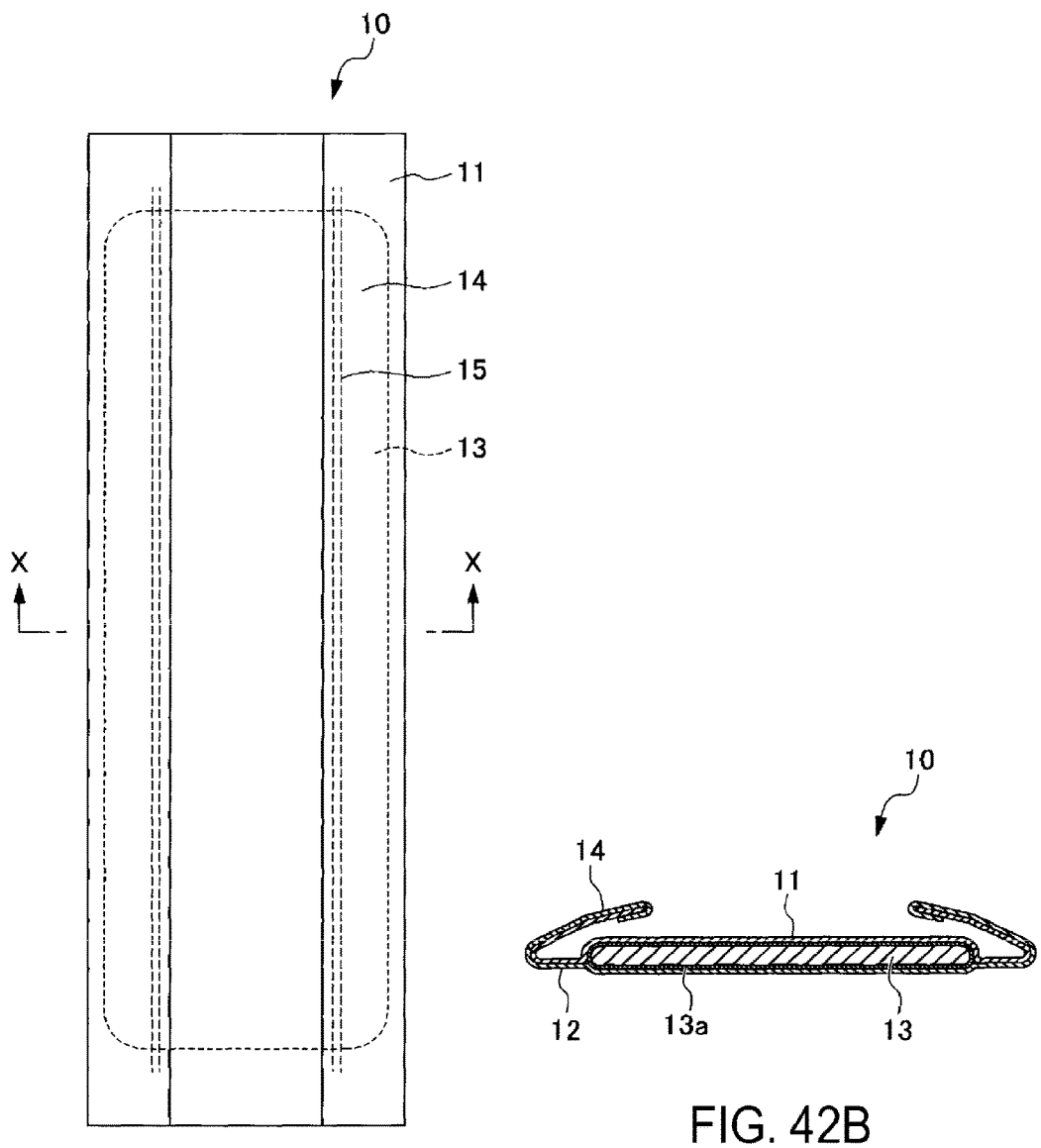
FIGS. 42A and 42B illustrate the absorbent member 10.

FIG. 42A is a plan view of the absorbent member 10. FIG. 42B is a cross-sectional view taken along line X-X of FIG. 42A.

As illustrated, the absorbent member 10 is an elongated substantially rectangular member and include a top sheet 11, a back sheet 12, an absorbent core 13 disposed between the top sheet 11 and the back sheet 12, and a fold portion 14. When the disposable garment 1 is worn by the wearer, the fold portion 14 formed on the outer portion of the absorbent member 10 (side edge portion in the width direction) becomes erect and functions as a three-dimensional side gather. The shape of the absorbent member 10 is not limited to being rectangular, and the absorbent member 10 may have an hourglass shape, an oval shape, or any known shape for an absorbent member. Additionally, the configuration of the absorbent member 10 is not limited to that described above, and the absorbent member 10 may have any known configuration.

Figure 43:
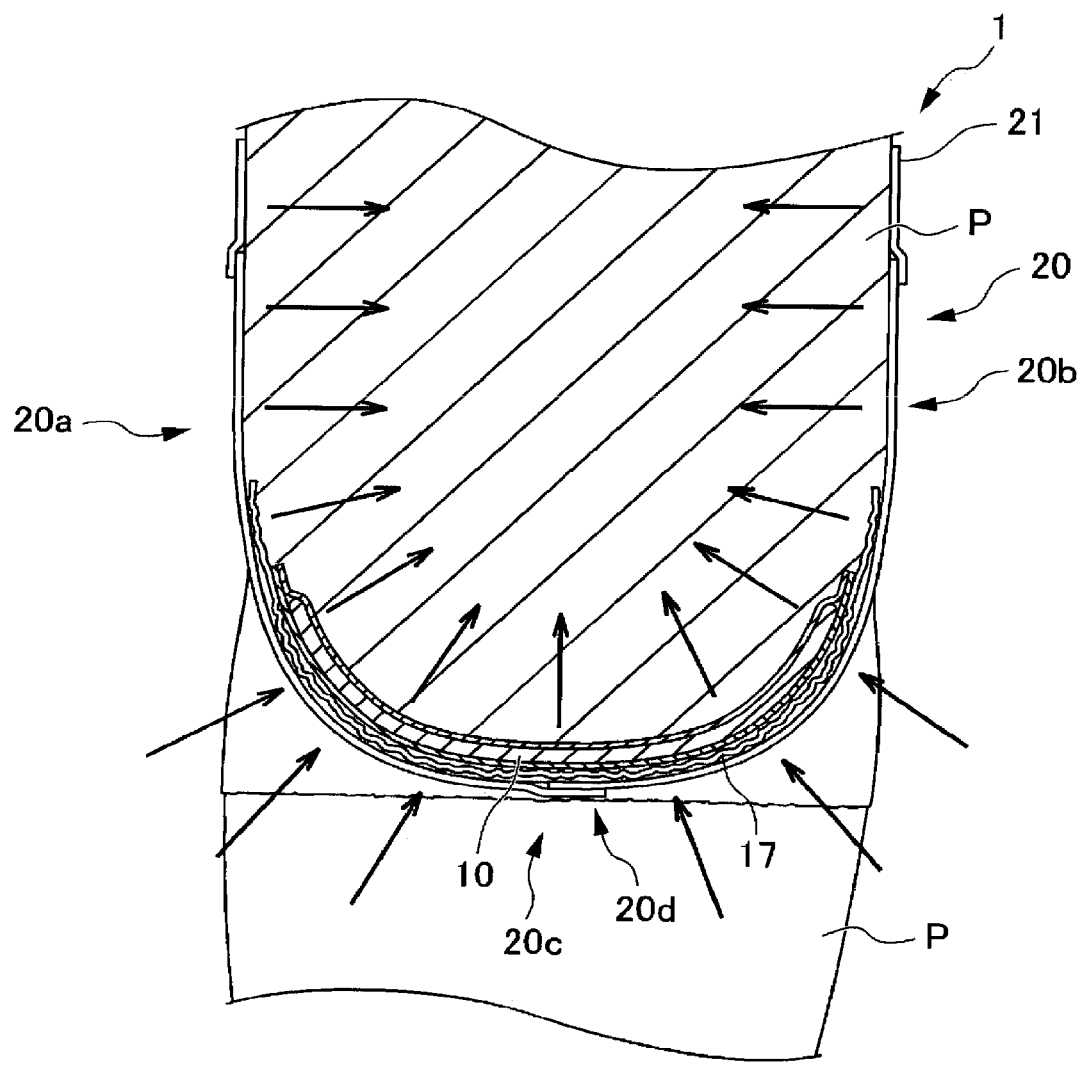
FIG. 43 is a diagram for explaining the function and effect of the disposable garment 1 according to the first embodiment.

Function and Effect (1) FIG. 43 is a diagram for explaining the function and effect of the disposable garment 1 according to the first embodiment. As illustrated, the disposable garment 1 worn by the wearer P includes the absorbent member 10 disposed on the elastic sheet 17. Accordingly, because the elastic sheet 17 can stretch, the force exerted when the elastic sheet 17 contracts presses the absorbent member 10 in the direction against the body. The pressing force in the direction against the body brings the absorbent member 10 into contact with the body. Additionally, because the chassis 20 stretches when the wearer P wears the disposable garment 1, the force exerted when the chassis 20 contracts presses the front portion 20a and the back portion 20b of the chassis 20 in the direction against the body. The strong pressing force in the direction against the body brings the chassis 20 into contact with the body.

In particular, configurations in which the absorbent member 10 is disposed on the elastic sheet 17 allow the absorbent member 10 to be pushed from directly below the inside leg. Accordingly, the absorbent member 10 has better contact with the body than conventional configurations.

The elastic sheet 17 can also be more reliably maintained in its state of being pressed toward the body side. Additionally, in the disposable garment 1 of the present embodiment, the elastic sheet 17 is pressed in the direction toward the body at the inside leg portion 20c of the chassis 20 and the region nearby. As a result, the pressing force in the direction toward the body on the elastic sheet 17 can be increased. In such a manner, in the disposable garment 1 of the present embodiment, the synergy between the contracting force of the elastic sheet 17 and the contracting force of the chassis 20 enables the chassis 20 overall and including the elastic sheet 17 to contact the body with a greater pressing force.

Figure 44A:
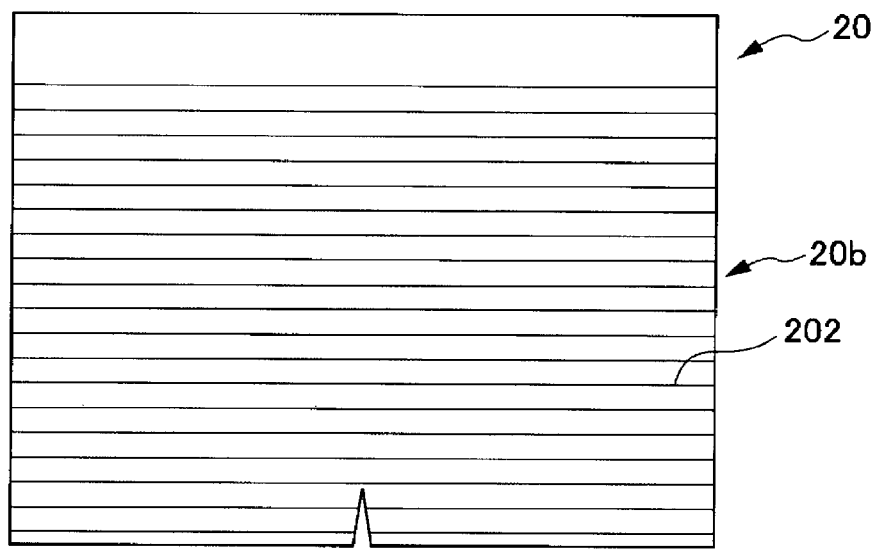
FIGS. 44A and 44B are diagrams for explaining other functions and effects of the disposable garment 1 according to the first embodiment.
Figure 44B:
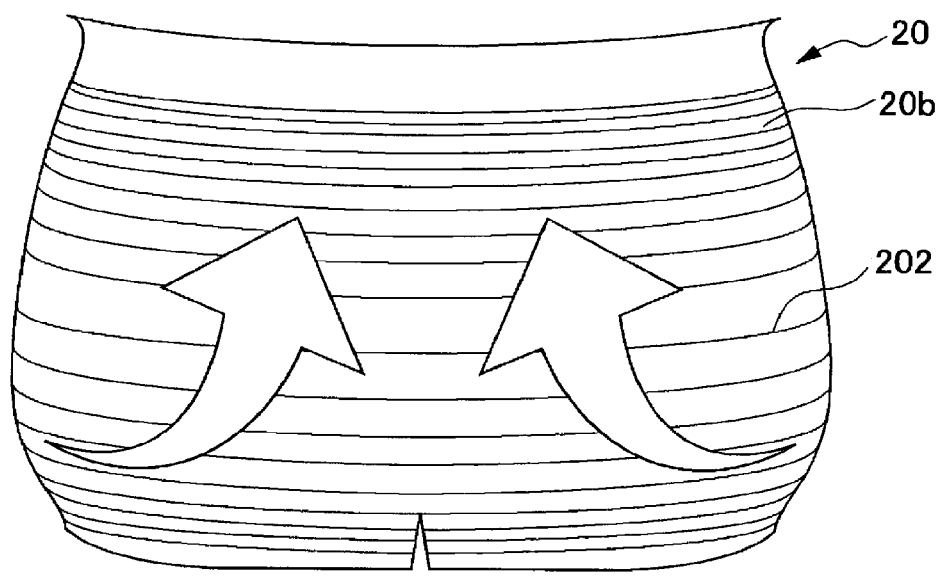

(2) As illustrated in FIG. 44A, the chassis 20 prior when the disposable garment 1 is worn by the wearer, is not changed in shape by the buttocks of the wearer, and the tension of the elastic bodies 202 at the back portion 20b is equal throughout the surface. However, as illustrated in FIG. 44B, when the disposable garment 1 is worn by the wearer, the back portion 20b of the chassis 20 changes in shape in response to the shape of the buttocks of the wearer. This change in shape results in the tension of the liner elastic bodies 202 being at a maximum at the buttocks of the wearer and decreasing in the direction towards the waist and the inside leg. The linear elastic bodies 202 disposed in the back portion 20b corresponding to the buttocks of the wearer are pulled diagonally upward from the left and right sides of the buttocks of the wearer toward the center as illustrated in the drawing by arrows. Additionally, in the back portion 20b of the chassis 20, the linear elastic bodies 202 stretched outward at the waist of the wearer attempt to return to their original state. The higher the tension of the linear elastic bodies 202 is, the stronger the restoring force is. As a result, a force pushing the buttocks of the wearer toward the center of the waist (inner side) acts and raises the buttocks of the wearer upward. This corrects sagging in the buttocks. In such a manner, the synergy between the force pulling diagonally upward the buttocks of the wearer from the left and right sides to the center, and the force pushing the buttocks of the wearer in the central direction of the waist acts on the disposable garment 1 of the present embodiment. Accordingly, the disposable garment 1 of the present embodiment can provide a bottom lifting effect such as that of shaping undergarments. Thus, though being disposable, the garment can shape the lines of the body of the wearer to appear beautiful. Furthermore, in the chassis 20 of the present embodiment, the strength of the linear elastic bodies 202 disposed in the back portion 20b is greater than the strength of the linear elastic bodies 202 disposed in the front portion 20a. Thus, the bottom lifting effect can be further increased.

Figure 45A:
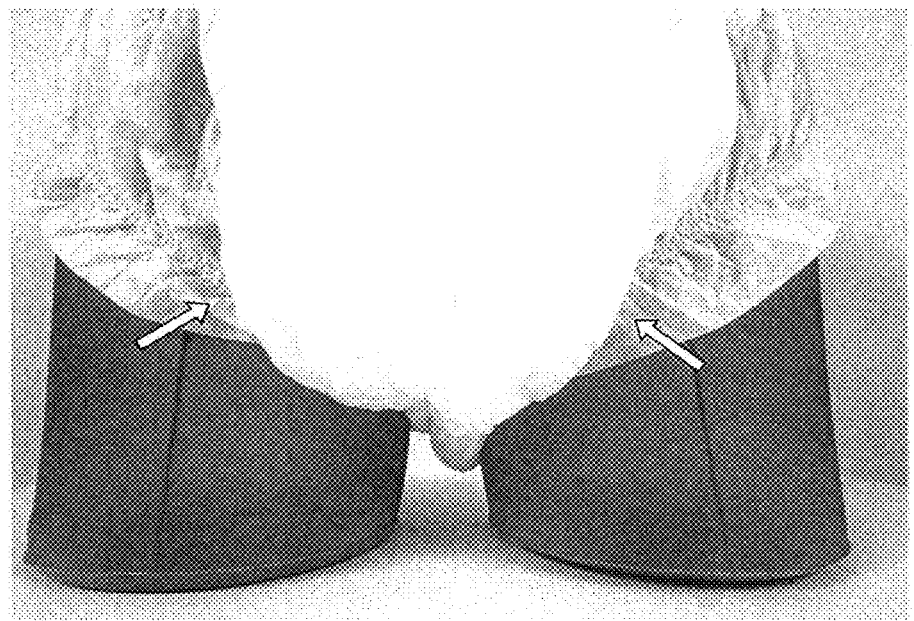
FIGS. 45A and 45B are images for explaining other functions and effects of the disposable garment 1 according to the first embodiment.
Figure 45B:
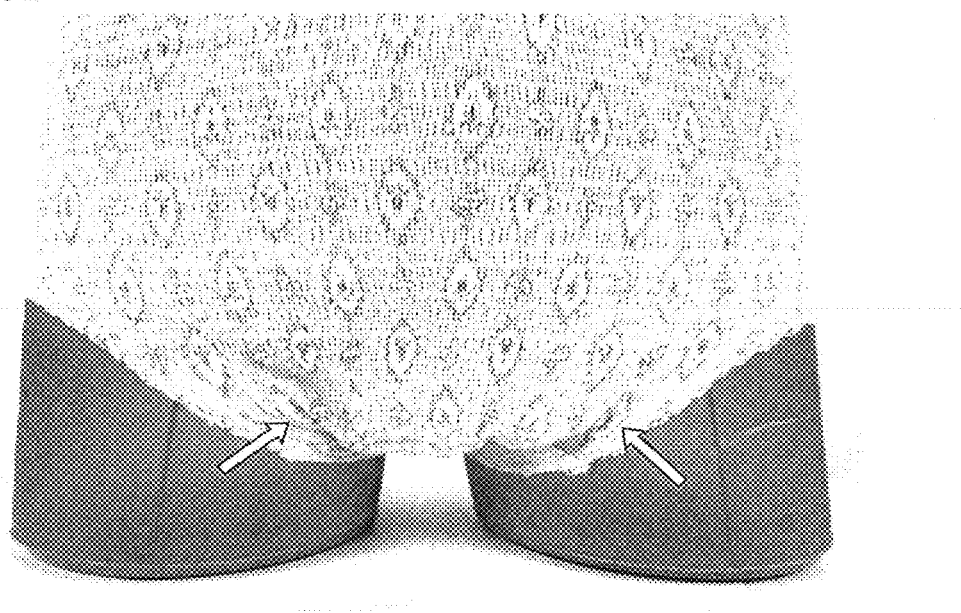

(3) FIG. 45A is an image of a conventional and typical disposable diaper as viewed from the front of the wearer. FIG. 45B is an image of the disposable garment 1 of the first embodiment as viewed from the front of the wearer.

As illustrated in FIG. 45A, the conventional and typical disposable diaper includes elastic bodies not disposed covering the absorbent member provided in the central portion. Thus, when the diaper is worn by the wearer, the elastic bodies disposed in the region around the absorbent member contract and become wedged between the absorbent member and the legs of the wearer (for example, the area indicated by the white arrows in the drawing). As a result, the absorbent member swells out from the body, thus that a disposable diaper is being worn can be noticed by other people.

Alternatively, in the disposable garment 1 of the first embodiment, the linear elastic bodies are disposed throughout the chassis 20. Thus, even when an absorbent member is attached to the elastic sheet 17, the elastic bodies do not become wedged between the absorbent member and the legs of the wearer. As can be seen in FIG. 45B, in the portion of the disposable garment 1 of the first embodiment indicated by the white arrows, there is no evident wedging of the linear elastic bodies. Accordingly, the absorbent member does not swell out from the body, thus other person is unlikely to notice that the disposable garment 1 with an absorbent member is being worn. Additionally, the product is superior in appearance and is not perceived as different in appearance from typical undergarments in terms of appearance.

(4) The disposable garment 1 of the present embodiment enables the entire chassis 20 to come into contact with the body. Thus, the chassis 20 is not caught when putting on or taking off pants or skirts to expose the skin of the wear, and other similar trouble can be avoided. Accordingly, because the body of the wearer is not subjected to localized compression such as in conventional disposable diapers that tighten around the body at the waist, a better and more stable feel can be achieved. Additionally, because the stretchability of the chassis 20 is great, the legs can be easily moved, and a one size configuration can be applied to wearers with a wide variety of body shapes. This allows a one size disposable garment 1 to be provided that has a superior feel for wearers of various body shapes.

(5) The liquid diffusion fiber sheet 201 used in the disposable garment 1 is a low cost material such as a paper sheet, and has high absorbency and quick drying ability, air permeability, hygroscopicity, and whiteness. The liquid diffusion fiber sheet 201 has thermal retention properties suitable for winter and can provide a cool sensation in summer. Additionally, the liquid diffusion fiber sheet 201 can be easily disposed of and naturally decomposes. As a result, the impact on the environment is less than that of chemical fibers. The liquid diffusion fiber sheet 201 has excellent processibility in terms of hole opening and cutting. Furthermore, the liquid diffusion fiber sheet 201 can be provided with high waterproofing ability and high surface strength via surface treatment.

(6) The humidity control effect of the liquid diffusion fiber sheet 201 enables the inside of the chassis 20 to be maintained at a suitable humidity and a suitable sense of fitting to be provided to the disposable garment 1. Additionally, with this sense of fitting, the sound of fabric rubbing together can be reduced, thus making other people less likely to realize that the disposable garment 1 is being worn. The sound of fabric rubbing together includes a "swoosh" sound made when the members of the disposable garment 1 rub against the body, a "swoosh" sound made when the members of the disposable garment 1 rub against each other, and a "swoosh" sound made when the disposable garment 1 and the pants or skirts rub against each other.

(7) The disposable garment 1 of the present embodiment includes the concave and convex portion 213 formed on the liquid diffusion fiber sheet 201. This increases the number of regions for air to pass through, thus further improving the air permeability. Additionally, by the concave and convex portion 213 being formed on the liquid diffusion fiber sheet 201, the contact area with the body is decreased. Thus, when the liquid diffusion fiber sheet 201 absorbs urine, the wearer is prevented from experiencing an uncomfortable feeling. Furthermore, by forming the concave and convex portion 213 on the liquid diffusion fiber sheet 201, though the liquid diffusion fiber sheet 201 is the same size, the surface area is increased in essence. This improves the absorbency and quick drying ability, the air permeability, the moisture permeability and the absorbency of urine.

(8) By the concave and convex portion 213 being formed on the liquid diffusion fiber sheet 201, when the adhesive is applied by spraying from a nozzle, the liquid diffusion fiber sheet 201 is not completely covered with the adhesive, but is partially covered. As a result, in configurations in which the air permeable sheet is joined to the liquid diffusion fiber sheet 201 with the adhesive, the liquid diffusion fiber sheet 201 and the air permeable sheet are joined at localized regions. This increases the flexibility of the joined composite sheet. Additionally, because more regions where the air passes through can be ensured, the thermal retention properties and the cool sensation can be further improved. In other words, by the concave and convex portion 213 being formed on the liquid diffusion fiber sheet 201, the garment can be warm in winter and cool in summer. Additionally, because more regions where the air passes through can be ensured, the humidity can be suitably adjusted.

(9) By forming the concave and convex portions 213 on the liquid diffusion fiber sheet 201, the liquid diffusion fiber sheet 201 can be given a three-dimensional feel. As a result, the disposable garment 1 can be given a more three-dimensional shape. Additionally, in configurations in which the printed layer 201a being formed on the liquid diffusion fiber sheet 201, the printed picture can be more realistic.

Additionally, in configurations in which the concave and convex portions 213 are formed on the liquid diffusion fiber sheet 201 by embossing, the paper material of the liquid diffusion fiber sheet 201 can be softer. This allows the skin comfort when the garment is worn by the wearer to be improved.

(10) Conventional paper diapers lack a force to push the absorbent member against the body and only the portion at the waist is pushed against the body. As a result, to bring the absorbent member into contact with the body, in terms of structure, the length has to be made long. As a result, when pants or a skirt are worn while the diaper is being worn by the wearer, the upper end portion of the paper diaper may appear above the pants or skirt, and other people may notice that the paper diaper is being worn. Alternatively, the disposable garment 1 of the present embodiment includes the chassis 20 with superior contact with the body. Thus, the length of the chassis 20 can be made shorter than that of conventional paper diapers. This allows the appearance and feel of the disposable garment 1 to be improved and provides an appearance which is not perceived as different from that of typical undergarments.

(11) Conventional paper diapers lack in the force that brings the absorbent member into contact with the body. Thus, for women wearing skirts, tight undergarments may also be worn over the paper diaper. However, in the disposable garment 1 of the present embodiment, tight undergarments do not need to be worn on top because the absorbent member is strongly pressed in contact with the body. As a result, the disposable garment 1 of the present embodiment is particularly suitable for women wearing skirts.

(12) The disposable garment 1 of the present embodiment, as illustrated in FIG. 38, includes the gap portion S formed under the portion where the elastic sheet 17 and the chassis 20 are joined. This allows the force for bringing the disposable garment 1 into contact with the body to be maintained while making movement of the legs easy for the wearer P. Additionally, by the gap portion S being formed, the elastic sheet 17 is easily moved in the lateral direction, making it easy for male wearers to urinate. Compared to configurations in which the elastic sheet 17 and the chassis 20 are integrally joined, in this configuration, the pressing force of the chassis 20 in the direction toward the body is greater, and the chassis 20 can more strongly press the elastic sheet 17 in the direction toward the body.

(13) By the elastic sheet 17 being able to press against the whole absorbent member 10, the urine absorbed by the absorbent member 10 readily spreads to not just the area directly in contact with the urine but also areas around it. Urine can be absorbed in a larger area in the absorbent member 10 than in conventional configurations. As a result, just one area of the absorbent member 10 absorbing the urine and swelling is not as problematic compared to conventional configurations and the appearance is improved.

Additionally, when one portion of the absorbent member 10 swells due to absorbing urine, the absorbent member 10 sags down under own weight thereof. However, the elastic sheet 17 pushes the absorbent member 10 from below and prevents the absorbent member 10 from sagging. This suppressed any decreases in appearance due to the absorbent member 10 absorbing urine and sagging.

(14) As illustrated in FIG. 43, when the disposable garment 1 is worn by the wearer, the chassis 20 with stretchability covers the wearer P from the waist to the buttocks over the elastic sheet 17, providing superior stability and fit.

(15) By the printed layer 201a such as a picture being provided on the liquid diffusion fiber sheet 201, a garment can be provided which is more beautiful in appearance than conventional paper diapers. This further reduces any reluctance of the wearer P to wear the disposable garment 1.

(16) By the lines being formed in the elastic sheet 17, the elastic sheet 17 and the absorbent member 10 are not in contact across the entire contact surface, and the elastic sheet 17 and the absorbent member 10 can be joined a number of times. The reason the elastic sheet 17 and the absorbent member 10 can be joined a number of times is that by providing lines on the elastic sheet 17, the material of the absorbent member 10 is resilient to damage. Additionally, the reason is that lines of the elastic sheet 17 make the absorbent member 10 easy to peel off.

Figure 64A:
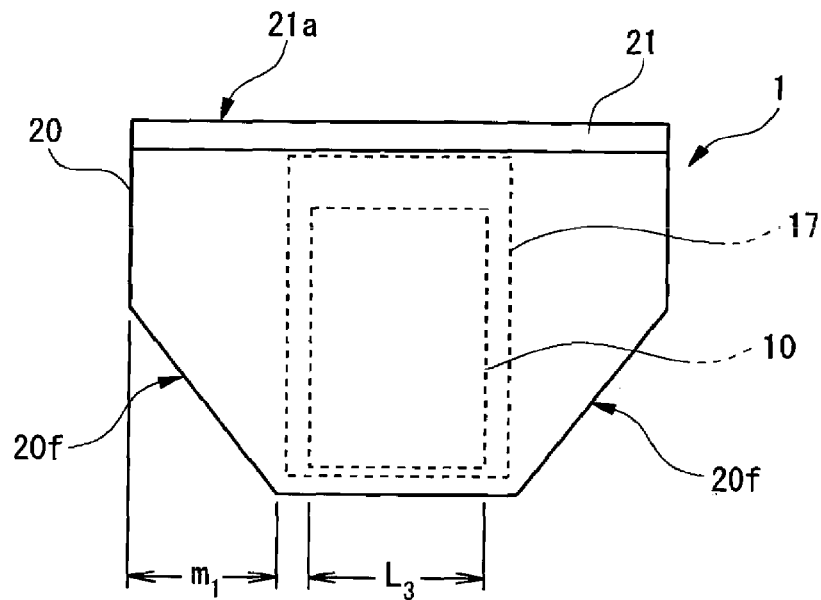
FIGS. 64A and 64B illustrate the difference in shapes between a conventional diaper and a diaper embodiment of the disposable garment of the present invention.
Figure 64B:
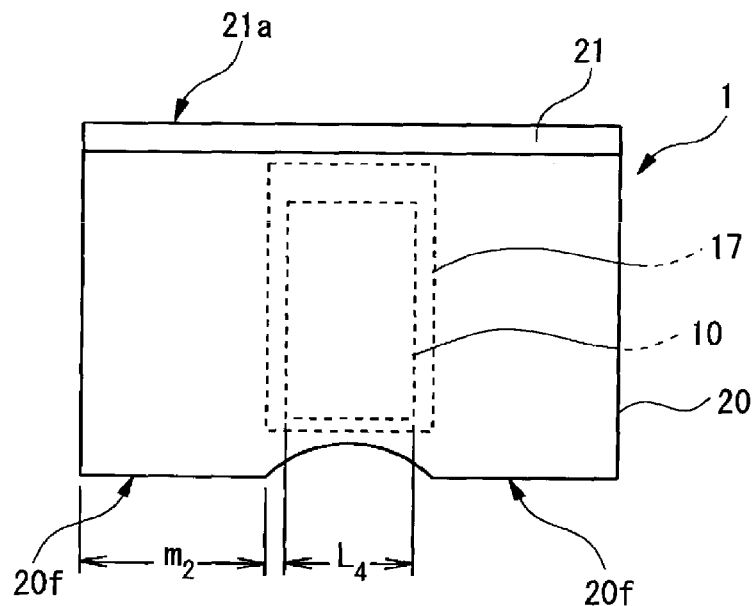

(17) Conventional diapers lack the force to push the absorbent member 10 against the body. Thus, as illustrated in FIG. 64A, the width L3 of the absorbent member 10 is needed to be sufficiently large in order to prevent urine leakage. As a result, as illustrated in FIG. 64A, to have large enough leg cuff openings 20f, the garment is restricted to being a brief-type. Alternatively, in a diaper configuration of the disposable garment of an embodiment of the present invention, the absorbent member 10 can be made to contact and press against the body, preventing urine leakage from the absorbent member 10. This allows the width L4 of the absorbent member 10 to be smaller and, as in the trunks-type garment illustrated in FIG. 64B, allows for the leg cuff opening 20f to have the same size as in brief-types. Because the width $m_2$ of the leg cuff openings 20f of the trunks-type is larger than the width $m_1$ of the leg cuff openings 20f of the brief-type, when the garment is worn by the wearer, when the leg cuff opening 20f is viewed from the side of the torso band opening 21a, the leg cuff openings 20f of the trunks-type illustrated in FIG. 64B appear larger than the leg cuff openings 20f of the brief-type illustrated in FIG. 64A. This makes inserting legs into the opening easier when the garment is worn by the wearer.

Second Embodiment

Figure 46:
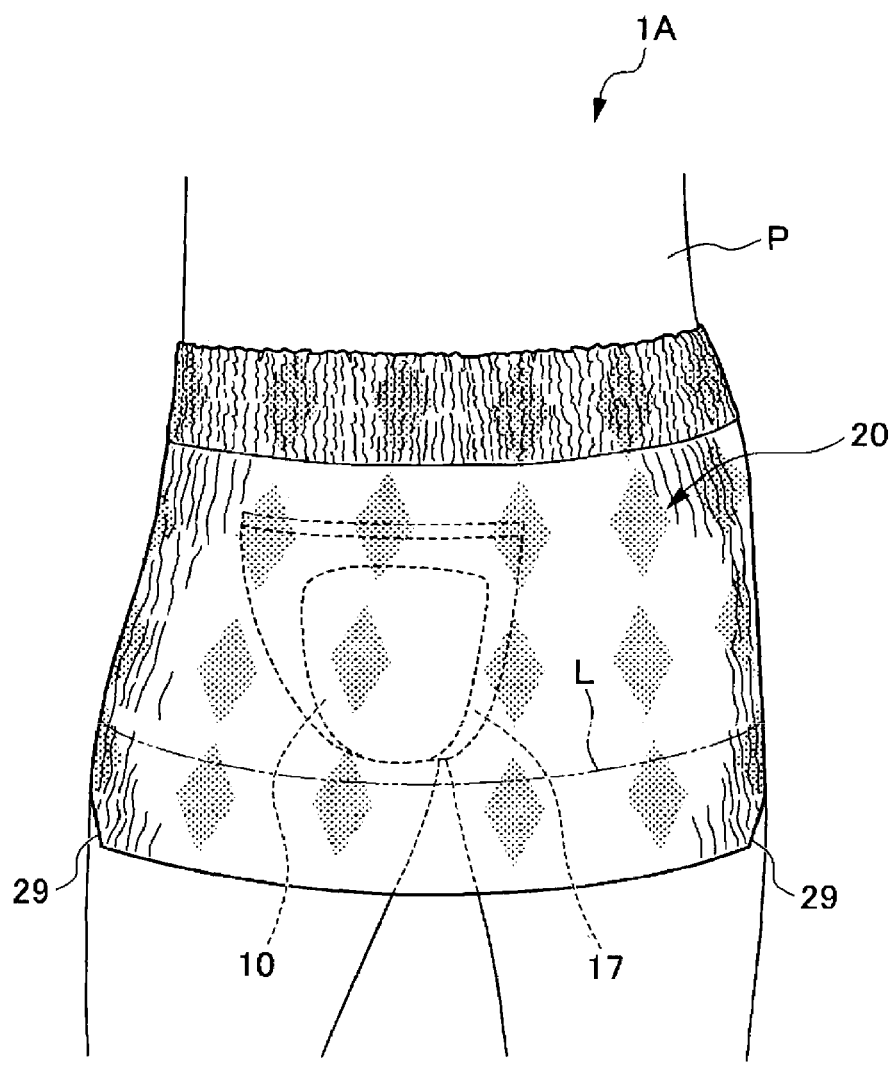
FIG. 46 is a diagram illustrating a disposable garment 1A according to a second embodiment.

FIG. 46 is a diagram illustrating a disposable garment 1A according to a second embodiment. The disposable garment 1A of the second embodiment also include the elastic sheet 17 disposed extending between the front portion 20a and the back portion 20b of the chassis 20.

Figure 47:
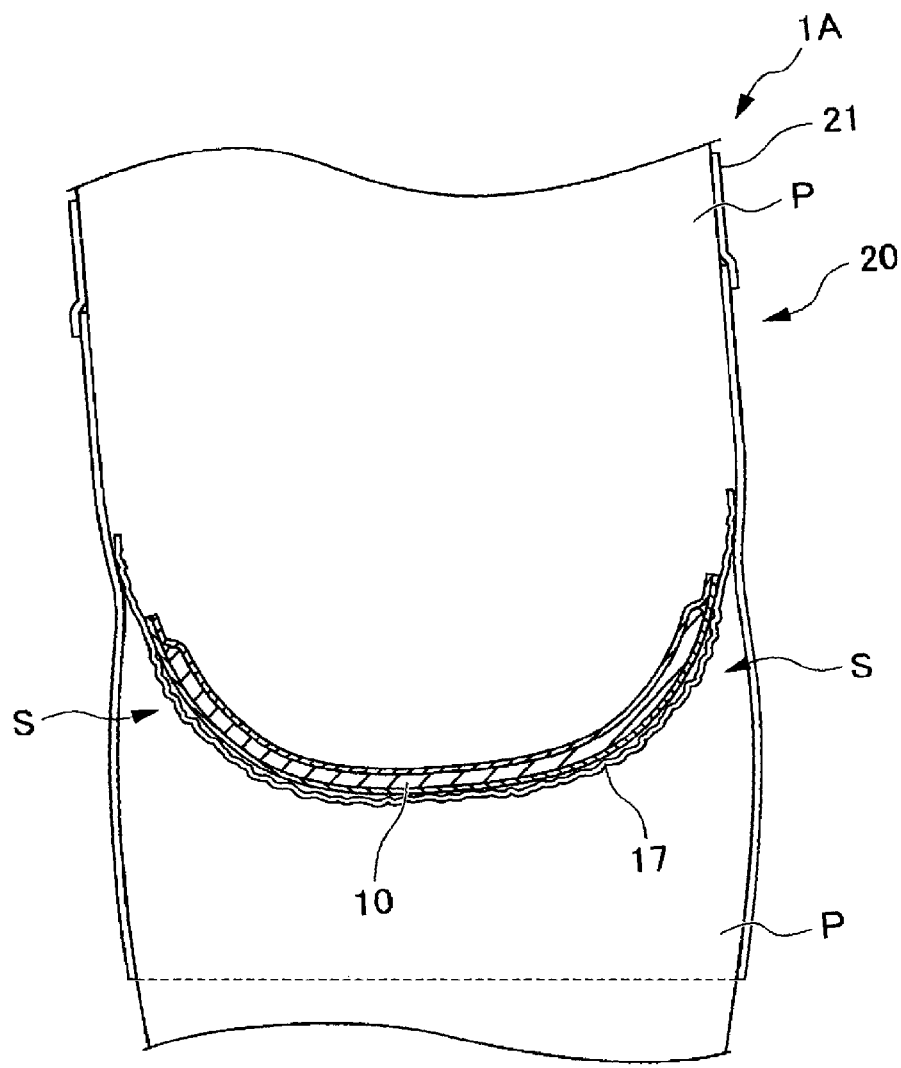
FIG. 47 is a cross-sectional view of the disposable garment 1A.

As illustrated in FIGS. 46 and 47, the disposable garment 1A of the present embodiment includes the chassis 20 and the elastic sheet 17 extending between the front portion and the back portion of the chassis 20. The absorbent member 10 is disposed on the inner side of the elastic sheet 17 (the upper side, the side proximal to the wearer, the side in contact with the skin).

As illustrated in FIG. 47, the chassis 20 includes the torso band 21 and the chassis 20. The torso band 21 is the portion that is worn around the waist of the wearer P and is disposed on the upper portion of the chassis 20. The chassis 20 is the portion that pushes the lower abdomen region of the wearer. The chassis 20 is formed in an annular shape. In other words, the chassis 20 of the present embodiment is different from the first embodiment in that it does not include an inside leg portion.

As illustrated in FIG. 46, the chassis 20 has a similar shape to that of a typical tube top and a similar length. The chassis 20 is not limited to the configuration of the present embodiment and may have a three-quarter length longer than that of the present embodiment or may have a shape that covers a portion of the wearer P above the waist. Additionally, as illustrated in by the imaginary line L in FIG. 46, the chassis 20 may have a length similar to that of a short skirt for women. In such configurations, by the shape having a longer cut on both sides than the disposable garment 1A illustrated in FIG. 46 (in other words have a V-shape as viewed from the front), leg movement can be facilitated.

Joining the Elastic Sheet to the Chassis (1) Joining the Elastic Sheet 17 to the Chassis 20

Figure 48A:
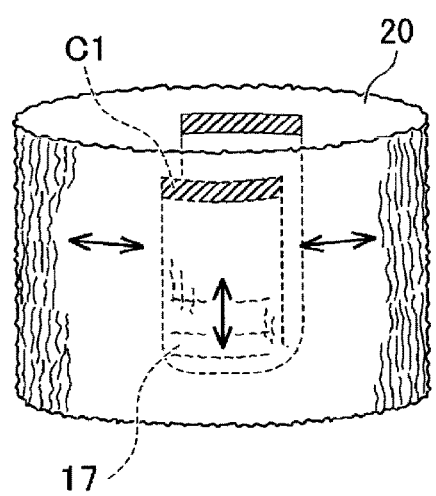
FIGS. 48A and 48B illustrate other variations of how the elastic sheet 17 is attached.
Figure 48B:
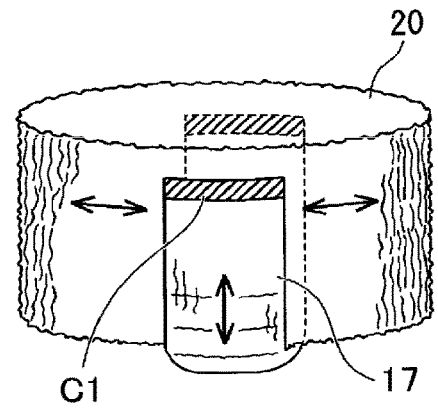

As illustrated in FIGS. 48A and 48B, the elastic sheet 17 of the present embodiment is joined at one end region in the longitudinal direction to the front portion of the chassis 20 in a central region. Additionally, the other end region in the longitudinal direction is joined to the back portion of the chassis 20 in a central region. One end region and other end region may not include the end portion and may be a region spaced apart from the end portion.

In the present embodiment, when the elastic sheet 17 is attached to the chassis 20, the chassis 20 may be in an unstretched state or a stretched state.

By fixing the one end region and other end region in the longitudinal direction of the elastic sheet 17 to the chassis 20 in such a manner, the elastic sheet 17 is supported in a curved state on the inner side of the chassis 20 as illustrated in FIGS. 24A and 24B and FIG. 25.

The curved lower end of the substantially central portion of the elastic sheet 17 is stretched down by the crotch of the wearer when the wearer P wears the disposable garment 1. In other words, when the garment is unworn, the curved lower end of the elastic sheet 17 is located above where it is located when the garment is worn by the wearer.

In the present embodiment, as illustrated in FIGS. 46 and 47, the absorbent member 10 is disposed on the elastic sheet 17. Accordingly, when the garment is worn by the wearer, the elastic sheet 17 stretches and this contractive force pushes the absorbent member 10 against the body side.

How the elastic sheet 17 is attached to the chassis 20 is not limited to the example of FIG. 47.

FIGS. 48A and 48B illustrate a variation of how the elastic sheet 17 is attached to the chassis.

The elastic sheet 17 illustrated in FIG. 48A includes one end in the longitudinal direction joined at the joined portion C1 located above the central portion on the inner side of the chassis (side proximal to the body). The other end in the longitudinal direction of the elastic sheet 17 is connected in a similar manner.

In such a configuration, when the wearer P wears the disposable garment 1A, the portion where the elastic sheet 17 and the chassis overlap is pressed against the wearer P by the chassis. As a result, the stability of the elastic sheet 17 is improved.

Additionally, one end in the longitudinal direction of the elastic sheet 17 may be joined at the joined portion located below the central portion on the inner side of the chassis 20 (the other end in the longitudinal direction of the elastic sheet 17 may be connected in a similar manner).

In such a configuration, the length of the elastic sheet 17 may be made even shorter than in the configurations illustrated in FIGS. 47 and 48A. Thus, the production cost can be reduced.

The elastic sheet 17 may be joined at different positions on the front portion and the back portion of the chassis 20. For example, the front end may be joined above the central portion and the back end may be joined below the central portion, or the front end and the back end may be joined at different positions.

A configuration in which the elastic sheet 17 is joined to the inner side of the chassis 20 is described while referencing to FIG. 48A. However, as illustrated in FIG. 48B, the elastic sheet 17 may be joined on the outer side of the chassis 20. The elastic sheet 17 illustrated in the FIG. 48B includes one end in the longitudinal direction joined at the joined portion C1 located above the central portion on the outer side of the chassis 20 (side opposite to the side proximal to the body). The other end in the longitudinal direction of the elastic sheet 17 is connected in a similar manner.

In the example of FIG. 48B, the elastic sheet 17 is located on the outer side of the chassis 20. Thus, the length of the chassis 20 is preferably shorter than that of the configuration illustrated in FIG. 48A.

The configuration illustrated in FIG. 48A and the configuration illustrated in FIG. 48B may be combined as suitable. For example, the front end can have the configuration illustrated in FIG. 48A, and the back end can have the configuration illustrated in FIG. 48B. In such a manner, by combining how the elastic sheet 17 is joined to the chassis 20 as suitable, characteristics specific to the features of the body of the wearer can be provided.

Figure 49A:
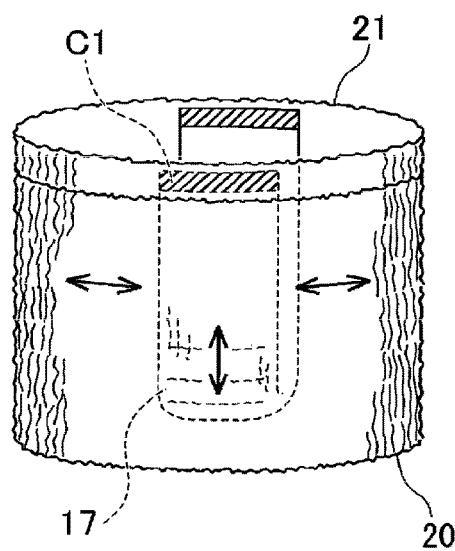
FIGS. 49A and 49B illustrate other variations of how the elastic sheet 17 is attached.
Figure 49B:
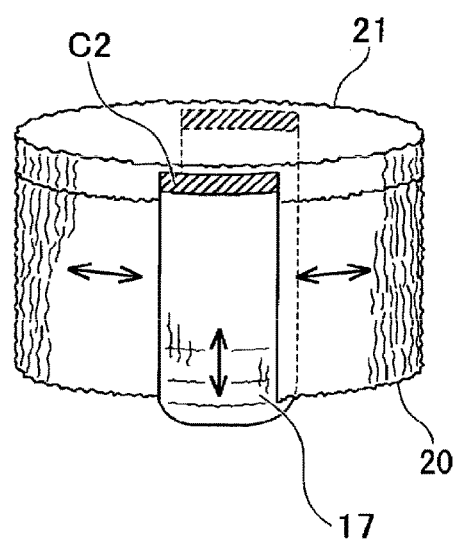

FIGS. 48A and 48B illustrate examples in which the elastic sheet 17 is attached to the chassis 20, but these examples are not limited thereto. The elastic sheet 17 may be attached to the torso band 21. FIGS. 49A and 49B illustrate a variation of how the elastic sheet 17 is attached to the torso band 21.

The elastic sheet 17 illustrated in FIG. 49A includes one end in the longitudinal direction joined at the joined portion C1 on the inner side of the torso band 21 (side proximal to the body). The other end in the longitudinal direction of the elastic sheet 17 is connected in a similar manner.

In such a configuration, when the wearer P wears the disposable garment 1A, the portion where the elastic sheet 17 is overlapped with the torso band 21 and the chassis 20 is pressed against the wearer P. As a result, the stability of the elastic sheet 17 is improved.

The elastic sheet 17 illustrated in FIG. 49B includes one end in the longitudinal direction joined at the joined portion C2 on the outer side of the torso band 21 (side opposite to the side proximal to the body). The other end in the longitudinal direction of the elastic sheet 17 is connected in a similar manner. In such a configuration, the elastic sheet 17 and the torso band 21 can be joined being disposed in a manner opposite to that illustrated in FIG. 22A.

The configuration illustrated in FIGS. 48A and 48B and the configuration illustrated in FIGS. 49A and 49B can be combined as suitable. For example, the front end can have the configuration illustrated in FIG. 48A, and the back end can have the configuration illustrated in FIG. 49A. In such a manner, by combining how the elastic sheet 17 is joined to the torso band 21 and the chassis 20 as suitable, characteristics specific to the features of the body of the wearer can be provided.

Figure 63:
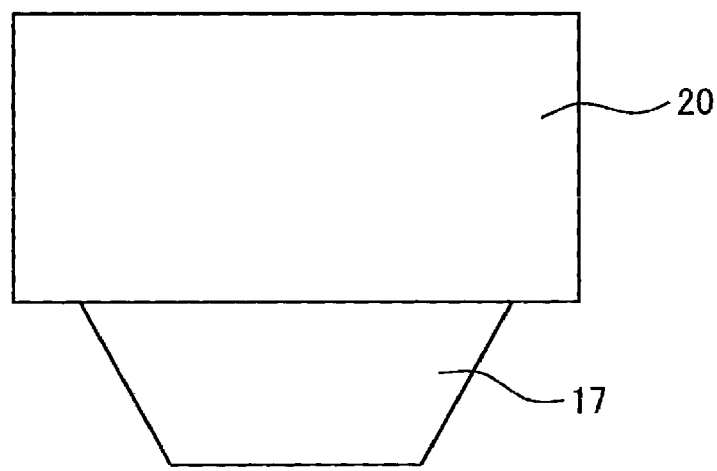
FIG. 63 illustrates another variation of the elastic sheet in an attached state.

As illustrated in FIG. 63, the elastic sheet 17 can be formed with the side proximal to the chassis 20 having a larger width than the inside leg side. By the side of the elastic sheet 17 proximal to the chassis 20 having a larger width, the elastic sheet 17 is reliably pushed against the body and the ability to prevent urine leakage is further improved.

Effect

Figure 50:
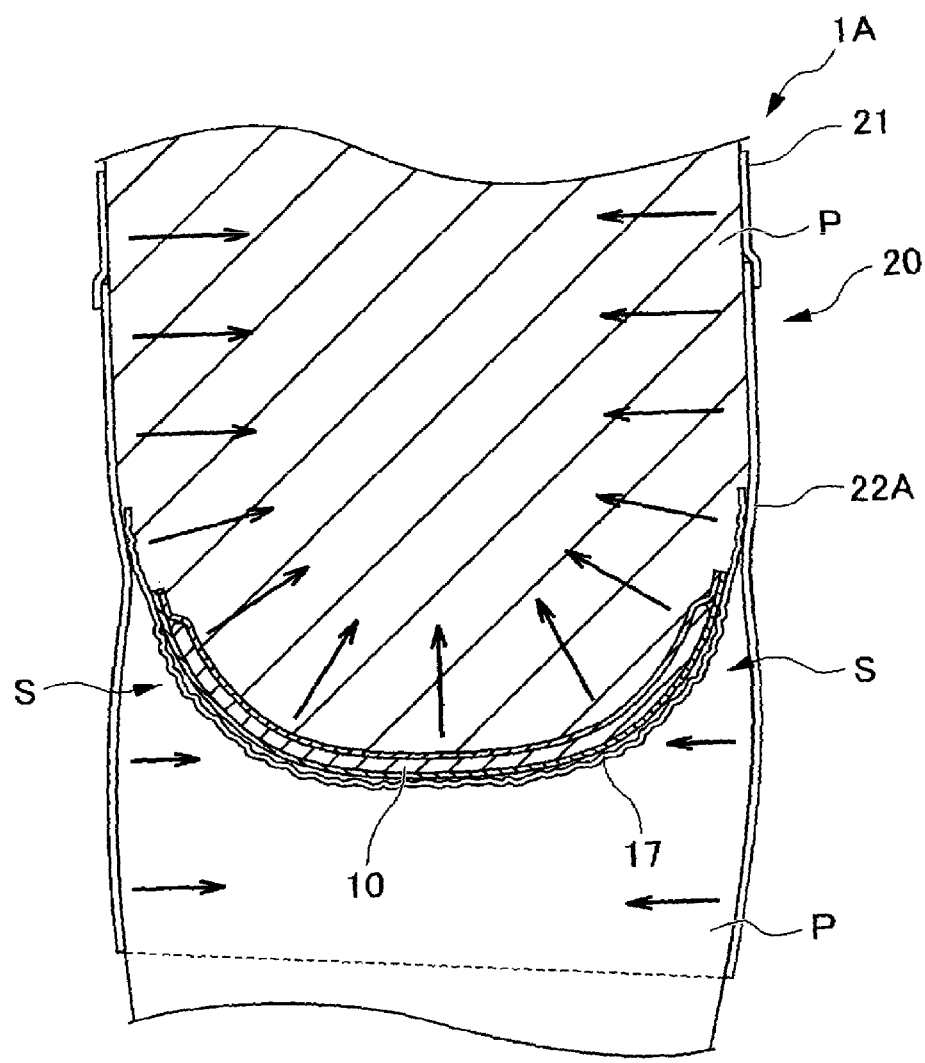
FIG. 50 is a diagram for explaining the function and effect of the disposable garment 1A according to the second embodiment.

FIG. 50 is a diagram for explaining the function of the disposable garment 1A according to the second embodiment. As illustrated, the disposable garment 1A worn by the wearer P includes the absorbent member 10 disposed on the elastic sheet 17. Accordingly, because the elastic sheet 17 can stretch, the force exerted when the elastic sheet 17 contracts presses the absorbent member 10 in the direction against the body. The pressing force in the direction against the body brings the absorbent member 10 into contact with the body. Additionally, because the chassis 20 stretches when the wearer P wears the disposable garment 1A, the force exerted when the chassis 20 contracts presses the chassis 20 in the direction against the body. The pressing force in the direction against the body brings the chassis 20 into contact with the body.

The elastic sheet 17 is not in contact with the chassis 20 at portions lower than the portion where the elastic sheet 17 is joined to the chassis 20 and the gap portion S is formed. Accordingly, the pressing force of the chassis 20 in the direction toward the body is greater than that of configurations in which the elastic sheet 17 and the chassis 20 are integrally joined. As a result, the chassis 20 can more strongly push the elastic sheet 17 in the direction toward the body.

In such a manner, as with the disposable garment 1A of the present embodiment, the synergy between the contracting force of the elastic sheet 17 and the contracting force of the chassis 20 enables the chassis 20 overall and including the elastic sheet 17 to contact the body with a greater pressing force.

In other respects, the disposable garment 1 of the second embodiment has the same effects as the disposable garment 1 of the first embodiment as described above.

Figure 51A:
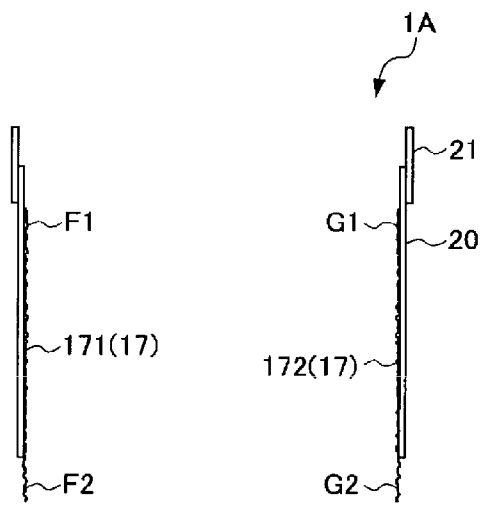
FIGS. 51A to 51C are diagrams for explaining variations of how the absorbent member 10 is attached in the disposable garment 1A of the second embodiment.
Figure 51B:
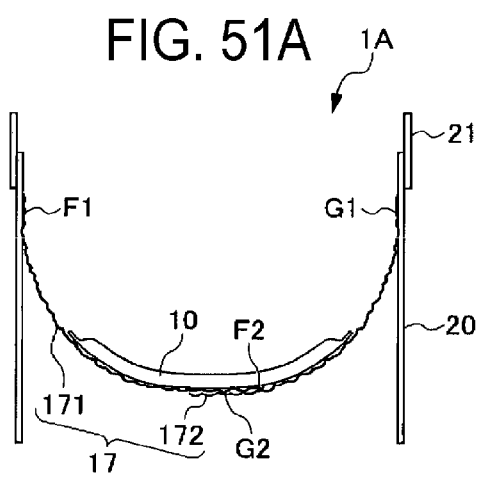
Figure 51C:
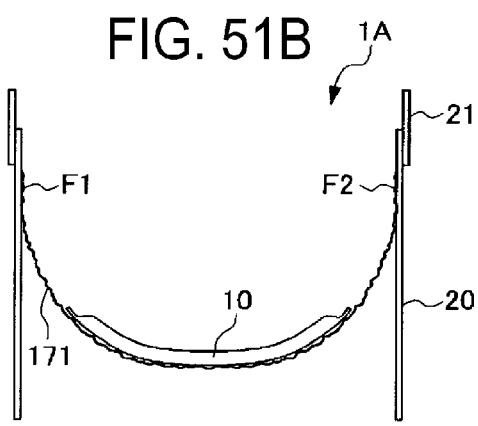

FIGS. 51A to 51C are diagrams for explaining variations of how the absorbent member 10 is attached in the disposable garment 1A of the second embodiment. FIG. 51A illustrates the absorbent member 10 in an unattached state. FIG. 51B illustrates the absorbent member 10 in an attached state. FIG. 51C illustrates a modified embodiment.

As illustrated in FIG. 51A, in the present embodiment, the elastic sheet 17 includes two portions: a first sheet member 171 and a second sheet member 172.

One end F1 of the first sheet member 171 is joined to the front portion of the chassis 20 and the other end is a free end F2 not attached to the absorbent member 10.

One end G1 of the second sheet member 172 is joined to the back portion of the chassis 20 and the other end is a free end G2 not attached to the absorbent member 10 in a similar manner to the first sheet member 171.

The first sheet member 171 and/or the second sheet member 172 is a sheet member similar to the elastic sheet 17 described above that can expand and contract in the length direction. The length direction is the direction extending from the front portion to the back portion of the chassis 20 passing through the inside leg of the wearer.

The expandable/contractible sheet member, for example, may be a sheet member made of a nonwoven fabric, a moisture permeable film, or a sheet member such as paper with strings of an elastic member 17a joined thereto, or may be a material with intrinsic elasticity such as a rubber, a urethane, a silicone sheet, a stocking or knit.

Furthermore, the expandable/contractible sheet member is not limited to having elasticity throughout the whole sheet member and may have elasticity in a portion of the sheet member.

Additionally, the elasticity configuration may be similar to that of the elastic sheet 17 of the first embodiment and have a configuration illustrated in FIGS. 15A to 15J and FIG. 16A to 16H.

Examples of the method of joining the first sheet member 171 and the second sheet member 172 to the chassis 20 include joining via sewing, a hot-melt adhesive, thermal sealing, or ultrasonic bonding, using an adhesive material, or any known method. Additionally, any of these methods may be used in combination.

Furthermore, the method of attaching the first sheet member 171 and the second sheet member 172 to the chassis 20 is not limited to a specific method and the variations of the first embodiment illustrated in FIGS. 23A to 23F can be used. Additionally, the first sheet member 171 and the second sheet member 172 may not be fixed to the chassis 20 or may be detachably attached.

As illustrated in FIG. 51B, the free end F2 of the first sheet member 171 and the free end G2 of the second sheet member 172 are detachably attached together by overlapping and joining the two ends and the absorbent member 10 can be disposed on the side proximal to the body. In this state, the absorbent member 10 can be pushed against the body side by the elastic force.

The present embodiment has the follow effects in addition to the effects of the second embodiment.

By adjusting how much the free ends F2, G2 of the first sheet member 171 and the second sheet member 172 overlap, the length of the elastic sheet 17 can be adjusted. Thus, the length of the elastic sheet 17 can be adjusted to match various body shapes including thinner wearers and larger wearers.

In the modified embodiment illustrated in FIG. 51C, the one end F1 of the first sheet member 171 is joined to the front portion (or the back portion) of the chassis 20 and the other end is the free end F2 when the absorbent member 10 is not attached.

The present embodiment has the follow effects in addition to the effects of the second embodiment.

By adjusting how much the free end F2 of the elastic sheet 17 and the chassis 20 overlap, the length of the elastic sheet 17 can be adjusted. Thus, the length of the elastic sheet 17 can be adjusted to match various body shapes including thinner wearers and larger wearers.

Third and Fourth Embodiment

Figure 52A:
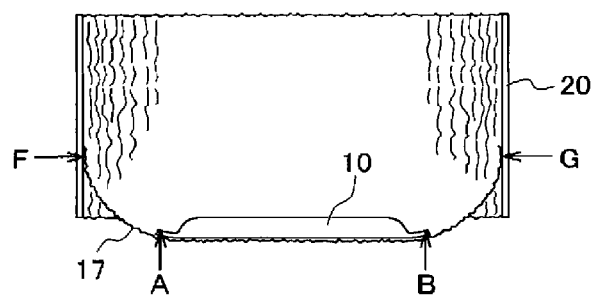
FIGS. 52A to 52C are diagrams for explaining a third and fourth embodiment.
Figure 52B:
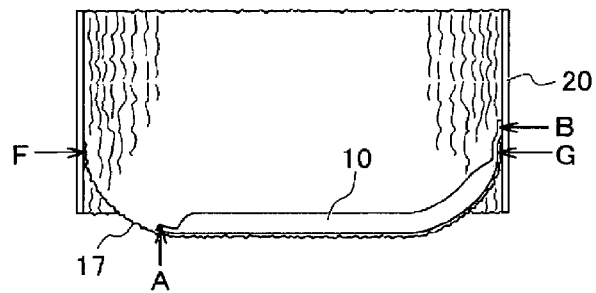
Figure 52C:
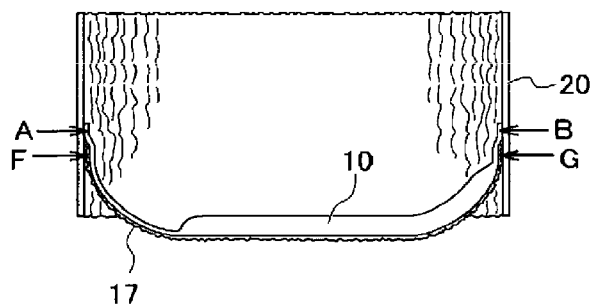

FIGS. 52A to 52C are diagrams for explaining a third and fourth embodiment. FIG. 52A illustrates the second embodiment (see FIG. 46) for comparison. FIG. 52B illustrated the third embodiment. FIG. 52C illustrated the fourth embodiment. In FIGS. 52A to 52C, only the chassis 20 is illustrated and configurations with a short length are illustrated.

In the second embodiment illustrated in FIG. 52A, the absorbent member 10 is attached to the central portion of the surface on the side of the elastic sheet 17 proximal to the skin.

In such configurations, as described above, the absorbent member 10 may not be attached to the elastic sheet 17 across the entire surface. For example, as illustrated, the absorbent member 10 may only be attached at 2 positions: end A and end B, or at end A or B. Furthermore, the absorbent member 10 may be attached not at an end portion, and may be attached at a portion spaced at predetermined distance away from the end portions such as end A and B. Additionally, the shape of the attached portion is not limited to a dot shape and may be a line shape in the transverse direction of the absorbent member 10 or another shape. The positions where the elastic sheet 17 is attached to the chassis 20 are denoted in the drawings by reference signs F and G.

In the third embodiment illustrated in FIG. 52B, one end (end B) of the absorbent member 10 extends to the chassis 20 and is directly joined to the chassis 20.

Examples of the method of joining the end portion of the absorbent member 10 to the chassis 20 include joining via sewing, a hot-melt adhesive, thermal sealing, or ultrasonic bonding, using an adhesive material, or any known method. Additionally, any of these methods may be used in combination. Additionally, the end portion may be fixed or detachably attached. Furthermore, the positions where the elastic sheet 17 is attached to the chassis 20 are denoted in the drawings by reference signs F and G.

In such configurations, the absorbent member 10 may not be attached to the elastic sheet 17 across the entire surface. The end B of the absorbent member 10 is joined to the chassis 20. Thus, other sections of the absorbent member 10 need not be attached to the elastic sheet 17 and the illustrated end A of the absorbent member 10 may be attached to the elastic sheet 17. Additionally, in configurations in which the absorbent member 10 and the chassis 20 are attached, the portion of the absorbent member 10 attached may be another portion other than the end A. Additionally, the shape of the attached portion is not limited to a dot shape and may be a line shape in the transverse direction of the absorbent member 10 or another shape.

In the fourth embodiment illustrated in FIG. 52C, both ends of the absorbent member 10 extend to the chassis 20 and are directly joined to the chassis 20.

In such a configuration, the absorbent member 10 and the elastic sheet 17 are not joined together.

Fifth, Sixth, and Seventh Embodiment

Figure 53A:
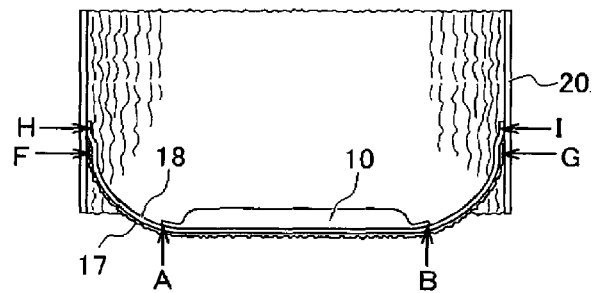
FIGS. 53A to 53C are diagrams for explaining a fifth, sixth, and seventh embodiment.
Figure 53B:
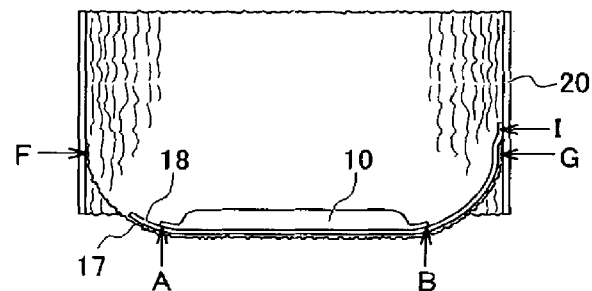
Figure 53C:
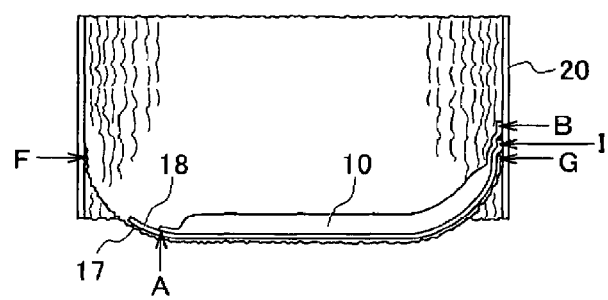

FIGS. 53A to 53C are diagrams for explaining a fifth, sixth, and seventh embodiment. FIG. 53A illustrates the fifth embodiment of the present invention. FIG. 53B illustrates the sixth embodiment of the present invention. FIG. 53C illustrates the seventh embodiment of the present invention. In FIGS. 53A to 53C, only the chassis 20 is illustrated and configurations with a short length are illustrated.

The fifth, sixth, and seventh embodiment are different from the first embodiment in that an inner sheet 18 is disposed above (on the side proximal to the body of) the elastic sheet 17. The inner sheet 18 is a sheet member made of a paper, a nonwoven fabric, or a film. As the inner sheet 18, a non-stretchable sheet or a sheet with less stretchability than the elastic sheet 17 is preferably used, however, the inner sheet 18 is not limited thereto and the inner sheet 18 may have similar or higher stretchability than the elastic sheet 17.

In the fifth embodiment illustrated in FIG. 53A, both ends of the inner sheet 18 are joined to the chassis 20.

Examples of the method of joining include joining via sewing, a hot-melt adhesive, thermal sealing, or ultrasonic bonding, using an adhesive material, or any known method. Additionally, any of these methods may be used in combination. Additionally, the both ends may be fixed or detachably attached.

In the sixth embodiment illustrated in FIG. 53B, only one end of the inner sheet 18 is joined to the chassis 20. In the seventh embodiment illustrated in FIG. 53C, in a similar manner to the configuration of FIG. 53B, only one end of the inner sheet 18 is joined to the chassis 20, and additionally, one end of the absorbent member 10 is also joined to the chassis 20.

In the fifth, sixth, and seventh embodiment, the absorbent member 10 is attached to the inner sheet 18.

According to the embodiments described above, in configurations in which the inner sheet 18 is non-stretchable or has less stretchability than the elastic sheet 17, the lines do not be formed as much as in the elastic sheet 17. As a result, in configurations in which the wearer attaches the absorbent member 10 to the inner sheet 18, or attaching the absorbent member 10 to the inner sheet 18 is a production step, the absorbent member 10 can be attached to the elastic sheet 17, making attachment simple.

In configurations in which the elasticity of the inner sheet 18 is stronger than that of the configurations described above, in attaching the absorbent member 10 to the elastic sheet 17, the inner sheet 18 is required to be spread out.

Furthermore, because the absorbent member 10 is not directly attached to the elastic sheet 17, the absorbent member 10 does not impact on the elastic force of the elastic sheet 17. As a result, when the garment is worn by the wearer, the elastic force of the elastic sheet 17 presses the inner sheet 18 and in turn the absorbent member 10 in the direction of the body of the wearer from directly below. This enhances the contact with the wearer of the absorbent member 10 and prevents urine leakage. Additionally, perforated lines (not illustrated) may be provided on the inner sheet 18 as necessary. By perforated lines being provided on the elastic sheet 17 and the inner sheet 18, if the wearer wishes to lessen the pressing force when the garment is worn by the wearer, the wearer can sever the elastic sheet 17 or the inner sheet 18 along the perforated lines to adjust the pressing force against his/her body.

In configurations in which the inner sheet 18 is an expandable/contractible sheet, the expansion and contraction of the elastic sheet 17 together with the pressing force against the body can be increased.

In the fifth, sixth, and seventh embodiment, in a similar manner to the elastic sheet 17 illustrated in FIGS. 51A to 51C, the inner sheet 18 may include two portions: a first inner sheet and a second inner sheet.

In a similar manner to the example of FIGS. 51A to 51C, in such a configuration, the first inner sheet and/or the second inner sheet may be a sheet member that can expand and contract in the length in a similar manner to the elastic sheet 17 described above. The length direction is the direction extending from the front portion to the back portion of the chassis 20 passing through the inside leg of the wearer.

The expandable/contractible sheet member, for example, may be a sheet member made of a nonwoven fabric, a moisture permeable film, or a sheet member such as a paper with strings of an elastic member 17a joined thereto, or may be a material with intrinsic elasticity such as a rubber, a urethane elastic member, a silicone elastic member, a silicone sheet, a stocking or knit.

Furthermore, the expandable/contractible sheet member is not limited to having elasticity throughout the whole sheet member and may have elasticity in a portion of the sheet member.

Additionally, the elasticity configuration may be similar to that of the elastic sheet 17 of the first embodiment and have a configuration illustrated in FIGS. 11A to 11I and FIGS. 12A and 12B.

Additionally, as illustrated in FIGS. 53A and 53B, in the fifth and sixth embodiment, where the absorbent member 10 is joined to the inner sheet 18 is the end A and the end B of the absorbent member 10.

As illustrated in FIG. 53C, in the seventh embodiment, where the absorbent member 10 is joined to the inner sheet 18 is the end A of the absorbent member 10. Additionally, where the absorbent member 10 is joined to the chassis 20 is the end B.

The absorbent member 10 is preferably not attached to the inner sheet 18 across the entire surface. In configurations such as those of FIGS. 53A and 53B, the absorbent member 10 may only be attached at 2 positions: end A and end B, or at end A or B. Furthermore, the absorbent member 10 may be attached not at an end portion, and may be attached at a portion spaced at predetermined distance away from the end portions.

In the configuration of FIG. 53C, the end B of the absorbent member 10 is joined to the chassis 20. Thus, other sections of the absorbent member 10 need not be attached to the inner sheet 18 and the illustrated end A of the absorbent member 10 may be attached to the inner sheet 18. Additionally, in configurations in which the absorbent member 10 and the chassis 20 are attached, the portion of the absorbent member 10 attached may be another portion other than the end A. Additionally, the shape of the attached portion is not limited to a dot shape and may be a line shape in the transverse direction of the absorbent member 10 or another shape.

Where the inner sheet 18 is joined to the chassis 20 is denoted by H and I in FIG. 53A and by I in FIGS. 53B and 53C. Where the elastic sheet 17 is joined to the chassis 20 is denoted by F and G in FIGS. 53A to 53C.

Eighth Embodiment

Figure 54A:
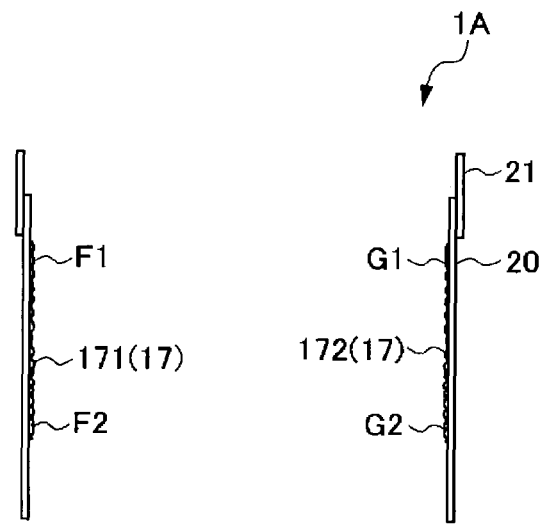
FIGS. 54A to 54C are diagrams for explaining an eighth embodiment.
Figure 54B:
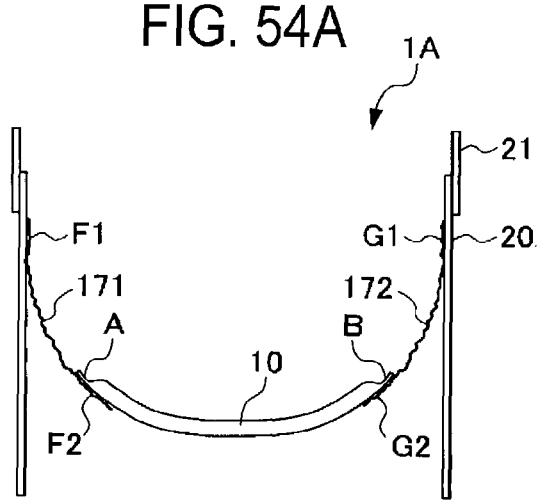

FIGS. 54A and 54B are diagrams for explaining the eighth embodiment of the present invention. FIG. 54A illustrates the absorbent member 10 in an unattached state. FIG. 54B illustrates the absorbent member 10 is an attached state.

As illustrated, in the eighth embodiment in a similar manner to the example illustrated in FIGS. 51A to 51C, the elastic sheet 17 includes two portions: the first sheet member 171 and the second sheet member 172. However, the first sheet member 171 and the second sheet member 172 of the present embodiment are shorter than the first sheet member 171 and the second sheet member 172 of the configuration of FIGS. 51A to 51C.

One end F1 of the first sheet member 171 is joined to the front portion of the chassis 20 and the other end is a free end F2 not attached to the absorbent member 10.

One end G1 of the second sheet member 172 is joined to the back portion of the chassis 20 and the other end is a free end G2 not attached to the absorbent member 10 in a similar manner to the first sheet member 171.

The first sheet member 171 and/or the second sheet member 172 is a sheet member similar to the elastic sheet 17 described above that can expand and contract in the length direction. The length direction is the direction extending from the front portion to the back portion of the chassis 20 passing through the inside leg of the wearer.

The expandable/contractible sheet member, for example, may be a sheet member made of a nonwoven fabric, a moisture permeable film, or a sheet member such as a paper with strings of an elastic member 17a joined thereto, or may be a material with intrinsic elasticity such as a rubber, a urethane elastic member, a silicone elastic member, a silicone sheet, a stocking or knit.

Furthermore, the expandable/contractible sheet member is not limited to having elasticity throughout the whole sheet member and may have elasticity in a portion of the sheet member.

Additionally, the elasticity configuration may be similar to that of the elastic sheet 17 of the first embodiment and have a configuration illustrated in FIGS. 15A to 15J and FIG. 16A to 16H.

Examples of the method of joining the first sheet member 171 and the second sheet member 172 to the chassis 20 include joining via sewing, a hot-melt adhesive, thermal sealing, or ultrasonic bonding, using an adhesive material, or any known method. Additionally, any of these methods may be used in combination.

Furthermore, the method of attaching the first sheet member 171 and the second sheet member 172 to the chassis 20 is not limited to a specific method and the variations of the first embodiment illustrated in FIGS. 23A to 23F and FIGS. 24A and 24B can be used.

As illustrated in FIG. 54B, the free ends F2, G2 of the first sheet member 171 and the second sheet member 172 are detachably attached to the end portions A, B of the absorbent member 10. Additionally, the absorbent member 10 is supported by the first sheet member 171 and the second sheet member 172, and the elastic force of the first sheet member 171 and/or the second sheet member 172 can press the absorbent member 10 against the body side.

Ninth Embodiment

Figure 54C:
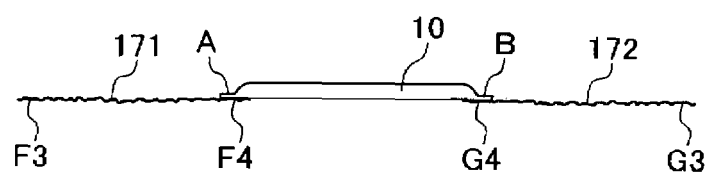

FIG. 54C is a diagram for explaining the ninth embodiment of the present invention.

As illustrated, the ninth embodiment is different from the eighth embodiment in that an end F4 of the first sheet member 171 is joined to the end A of the absorbent member 10. Additionally, an end G4 of the second sheet member 172 is joined to the end B of the absorbent member 10. Though not illustrated, the ends, F3, G3 of the first sheet member 171 and the second sheet member 172 are detachably attached to the front end and the back end of the chassis 20.

In other words, the difference between the eighth embodiment and the ninth embodiment is that in the eighth embodiment, the free ends F2, G2 of the first sheet member 171 and the second sheet member 172 are detachably attached to the end portions A, B of the absorbent member 10, and in the ninth embodiment, the end portions F3, G3 of the first sheet member 171 and the second sheet member 172 are joined or detachably attached to the chassis 20.

The eighth embodiment and the ninth embodiment can be combined and either the first sheet member 171 or the second sheet member 172 can be fixed to the absorbent member 10 and the other fixed to the chassis 20.

The above-described embodiments illustrated in FIGS. 51A to 51C to 54A to 54C may be used in the method of attaching the absorbent member 10 of the first embodiment.

Tenth Embodiment

Figure 55A:
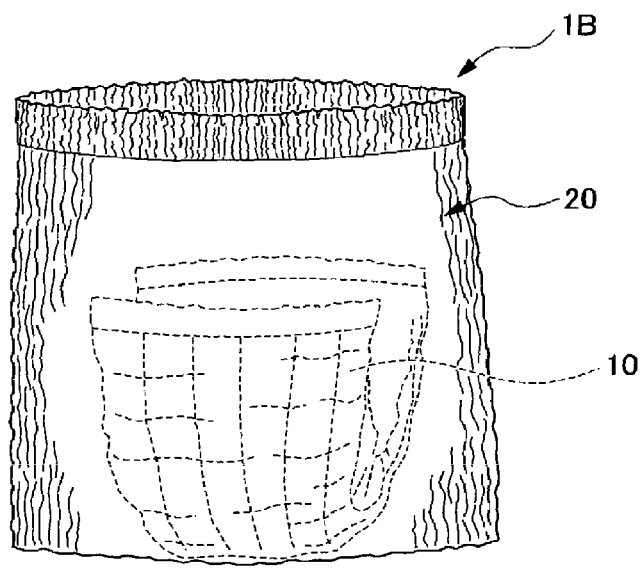
FIGS. 55A and 55B are diagrams for explaining a disposable garment according to a tenth embodiment.
Figure 55B:
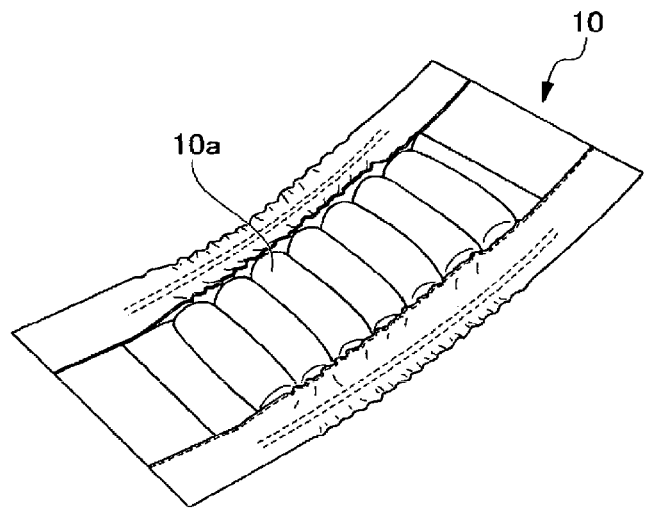

FIGS. 55A and 55B are diagrams for explaining a disposable garment according to the tenth embodiment of the present invention.

As illustrated, a disposable garment 1B of the tenth embodiment is different from the first embodiment and the second embodiment in that the elastic sheet 17 is not provided. Additionally, the absorbent member 10 is directly attached to a chassis 20A, and the absorbent member 10 can expand and contract in the length direction. FIG. 55B is a diagram illustrating the absorbent member 10 described below. In the present embodiment, the position where the absorbent member 10 is attached to the chassis 20 and the joining configuration are similar to that of the second embodiment but a variation of how the elastic sheet 17 is attached to the chassis 20 can be used (see FIGS. 49A and 49B and FIG. 50).

Figure 56A:
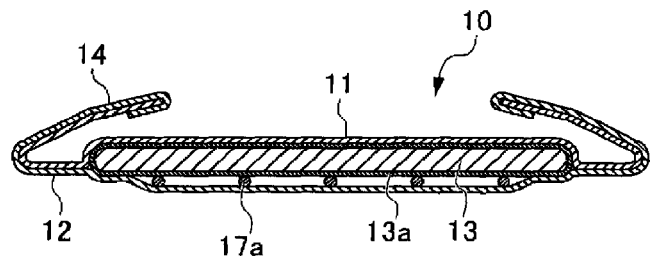
FIGS. 56A to 56D are cross-sectional views of the absorbent member 10 according to the tenth embodiment.
Figure 56B:
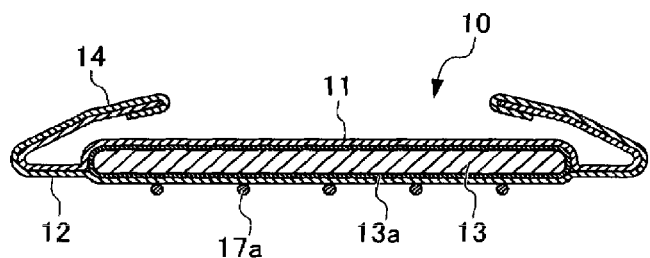
Figure 56C:
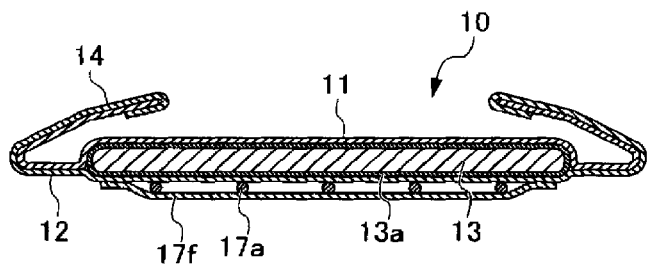
Figure 56D:
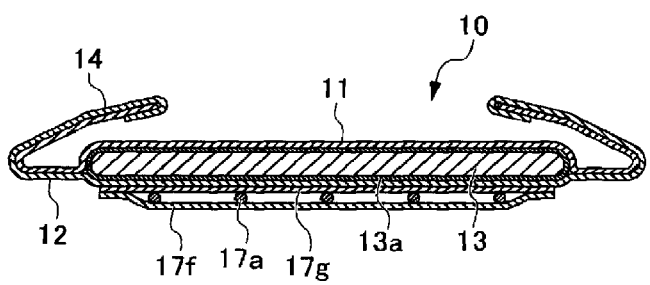

FIGS. 56A to 56D are cross-sectional views of absorbent members 10. FIG. 56A is a cross-sectional view of the absorbent member 10 of the present embodiment. FIGS. 56B, 56C, and 56D are modified embodiments. As illustrated, the absorbent member 10 of FIG. 56A includes the string-like elastic member 17a disposed between the back sheet 12 and the absorbent core 13 (on the side of the absorbent core 13 opposite the body). The elastic member 17a is joined to the back sheet 12 in a stretched state.

Examples of the method of joining include joining via sewing, a hot-melt adhesive, thermal sealing, or ultrasonic bonding, using an adhesive material, or any known method. Additionally, any of these methods may be used in combination. The structure of the absorbent member 10 is otherwise similar to that of the first embodiment.

Additionally, how the elastic member 17a (elastic member) is disposed in the absorbent member 10 is similar to that elastic sheet 17 of the first embodiment illustrated in FIGS.

15A to 15J and FIGS. 16A to 16F. Furthermore, the absorbent member 10 is not limited to having elasticity throughout the whole member and may have elasticity in a portion of the absorbent member 10. Additionally, the elasticity configuration may be similar to that of the elastic sheet 17 of the first embodiment and have a configuration illustrated in FIGS. 15A to 15J and FIGS. 16A and 16H.

The absorbent member 10 of the present embodiment can have the same shape as that of the elastic sheet 17 of FIG. 16G In other words, the absorbent member 10 of the present embodiment is a rectangle, but may have a wider shape at both ends as illustrated in FIG. 16G When the absorbent member 10 with such a shape is attached to the chassis 20A, a diaper such as that illustrated in FIG. 16H is formed. The absorbent member 10 may also have an hourglass shape or an oval shape.

FIG. 56B is a cross-sectional view of the absorbent member 10 of a first modified embodiment.

As illustrated, the absorbent member 10 includes the string-like elastic member 17a on the back side of the back sheet 12 (the side opposite the side proximal to the body). The elastic member 17a is joined to the back sheet 12 in a stretched state.

FIG. 56C is a cross-sectional view of the absorbent member 10 of a second modified embodiment.

As illustrated, the absorbent member 10 includes the string-like elastic member 17a on the back side of the back sheet 12 (the side opposite the side proximal to the body), and also a nonwoven fabric 17f on the back side.

FIG. 56D is a cross-sectional view of the absorbent member 10 of a third modified embodiment.

As illustrated, the absorbent member 10 includes a nonwoven fabric 17g on the back side of the back sheet 12 (the side opposite the side proximal to the body), the string-like elastic member 17a on the back side, and also the nonwoven fabric 17f on the back side.

According to the present embodiment, the contraction of the elastic member 17a contracts the absorbent member 10 as a whole, and as illustrated in FIG. 55B, concaves and convexes 10a are formed on the surface of the absorbent member 10 which is in contact with the body.

The convex portions of the concaves and convexes 10a formed on the absorbent member 10 come into contact with the body. This contact prevents urine leakage in a similar manner to the first embodiment.

Additionally, in the present embodiment, the concave portions formed on the absorbent member 10 ensure air permeability and prevent sweatiness.

Eleventh Embodiment

Figure 57:
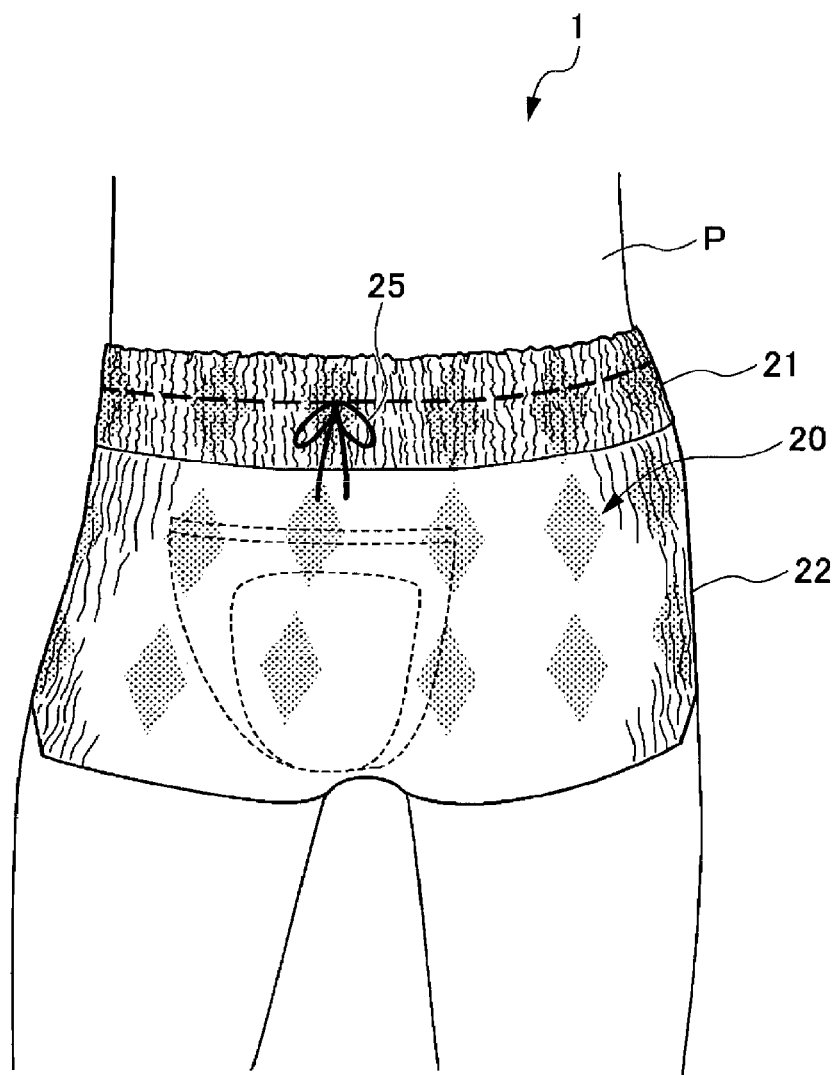
FIG. 57 is a diagram for explaining an eleventh embodiment.

The torso band 21 illustrated in FIG. 57 may include a string 25 (string-like member) inside the torso band 21. The string 25 is disposed all around the torso band 21. The string 25 has a portion pulled out from a front portion of the torso band 21 to the outside. The wearer can adjust the amount that the string 25 is pulled out and wear the torso band 21 with a desired tightness by tying the string 25 at the end. The string 25 may be a bundled strand of cotton or hemp fibers or may be a bundled strand of synthetic fibers. Additionally, vinyl string or rubber string may be used. Furthermore, the string 25 may be provided in the chassis 20.

Twelfth Embodiment

Figure 58A:
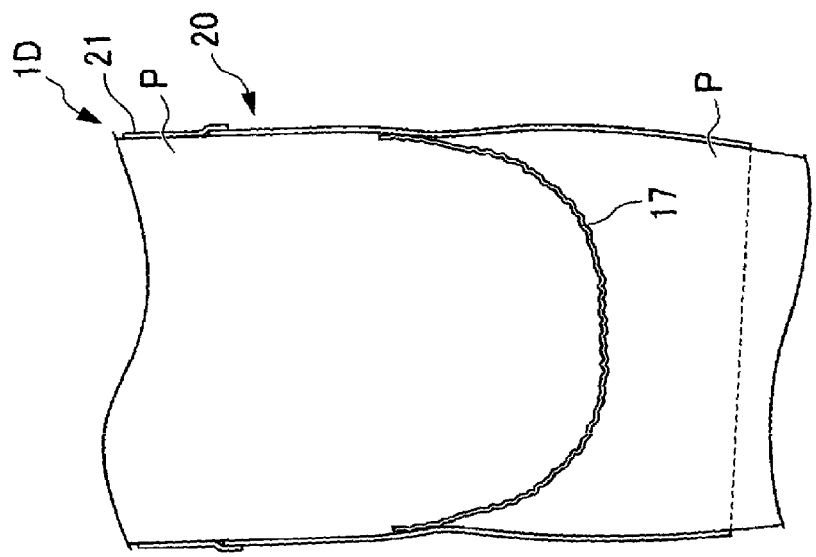
FIGS. 58A and 58B are diagrams for explaining a twelfth embodiment.
Figure 58B:
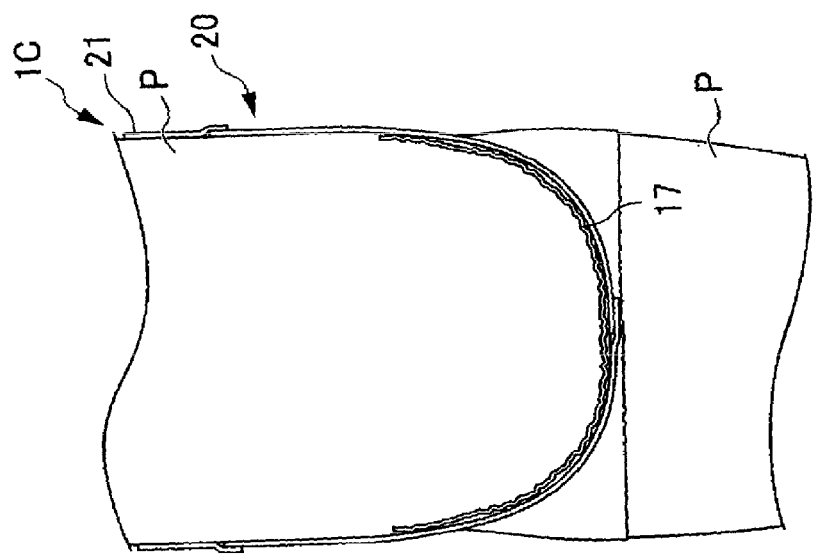

FIGS. 58A and 58B are diagrams for explaining the twelfth embodiment.

A disposable garment 1C illustrated in FIG. 58A is different from the disposable garment 1 of the first embodiment in that the absorbent member 10 is not provided on the inner side of the elastic sheet 17. Additionally, a disposable garment 1D illustrated in FIG. 58B is different from the disposable garment 1A of the second embodiment in that the absorbent member 10 is not provided on the inner side of the elastic sheet 17. In such embodiments in which the absorbent member 10 is not provided on the inner side of the elastic sheet 17, the elastic sheet 17 can also have enhanced contact with the body and thus achieve a superior comfortable feel, as explained in reference to FIGS. 15A to 15J and FIGS. 16A to 16H. In the present embodiment, a paper sheet 201 may be disposed on the inner side of the elastic sheet 17 (see FIG. 15A).

Thirteenth Embodiment

Figure 59A:
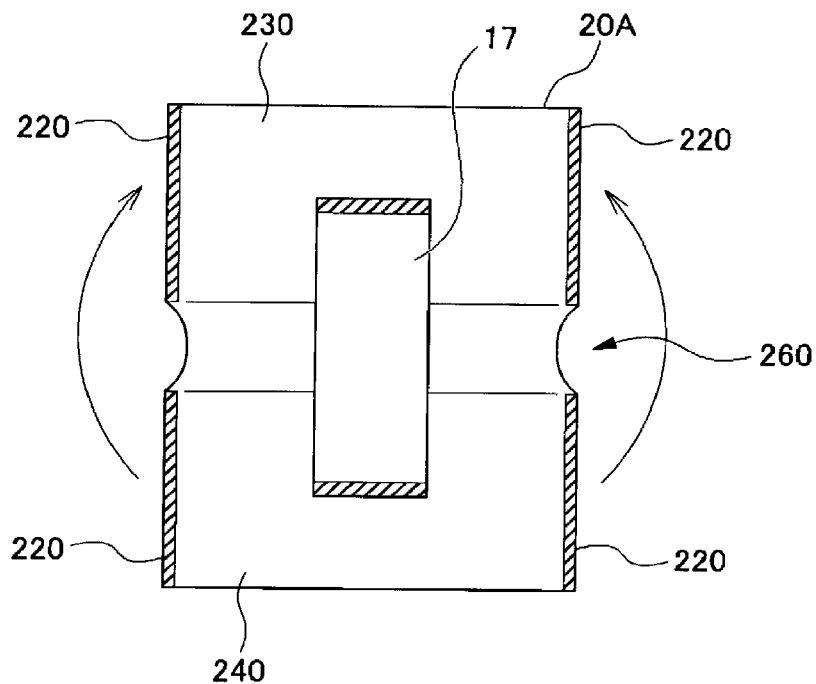
FIGS. 59A and 59B are diagrams for explaining a fourteenth embodiment.
Figure 59B:
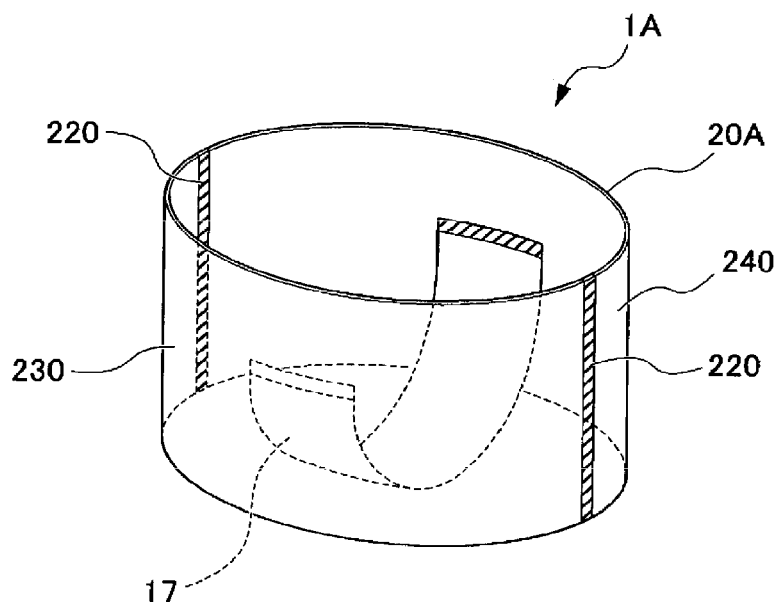

In the present embodiment, a production process of the disposable garment 1A of the second embodiment will be described. FIGS. 59A and 59B are diagrams for explaining the thirteenth embodiment.

In the disposable garment 1A of the present embodiment, the chassis 20A is formed like a tube top. As illustrated in FIG. 59A, the elastic sheet 17 is joined to the chassis 20A with a slack portion 260 formed in the central portion of the chassis 20A.

The chassis 20A is formed by bringing together side edge portions 220 that oppose each other in the length direction and joining the side edge portions 220 via thermal sealing. The slack portion 260 formed in the central portion of the chassis 20A is severed before or after the side edge portions 220 are joined together.

Thus, as illustrated in FIG. 59B, the disposable garment 1A including the annular chassis 20 and the elastic sheet 17 that extends between a front portion 230 and a back portion 240 is completed.

Though not illustrated in FIGS. 59A and 59B, by adjusting the shape of the side edge portions 220 of the chassis 20, a slit 29 can be formed on the sides of the chassis 20 (see FIG. 47).

Fourteenth Embodiment

Figure 60:
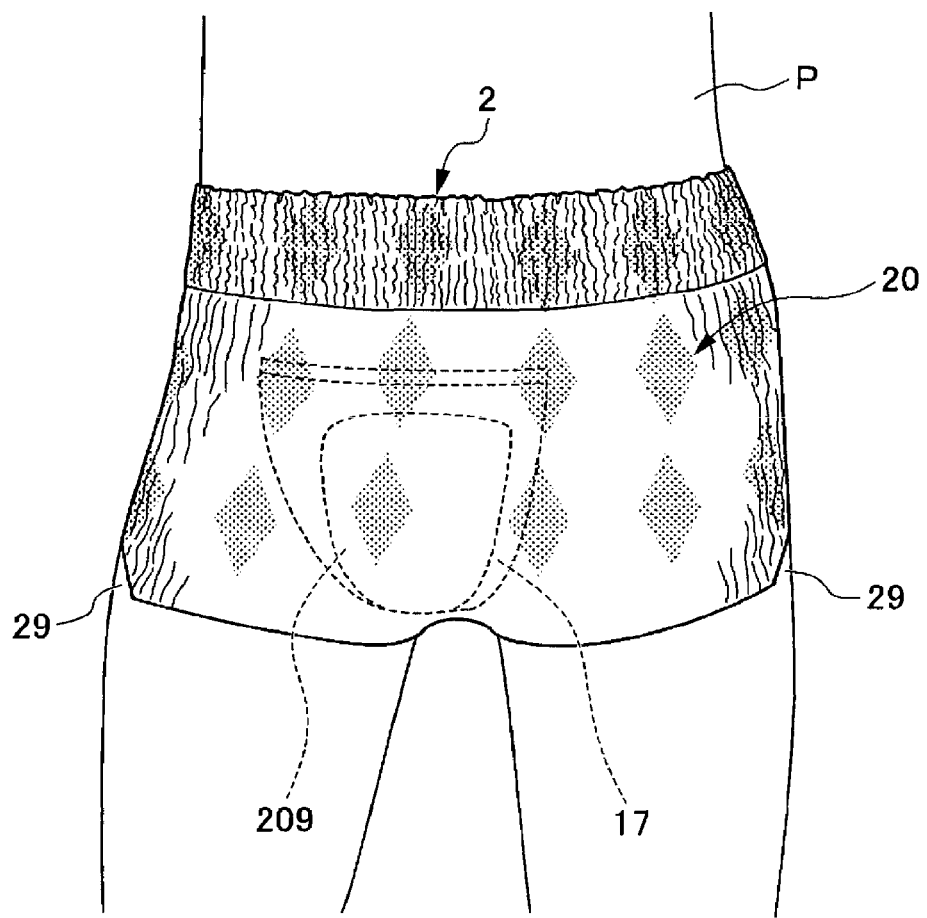
FIG. 60 is a diagram illustrating a disposable swimwear pants 2 worn by the wearer P.
Figure 61:
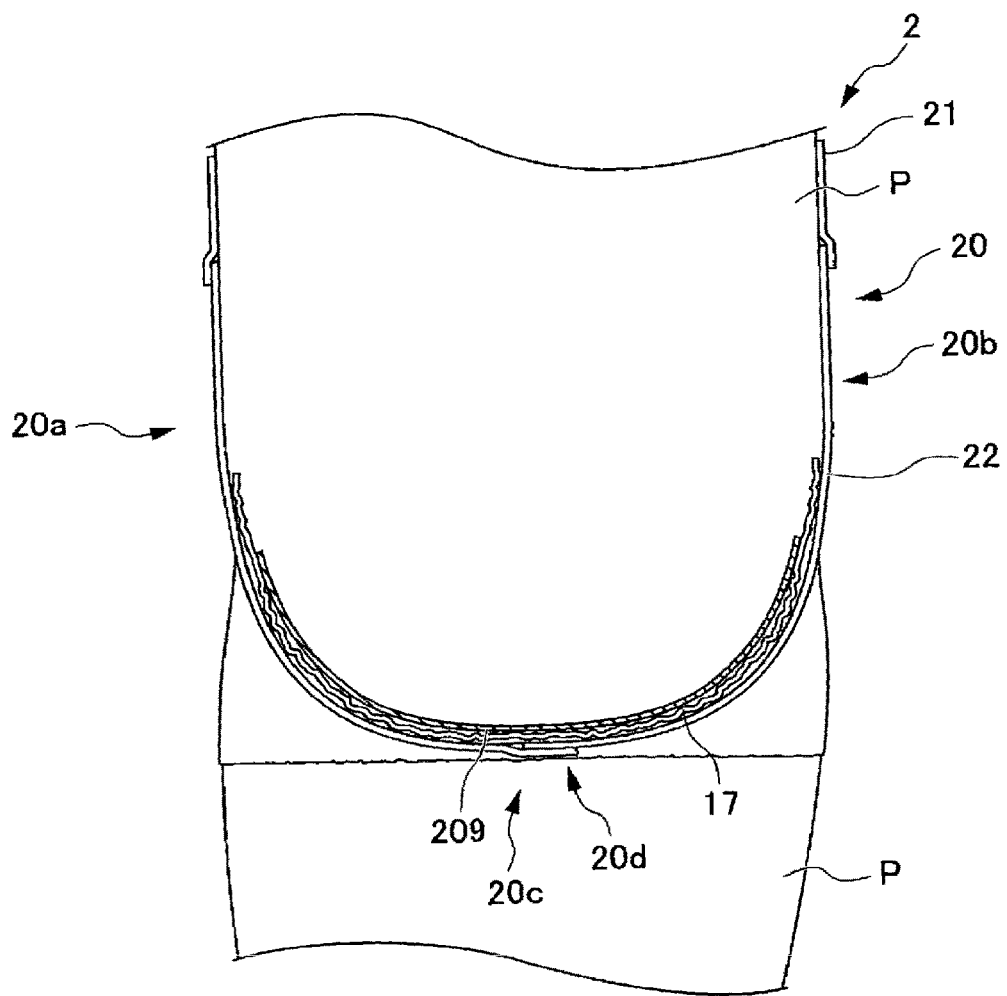
FIG. 61 is a cross-sectional view of the disposable swimwear pants 2.

FIG. 60 illustrates an example in which the disposable garment 1 is disposable swimwear pants 2. "Disposable swimwear pants" refers to garments easily produced using a material such as a nonwoven fabric instead of a sewn product made by an involved sewing process such as a cloth, and refers to a single-use product as well as products that can withstand a short period of usage and several washing cycles. FIG. 60 is a diagram illustrating the disposable swimwear pants 2 worn by the wearer P. FIG. 61 is a cross-sectional view of the disposable swimwear pants 2.

As illustrated in FIGS. 60 and 61, the chassis 20 includes the inside leg portion 20c disposed between the front portion 20a and the back portion 20b, and on the inner side of the inside leg portion 20c, the elastic sheet 17 extends between the front portion 20a and the back portion 20b. The inside leg portion 20c includes a detachable join portion 20d made of a surface fastener, a hook, or a button. The join portion 20d may be able to be freed only, and the join portion 20d may, for example, be sewn together or joined by hot melt adhesive, thermal sealing, or ultrasonic bonding, and the joint can be broken if necessary to free the inside leg portion 20c. Additionally, the inside leg portion 20c may be lined with a tear line such as a perforated line, and the tear line can be broken if necessary to free the inside leg portion 20c. In some embodiments, the inside leg portion 20c may not include the join portion 20d that can be opened. The chassis 20 has substantially the same shape as typical pants-type undergarments or garments such as trunks as well as having a similar length. The slits 29 can be provided on both sides of the chassis 20. Providing the slits 29 facilitates movement of the legs of the wearer P.

The hydrophobic sheet 209 is preferably disposed on the elastic sheet 17 of the disposable swimwear pants 2. Examples of the hydrophobic sheet 209 include a moisture permeable film, a waterproofing film. A moisture permeable film is a sheet material with characteristics that allows air to pass through but not water.

The elastic sheet 17 may include fold portions that serve as three-dimensional side gathers on the side edge portions in the width direction. Additionally, a sheet-like pad which does not contain a polymeric compound may be disposed on the elastic sheet 17. The sheet-like pad may have a structure with crushed pulp between nonwoven fabrics, or may be a cotton, felt, or layered paper formed into a sheet. Additionally, three-dimensional side gathers may be formed on the side edge portions in the width direction of the sheet-like pad.

The embodiments and modified embodiments described above can be combined as suitable. Additionally, the present invention is not limited to only the embodiments described above.

EXAMPLES

The present invention will be explained hereinbelow in greater detail with reference to a specific example of the stretchable composite sheet which is used in the present invention.

Example 1

A spunbonded nonwoven fabric (basis weight 10 g/m$^2$) was used as the air-permeable sheet, paper with a pulp content of 100% (sheet of paper for toilet paper: basis weight of 18 g/m$^2$) without printing was used as the liquid-diffusible fiber sheet, and a urethane rubber having a diameter of 620 decitex was used as the linear elastic body. The paper and the urethane rubber stretched 260% are disposed between two of the nonwoven fabrics and joined with a hot-melt adhesive (amount of hot-melt adhesive applied: 1.2 g/m$^2$) then embossed to obtain a sheet material with a total basis weight of 149.3 g/m$^2$. This sheet material was taken as Example 1. The total basis weight of the sheet material is the value of the sheet material after contracting via the restoring force of the stretched urethane rubber.

Comparative Example 1

Similar to Example 1, a nonwoven fabric and a urethane rubber are used and the urethane stretched 260% is disposed between two of the nonwoven fabrics and joined with a hot-melt adhesive (amount of hot-melt adhesive applied: 1.2 g/m$^2$) then embossed to obtain a sheet material. This sheet material was taken as Comparative Example 1. The total basis weight of the sheet material was 92.3 g/m$^2$.

Comparative Example 2

A conventional sheet material which was obtained by using a spunbonded nonwoven fabric as a front surface and a rear surface nonwoven fabrics and disposing the urethane rubber having the diameter of 620 decitex between each of the nonwoven fabrics was taken as Comparative Example 2. The total basis weight of the sheet material was 123.2 g/m$^2$.

Comparative Example 3

A conventional sheet material which was obtained by using a thermally bonded nonwoven fabric as a front surface and a rear surface nonwoven fabrics and disposing the urethane rubber having the diameter of 620 decitex between each of the nonwoven fabrics was taken as Comparative Example 3. The total basis weight of the sheet material was 144.9 g/m$^2$.

Comparative Example 4

A conventional sheet material which was obtained by using a thermally bonded nonwoven fabric as a front surface and a rear surface nonwoven fabrics and disposing the urethane rubber having the diameter of 620 decitex between each of the nonwoven fabrics was taken as Comparative Example 4. The total basis weight of the sheet material was 147.8 g/m$^2$.

Comparative Example 5

A conventional sheet material which was obtained by using a thermally bonded nonwoven fabric as a front surface and a rear surface nonwoven fabrics and disposing the urethane rubber having the diameter of 620 decitex between each of the nonwoven fabrics was taken as Comparative Example 5. The total basis weight of the sheet material was 143 g/m$^2$.

Initially, absorbency and quick drying ability and the moisture permeability of the sheet material of Example 1 and Comparative Examples 1 to 5 was evaluated.

The absorbency and quick drying ability was evaluated by combined evaluation of absorbency and quick drying ability by performing a transpiration ability (II) test (Boken standard BQEA028).

A testpiece with a diameter of approximately 9 cm was fabricated with respect to the sheet material of Example 1 and Comparative Example 1 to 5, and a mass (W) of each testpiece and a petri dish were measured. Then, 0.1 ml of water was dropped on the petri dish, the testpiece was placed thereon, and a mass (W0) was measured. The petri dish with the testpiece was allowed to stay in a standard state (20° C., humidity 65% RH), and a mass (Wt) was measured after each predetermined interval of time (5 min, 10 min, and then after every 10 min up to 60 min). A transpiration rate (%) for each predetermined period of time was then calculated from the measured mass W, W0, Wt by using a following Equation (1).

$$\text{Transpiration rate } (\%) = \{(W0-Wt)/(W0-W)\} \times 100 \quad (1)$$

The results are shown in Table 1.

TABLE 1

| | Transpiration rate (%) | | | | | | |
|---|---|---|---|---|---|---|---|
| | 5 min | 10 min | 20 min | 30 min | 40 min | 50 min | 60 min |
| Example 1 | 9.8 | 20.9 | 43.0 | 62.9 | 78.7 | 88.6 | 94.7 |
| Comparative Example 1 | 3.8 | 6.8 | 12.9 | 17.7 | 23.3 | 28.9 | 35.2 |

TABLE 1-continued

|  | Transpiration rate (%) | | | | | | |
| --- | --- | --- | --- | --- | --- | --- |
|  | 5 min | 10 min | 20 min | 30 min | 40 min | 50 min | 60 min |
| Comparative Example 2 | 4.3 | 8.1 | 15.3 | 20.4 | 27.5 | 33.0 | 39.5 |
| Comparative Example 3 | 1.7 | 3.0 | 6.3 | 7.9 | 10.2 | 12.8 | 18.3 |
| Comparative Example 4 | 0.7 | 3.5 | 5.7 | 9.5 | 11.4 | 15.2 | 17.9 |
| Comparative Example 5 | 1.7 | 3.4 | 5.2 | 9.8 | 12.6 | 15.4 | 15.3 |

The result on the transpiration rate which are shown in Table 1 clearly indicates that in Comparative Example 3 to 5, the transpiration rate is 20% or less even after 60 min, and in Comparative Example 1 and 2, the transpiration rate is less than 20% after 20 min and 40% or less even after 60 min, whereas in Example 1, the transpiration rate exceeds 20% after 10 min, the transpiration rate exceeds 40% after 20 min, and then the transpiration rate exceeds 60% after 30 min, the transpiration rate exceeds 75% after 40 min, the transpiration rate exceeds 85% after 50 min, and the transpiration rate exceeds 90% after 60 min.

In the Boken standard BQEA028, as a judgmental standard of the evaluation, the preferred transpiration rate after 20 min from a start of the test is to be of 50% or higher for a fabric product and 40% or higher for a knitted product in the case of a sports application, and 40% or higher for a fabric product and 30% or higher for a knitted product in the case of a general application.

Therefore, since the sheet material of Example 1 makes it possible to obtain a transpiration rate of 40% or higher, it can be said that such material can be comfortably worn both in sports application and general application.

It follows from the above, that the disposable garment of the present invention that uses the sheet material of Example 1 has a very high absorbency and quick drying ability.

The moisture permeability was then tested by the A-1 method (calcium chloride method) of JIS-L1099 (2012), and the moisture permeability ($g/m^2 \cdot h$) was determined and evaluated.

The moisture permeability is defined as a value obtained by converting a mass (g) of water vapor permeating through the textile product to a mass per 1 $m^2 \times 1$ h of the textile product under standard temperature and humidity.

A testpiece was sampled from the sheet material of Example 1 and Comparative Example 1 to 5 according to JISL0105-6.3 (cloth-like sample and the testpiece thereof).

A device and material such as a moisture-permeable cup, a thermostat-hygrostat, a round plate, and a moisture absorbent corresponding to the calcium chloride method were prepared and the test was performed.

Initially, about 33 g of the moisture absorbent was placed in the moisture-permeable cup which was warmed up to approximately 40° C. in advance, the moisture-permeable cup was vibrated to obtain a uniform material, the surface was leveled with a spatula, and a distance between the moisture absorbent and a lower surface of the testpiece was adjusted to 3 mm by using the round plate.

Then, three of the testpieces with a diameter of about 70 mm were sampled according to JISL0105-6.3 (cloth-like sample and the testpiece thereof) with respect to the sheet material of Example 1 and Comparative Example 1 to 5.

Each testpiece was placed to be concentric with the moisture-permeable cup, such that the surface of the testpiece faced the moisture absorbent, a packing and a ring were successively mounted and fixed with a wing nut, and a mounting-side surface was sealed with a vinyl pressure-sensitive adhesive tape to form a test sample. The test sample was placed at a location inside the thermostat-hygrostat with a temperature of 40° C.±2° C. and a humidity of 90% RH±5% RH where the air speed approximately 10 mm above the testpiece did not exceed 0.8 m/s. The test sample was taken out after 1 h and a mass (a1) was immediately measured with an accuracy up to 1 mg. After the measurement, the test sample was again placed at the same location in the thermostat-hygrostat, the test sample was taken out after 1 h, and a mass (a2) was immediately measured with an accuracy up to 1 mg. The moisture permeability PA1 ($g/m^2 \cdot h$) was then calculated from the measured mass a1 and a2 using the following Equation (2).

$$\text{Moisture permeability } PA1(g/m^2 \cdot h) = (a2 - a1)/SA1 \quad (2)$$

In Equation (2), a2−a1 is the change amount (g/h) of a mass of the test sample per 1 h, and SA1 is the moisture permeation area ($m^2$).

The test result is the average value of three results rounded to the first decimal place as stipulated by JISZ8401 (rounding method). The obtained results are shown in Table 2.

TABLE 2

|  | Moisture permeability ($g/m^2 \cdot h$) |
| --- | --- |
| Example 1 | 564 |
| Comparative Example 1 | 563 |
| Comparative Example 2 | 435 |
| Comparative Example 3 | 496 |
| Comparative Example 4 | 526 |
| Comparative Example 5 | 433 |

The results relating to moisture permeability which is shown in Table 2 clearly indicate that the moisture permeability is 500 $g/m^2 \cdot h$ or less in Comparative Examples 2, 3, and 5, 563 $g/m^2 \cdot h$ in Comparative Example 1, and 526 $g/m^2 \cdot h$ in Comparative Example 4. Meanwhile, in Example 1, the moisture permeability is 564 $g/m^2 \cdot h$, which is higher than that of the comparative examples.

It follows from the above that the functional base fabric material of the present invention is highly stable and has good moisture permeability.

The moisture permeability evaluation result and absorbency and quick drying ability evaluation result after 20 min and 60 min are shown in Table 3 with respect to Example 1 and Comparative Example 1 to 5.

The absorbency and quick drying ability and the moisture permeability evaluation results shown in Table 3 clearly demonstrate that the functional base fabric material of the present invention which is represented by Example 1 is superior to the functional base fabric material of Comparative Example 1 to 5 in both the absorbency and quick drying ability and the moisture permeability and has higher transpiration ratio and moisture permeability.

The results presented hereinabove clearly demonstrate the effects of the functional base fabric material for a disposable product and of the disposable fabric product in accordance with the present invention.

TABLE 3

| | Absorbency and quick drying ability after 20 min (%) | Absorbency and quick drying ability after 60 min (%) | Moisture permeability (g/m² · h) | Total basis weight of sheet material (g/m²) |
|---|---|---|---|---|
| Example 1 | 43.0 | 94.7 | 564 | 149.3 |
| Comparative Example 1 | 12.9 | 35.2 | 563 | 92.3 |
| Comparative Example 2 | 15.3 | 39.5 | 435 | 123.2 |
| Comparative Example 3 | 6.3 | 18.3 | 496 | 144.9 |
| Comparative Example 4 | 5.7 | 17.9 | 526 | 147.8 |
| Comparative Example 5 | 5.2 | 15.3 | 433 | 143.0 |

It goes without saying that the present invention is not limited to the above-described embodiment and is inclusive of all embodiments making it possible to attain the object of the present invention.

Cool contact feeling (cool feeling) and wet contact cold feeling (stickiness during perspiration) of the sheet material in which paper is interposed between each of the nonwoven fabrics and a sheet material in which no paper is interposed between each of the nonwoven fabrics were then tested.

Examples 2 to 5

The sheet material was prepared by using the nonwoven fabric, paper, hot-melt adhesive, and urethane rubber similar to those of Example 1. The paper used in Example 2 and 3 was subjected to the embossing process the number of times shown in Table 4, by using the pair of the flat roll. The basis weight of the paper used, the total basis weight of the hot-melt adhesive, and the total basis weight of the sheet material are all shown in Table 4. The cool contact feeling and wet contact hot feeling were measured by the below-described method with respect to the sheet materials. The results of the cool contact feeling and the wet contact cold feeling are shown in Table 5.

Cool contact feeling (W/m²·K): the cool contact feeling represents the degree of sensation of cooling and refreshing in wearing as the amount of heat transferred in wearing. Thus, the cool contact feeling is cooling and refreshing when the amount of heat transferred is great. In other words, a testpiece with a large value for the cool contact feeling is superior. The cool contact feeling was measured by the following method by using a precision rapid thermal physical property measurement device (KES-F7 Thermolab II, manufactured by KATO TECH CO., LTD.). The testpiece (6 cm×6 cm) cut out from the sheet material was placed on a base plate at a temperature of 20° C. A hot plate equipped with a precision thermal sensor was heated to 40° C., the hot plate was placed on the testpiece at 20° C., and the cool contact feeling value (qmax) was calculated from the heat dissipation behavior measured with the thermal sensor of the hot plate.

Wet contact cold feeling (W/m²·K): The wet contact cold feeling represents the degree of stickiness when humid, as in when sweaty, as the amount of heat transferred. Thus, a testpiece has no stickiness and is superior when a low wet contact cold feeling is small. The wet contact cold feeling was measured by the following method by using a precision rapid thermal physical property measurement device (KES-F7 Thermolab II, manufactured by KATO TECH CO., LTD.).

The testpiece (6 cm×6 cm) cut out from the sheet material was caused to absorb water at 80 g/m², and the resultant testpiece carrying water was placed on the base plate at a temperature of 20° C. The hot plate equipped with a precision thermal sensor was heated to 40° C., the hot plate was placed on the testpiece at 20° C., and the wet contact cold feeling value (wet-qmax) was calculated from the heat dissipation behavior measured with the thermal sensor of the hot plate.

Comparative Example 6

The cool contact feeling and wet contact cold feeling were tested in the same manner as in Example 2 to 5 by using the sheet material similar to that of Comparative Example 2. The results are shown in Table 5.

Comparative Example 7

The cool contact feeling and wet contact cold feeling were tested in the same manner as in Example 2 to 5 by using the sheet material similar to that of Comparative Example 4. The results are shown in Table 5.

Comparative Example 8

The cool contact feeling and wet contact cold feeling were tested in the same manner as in Example 2 to 5 by using the sheet material similar to that of Comparative Example 3. The results are shown in Table 5.

Comparative Example 9

The cool contact feeling and wet contact cold feeling were tested in the same manner as in Example 2 to 5 by using the sheet material similar to that of Comparative Example 5. The results are shown in Table 5.

TABLE 4

| | Paper basis weight (g/m²) | Amount of hot-melt adhesive (g/m²) | Times embossed (times) | Total basis weight of sheet material (g/m²) |
|---|---|---|---|---|
| Example 2 | 18 | 1.2 | 1 | 150.8 |
| Example 3 | 18 | 1.2 | 2 | 148.1 |
| Example 4 | 18 | 1.2 | — | 146.2 |
| Example 5 | 13 | 1.2 | — | 137.4 |

TABLE 5

|  | Cool contact feeling | Wet contact cold feeling | Total basis weight of sheet material (g/m$^2$) |
| --- | --- | --- | --- |
| Example 2 | 45 | 91 | 150.8 |
| Example 3 | 49 | 95 | 148.1 |
| Example 4 | 42 | 90 | 146.2 |
| Example 5 | 50 | 96 | 137.4 |
| Comparative Example 6 | 46 | 164 | 123.2 |
| Comparative Example 7 | 37 | 165 | 144.9 |
| Comparative Example 8 | 38 | 225 | 147.8 |
| Comparative Example 9 | 27 | 119 | 143.0 |

As seen from the results shown in Table 5, Examples 2 to 5 have equal to or greater values and are thus superior to Comparative Examples 6 to 9 in terms of cool contact feeling. Additionally, in terms of wet contact cold feeling, the Examples 2 to 5 all have values equal to or less than 100 compared to Conventional Examples 6 to 9 which had values equal to or more than 100. Thus, the sheet material of Examples 2 to 5 can be considered to have less stickiness when sweaty than the sheet material of Comparative Examples 6 to 9. As a result, it can be seen that Examples 2 to 5 are superior in terms of cool contact feeling and wet contact cold feeling.

REFERENCE SIGNS LIST

1 Disposable garment
20 Chassis
20a Front portion
20b Back portion
20c Inside leg portion
20f Leg cuff opening
21 Torso band
21a Torso band opening
200 Stretchable composite sheet
201 Liquid diffusion fiber sheet
202 Linear elastic body
203 Air permeable sheet
205 Air permeable sheet

The invention claimed is:

1. A disposable garment, comprising:
a torso band forming a torso band opening; and
a chassis disposed on a lower side of the torso band,
wherein the chassis comprises a stretchable composite sheet having extensibility, the stretchable composite sheet being a multi-layer structure comprising a first air permeable sheet, a second air permeable sheet, and a liquid diffusion fiber sheet and a linear elastic body disposed between the first air permeable sheet and the second air permeable sheet,
the liquid diffusion fiber sheet has a weakened portion,
the stretchable composite sheet is formed by joining the first air permeable sheet and the liquid diffusion fiber sheet via the linear elastic body which is elongated and to which an adhesive is applied, and joining the liquid diffusion fiber sheet and the second air permeable sheet, and
the chassis has stretchability that imparts a pressing force against a wearer.

2. The disposable garment according to claim 1, wherein the stretchable composite sheet is formed by joining the first air permeable sheet and the liquid diffusion fiber sheet via the linear elastic body which is elongated and to which the adhesive is applied such that a first joined portion and a first non-joined portion are formed between the first air permeable sheet and the liquid diffusion fiber sheet, and directly joining the liquid diffusion fiber sheet and the second air permeable sheet such that a second joined portion and a second non-joined portion are formed between the liquid diffusion fiber sheet and the second air permeable sheet.

3. The disposable garment according to claim 2, wherein the chassis comprises a front portion, a back portion, and a crotch portion disposed between the front portion and the back portion, and the chassis has stretchability that imparts a pressing force against a crotch and around a leg of the wearer.

4. The disposable garment according to claim 3, wherein the crotch portion is provided with a plurality of the linear elastic bodies extending from a leg cuff opening on one side toward a leg cuff opening on the other side.

5. The disposable garment according to claim 3, wherein the crotch portion is provided with a plurality of the linear elastic bodies orientated in a direction that joins the front portion and the back portion.

6. The disposable garment according to claim 2, wherein the linear elastic body is provided in plurality at an interval of 3.00 to 6.25 mm.

7. The disposable garment according to claim 2, wherein the linear elastic body is in contact with the liquid diffusion fiber sheet.

8. The disposable garment according to claim 2, wherein the weakened portion of the liquid diffusion fiber sheet is formed by an embossing process.

9. The disposable garment according to claim 2, wherein the liquid diffusion fiber sheet is made by a paper making process and comprises a pulp fiber.

10. The disposable garment according to claim 9, wherein the liquid diffusion fiber sheet is a paper sheet.

11. The disposable garment according to claim 2, wherein the stretchable composite sheet is an integral multi-layer structure joined by the adhesive.

12. The disposable garment according to claim 2, wherein the adhesive is a hot-melt adhesive, and a portion of the hot-melt adhesive penetrates into the liquid diffusion fiber sheet to form an anchor portion for adhesion.

13. The disposable garment according to claim 2, wherein a portion of the stretchable composite sheet where the linear elastic body is disposed has an extensibility of 120 to 500% in a stretching direction of the linear elastic body.

14. The disposable garment according to claim 2, wherein a plurality of concaves and convexes are formed in a surface of the stretchable composite sheet along a stretching direction of the linear elastic body.

15. The disposable garment according to claim 2, wherein the torso band comprises a fold on a side of the torso band opening.

16. The disposable garment according to claim 4, wherein a non-gather portion is formed on edges of the leg cuff openings.

17. The disposable garment according to claim 8, wherein a printed layer is formed on a surface of the liquid diffusion fiber sheet before the embossing process is applied.

18. The disposable garment according to claim 2, wherein the chassis comprises a front portion and a back portion, and the disposable garment further comprises an inner sheet disposed between the front portion and the back portion of the chassis.

19. The disposable garment according to claim 2, wherein the chassis comprises a front portion and a back portion, and the disposable garment further comprises an absorbent member comprising an absorbent core, the absorbent member being disposed between the front portion and the back portion of the chassis.

20. The disposable garment according to claim 19, wherein the absorbent member is continuously or intermittently joined to the chassis along a line that joins the front portion and the back portion of the chassis.

21. The disposable garment according to claim 2, wherein the chassis comprises a front portion and a back portion, and the front portion and the back portion of the chassis have the same size.

22. The disposal disposable garment according to claim 2,
wherein a nonwoven fabric is used as the first air permeable sheet and the second air permeable sheet, and a paper is used as the liquid diffusion fiber sheet, and
a transpiration rate of the stretchable composite sheet exceeds 40% after 20 minutes.

23. The disposable garment according to claim 22, wherein the stretchable composite sheet in which 80 g/m$^2$ of water is absorbed has a wet contact cold feeling of 100 w/m$^2$·K or less.

24. The disposable garment according to claim 22, wherein the stretchable composite sheet has a cool contact feeling of 42 to 50 w/m$^2$·K.

25. The disposable garment according to claim 8, wherein the liquid diffusion fiber sheet is joined to the first air permeable sheet and the second air permeable sheet after the embossing process is applied to the liquid diffusion fiber sheet.

26. The disposable garment according to claim 1, wherein a basis weight of the liquid diffusion fiber sheet is greater than a basis weight of the first air permeable sheet and a basis weight of the second air permeable sheet.

27. The disposable garment according to claim 26, wherein a nonwoven fabric is used as the first air permeable sheet and the second air permeable sheet, and a paper is used as the liquid diffusion fiber sheet, and
a transpiration rate of the stretchable composite sheet exceeds 40% after 20 minutes.

28. The disposable garment according to claim 19, wherein the stretchable composite sheet in which 80 g/m$^2$ of water is absorbed has a wet contact cold feeling of 100 w/m$^2$·K or less.

29. The disposable garment according to claim 22, wherein the stretchable composite sheet has a cool contact feeling of 42 to 50 w/m$^2$·K.

* * * * *

UNITED STATES PATENT AND TRADEMARK OFFICE
CERTIFICATE OF CORRECTION

PATENT NO. : 10,463,546 B2
APPLICATION NO. : 15/533886
DATED : November 5, 2019
INVENTOR(S) : Kikuo Yamada Page 1 of 1

It is certified that error appears in the above-identified patent and that said Letters Patent is hereby corrected as shown below:

On the Title Page

Item (30), the Foreign Application Priority Data is incorrect. Item (30) should read:
-- (30) Foreign Application Priority Data
Dec. 12, 2014 (WO) ................. PCT/JP2014/083062
May 12, 2015 (WO) ................. PCT/JP2015/063688
Jun. 25, 2015 (WO) ................. PCT/JP2015/068434
Jul. 28, 2015 (WO) ................. PCT/JP2015/071339
Aug. 10, 2015 (WO) ................. PCT/JP2015/072716
Nov. 13, 2015 (WO) ................. PCT/JP2015/082635 --

Signed and Sealed this
Thirty-first Day of December, 2019

Andrei Iancu
*Director of the United States Patent and Trademark Office*